US011918516B1

(12) United States Patent
Junger et al.

(10) Patent No.: US 11,918,516 B1
(45) Date of Patent: Mar. 5, 2024

(54) SYSTEMS AND METHODS FOR TREATING PATIENTS WITH CLOSED-ANGLE OR NARROW-ANGLE GLAUCOMA USING AN EXCIMER LASER UNIT

(71) Applicant: Elios Vision, Inc., Los Angeles, CA (US)

(72) Inventors: Johannes Junger, Gilching (DE); Markus Enders, Munich (DE)

(73) Assignee: Elios Vision, Inc., Los Angeles, CA (US)

( * ) Notice: Subject to any disclaimer, the term of this patent is extended or adjusted under 35 U.S.C. 154(b) by 0 days.

(21) Appl. No.: 17/899,310

(22) Filed: Aug. 30, 2022

(51) Int. Cl.
*A61F 9/008* (2006.01)
*A61F 2/16* (2006.01)
*A61B 17/00* (2006.01)
*A61B 18/00* (2006.01)
*A61F 9/007* (2006.01)

(52) U.S. Cl.
CPC ........ *A61F 9/00802* (2013.01); *A61F 2/1601* (2015.04); *A61B 2017/00199* (2013.01); *A61B 2017/00973* (2013.01); *A61B 2018/00178* (2013.01); *A61B 2018/00994* (2013.01); *A61B 2218/002* (2013.01); *A61B 2218/007* (2013.01); *A61F 9/00745* (2013.01); *A61F 2009/00868* (2013.01); *A61F 2009/00891* (2013.01)

(58) Field of Classification Search
CPC ................ A61F 9/00802; A61F 2/1601; A61F 9/00745; A61F 2009/00868; A61F 2009/00891; A61B 2017/00199; A61B 2017/00973; A61B 2018/00178; A61B 2018/00994; A61B 2218/002; A61B 2218/007

USPC .......................................................... 606/6
See application file for complete search history.

(56) References Cited

U.S. PATENT DOCUMENTS

| 4,607,622 A | 8/1986 | Fritch et al. |
| 4,846,172 A | 7/1989 | Berlin |
| 4,862,888 A | 9/1989 | Yessik |
| 5,281,241 A | 1/1994 | Patel |

(Continued)

FOREIGN PATENT DOCUMENTS

| DE | 19920615 A1 | 12/2000 |
| DE | 10023176 A1 | 11/2001 |

(Continued)

OTHER PUBLICATIONS

Dietlein et al., "Erbium: YAG Laser Trabecular Ablation (LTA) in the Surgical Treatment of Glaucoma", Lasers in Surgery and Medicine, Jan. 6, 1999, vol. 23, pp. 104-110.

(Continued)

*Primary Examiner* — Aaron F Roane
(74) *Attorney, Agent, or Firm* — Greenberg Traurig, LLP; Roman Fayerberg; David J. Dykeman

(57) ABSTRACT

An illustrative method of treating a patient having an eye condition includes determining that the patient has a closed-angle or narrow-angle glaucoma. The method further includes treating the closed-angle or narrow-angle glaucoma during a surgical procedure performed on the patient. The method further includes, during the surgical procedure, treating the patient with an excimer laser to create a plurality of perforations in the trabecular meshwork by applying a plurality of shots to the trabecular meshwork from the excimer laser.

19 Claims, 35 Drawing Sheets

(56) References Cited

U.S. PATENT DOCUMENTS

| | | |
|---|---|---|
| 5,323,766 A | 6/1994 | Uram |
| 5,738,677 A | 4/1998 | Colvard et al. |
| 5,755,716 A | 5/1998 | Garito et al. |
| 5,865,831 A | 2/1999 | Cozean et al. |
| 6,197,056 B1 | 3/2001 | Schachar |
| 6,283,974 B1 | 9/2001 | Alexander |
| 6,743,221 B1 | 6/2004 | Hobart et al. |
| 7,443,296 B2 | 10/2008 | Mezhinsky et al. |
| 7,568,619 B2 | 8/2009 | Todd et al. |
| 7,801,271 B2 | 9/2010 | Gertner et al. |
| 9,489,785 B2 | 11/2016 | Klammer et al. |
| 9,642,746 B2 | 5/2017 | Berlin |
| 10,383,689 B2 | 8/2019 | Berlin |
| 11,076,933 B2 | 8/2021 | Junger et al. |
| 11,076,992 B2 | 8/2021 | Junger et al. |
| 11,103,382 B2 | 8/2021 | Junger et al. |
| 11,234,866 B2 | 2/2022 | Junger et al. |
| 11,389,239 B2 | 7/2022 | Junger et al. |
| 11,464,677 B2 | 10/2022 | Junger et al. |
| 11,529,260 B2 | 12/2022 | Junger et al. |
| 2002/0013572 A1 | 1/2002 | Berlin |
| 2002/0183726 A1 | 12/2002 | Elbrecht et al. |
| 2004/0082939 A1 | 4/2004 | Berlin |
| 2004/0114879 A1 | 6/2004 | Hiereth et al. |
| 2004/0147985 A1 | 7/2004 | MacFarland et al. |
| 2005/0192480 A1 | 9/2005 | Toriya et al. |
| 2005/0283148 A1 | 12/2005 | Janssen et al. |
| 2006/0111699 A1 | 5/2006 | Neuberger |
| 2006/0244652 A1 | 11/2006 | Tethrake et al. |
| 2007/0027443 A1 | 2/2007 | Rose et al. |
| 2007/0122096 A1 | 5/2007 | Temelkuran et al. |
| 2007/0147752 A1 | 6/2007 | Weisberg et al. |
| 2007/0219601 A1 | 9/2007 | Neuberger |
| 2007/0265602 A1 | 11/2007 | Mordaunt et al. |
| 2008/0054073 A1 | 3/2008 | Charles |
| 2008/0082078 A1 | 4/2008 | Berlin |
| 2008/0097415 A1 | 4/2008 | Zimare et al. |
| 2008/0108981 A1 | 5/2008 | Telfair et al. |
| 2008/0108983 A1 | 5/2008 | Nadolski |
| 2008/0161781 A1 | 7/2008 | McArdle et al. |
| 2008/0269734 A1 | 10/2008 | Vila Echague et al. |
| 2009/0030300 A1 | 1/2009 | Hhaboussi et al. |
| 2009/0118715 A1 | 5/2009 | Mansour |
| 2009/0157064 A1 | 6/2009 | Hodel |
| 2010/0019125 A1 | 1/2010 | Stefani et al. |
| 2010/0068141 A1 | 3/2010 | Kaushal et al. |
| 2010/0324543 A1 | 12/2010 | Kurtz et al. |
| 2011/0295243 A1 | 12/2011 | Peyman |
| 2011/0301507 A1 | 12/2011 | Romano et al. |
| 2012/0275481 A1 | 11/2012 | Riggs |
| 2013/0041357 A1 | 2/2013 | Neuberger |
| 2013/0085484 A1 | 4/2013 | Van Valen et al. |
| 2014/0058367 A1 | 2/2014 | Dantus |
| 2014/0188096 A1 | 7/2014 | Chia et al. |
| 2014/0316388 A1 | 10/2014 | Hipsley |
| 2015/0051607 A1 | 2/2015 | Hajishah et al. |
| 2015/0080783 A1 | 3/2015 | Berlin |
| 2015/0148615 A1 | 5/2015 | Brennan et al. |
| 2015/0217133 A1 | 8/2015 | Angeley et al. |
| 2015/0297408 A1 | 10/2015 | Dolzan et al. |
| 2015/0305811 A1 | 10/2015 | Neuberger |
| 2015/0366706 A1 | 12/2015 | Belkin et al. |
| 2015/0374549 A1 | 12/2015 | Scott |
| 2017/0100041 A1 | 4/2017 | Kasamatsu et al. |
| 2017/0202708 A1 | 7/2017 | Berlin |
| 2017/0304001 A1 | 10/2017 | Searle et al. |
| 2018/0000337 A1 | 1/2018 | Chen et al. |
| 2018/0042772 A1 | 2/2018 | Mansour |
| 2018/0263647 A1 | 9/2018 | Aljuri et al. |
| 2018/0303667 A1 | 10/2018 | Peyman |
| 2018/0353328 A1 | 12/2018 | Bacher et al. |
| 2018/0360310 A1 | 12/2018 | Berlin |
| 2019/0105200 A1 | 4/2019 | Hipsley |
| 2019/0117459 A1 | 4/2019 | Berlin |
| 2019/0262071 A1 | 8/2019 | Thorn et al. |
| 2020/0078216 A1 | 3/2020 | Raksi |
| 2020/0078217 A1 | 3/2020 | Raksi |
| 2020/0330157 A1 | 10/2020 | Junger et al. |
| 2020/0330181 A1 | 10/2020 | Junger et al. |
| 2020/0330266 A1* | 10/2020 | Junger .................. A61F 9/0008 |
| 2020/0330274 A1 | 10/2020 | Junger et al. |
| 2020/0330275 A1 | 10/2020 | Junger et al. |
| 2020/0330279 A1 | 10/2020 | Junger et al. |
| 2020/0330280 A1 | 10/2020 | Junger et al. |
| 2020/0330281 A1 | 10/2020 | Junger et al. |
| 2020/0390600 A1 | 12/2020 | Perera et al. |
| 2021/0235986 A1 | 8/2021 | Juhasz et al. |
| 2021/0259880 A1 | 8/2021 | Newton et al. |
| 2021/0298945 A1 | 9/2021 | Juhasz et al. |
| 2022/0022997 A1 | 1/2022 | Junger et al. |
| 2022/0023098 A1 | 1/2022 | Junger et al. |
| 2022/0031513 A1 | 2/2022 | Junger et al. |
| 2022/0151828 A1 | 5/2022 | Junger et al. |
| 2022/0183882 A1 | 6/2022 | Mosaed et al. |
| 2022/0183887 A1 | 6/2022 | Junger et al. |
| 2022/0280343 A1 | 9/2022 | Junger et al. |
| 2022/0387107 A1 | 12/2022 | Junger et al. |
| 2022/0387218 A1 | 12/2022 | Junger et al. |

FOREIGN PATENT DOCUMENTS

| | | |
|---|---|---|
| DE | 10138984 A1 | 3/2003 |
| EP | 1835862 B1 | 6/2011 |
| EP | 2120760 B1 | 9/2015 |
| WO | 2019060756 A1 | 3/2019 |
| WO | WO 2020215062 A1 | 10/2020 |
| WO | WO 2020215064 A1 | 10/2020 |
| WO | WO 2020215066 A1 | 10/2020 |
| WO | WO 2020215067 A1 | 10/2020 |
| WO | WO 2020215068 A1 | 10/2020 |
| WO | WO 2020215069 A1 | 10/2020 |
| WO | WO 2020215071 A1 | 10/2020 |
| WO | WO 20200215073 A1 | 10/2020 |

OTHER PUBLICATIONS

Francis et al., "Combined Cataract Extraction and Trabeculotomy by the Internal Approach for Coexisting Cataract and Open-Angle Glaucoma: Initial Results", Journal of Cataract & Refractive Surgery, Jul. 1, 2008, vol. 34, pp. 1096-1103.

Wilmsmeyer et al., "Excimer Laser Trabeculotomy: A New, Minimally Invasive Procedure for Patients With Glaucoma", Graefe's Archive for Clinical and Experimental Ophthalmology, Oct. 19, 2005, vol. 244, pp. 670-676.

Crandall, Alan, "Combining Cataract and Glaucoma Surgery", Review of Ophthalmology, 1-4, Jun. 13, 2008.

ExTra Operating Instructions, Manufacturer: MLase AG, published prior to Jan. 1, 2018. Third Party Submission in 010402.

Grover, Davinder S. "When You Have Cataracts and Glaucoma", Glaucoma Research Foundation, Oct. 29, 2017.

Investigation Testing Authorization Application, YUI Laser AG Published Jan. 1, 2016. Third Party Submission in 010302.

Leung et al., "Anterior Chamber Angle Measurement with Anterior Segment Optical Coherence Tomography: A Comparison between Slit Lamp OCT and Visante OCT", Investigative Ophthalmology & Visual Science, vol. 49, No. 8, pp. 3469-3474, Aug. 2008.

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).

Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).

Tsai, James C. "High Eye Pressure and Glaucoma", Glaucoma Research Foundation, Oct. 29, 2017.

Berlin, et al., "Excimer Laser Trabeculostomy: An Effective Microinvasive Glaucoma Surgery Procedure for Open-Angle Glaucoma", published Dec. 19, 2013 Third Party Submission in 010503.

U.S. Appl. No. 17/842,933, filed Jun. 17, 2022, Combination Treatment Using Phaco and ELT.

(56) References Cited

OTHER PUBLICATIONS

U.S. Appl. No. 17/579,803, filed Jan. 20, 2022, Excimer Laser Fiber Illumination.

U.S. Appl. No. 16/389,346 US20200330181A1 U.S. Pat. No. 11,076,933, filed Apr. 19, 2019 Oct. 22, 2020 Aug. 3, 2021, Authentication Systems and Methods for an Excimer Laser System.

U.S. Appl. No. 17/363,656, US20220022997A1, filed Jun. 30, 2021 Jan. 27, 2022, Authentication Systems and Methods for an Excimer Laser System.

U.S. Appl. No. 16/389,359 US20200330279A1 U.S. Pat. No. 11,103,382, filed Apr. 19, 2019 Oct. 22, 2020 Aug. 31, 2021, Systems and Methods for Performing an Intraocular Procedure for Treating an Eye Condition.

U.S. Appl. No. 16/389,446 US20200330266A1, filed Apr. 19, 2019 Oct. 22, 2020, Combination Treatment Using ELT.

U.S. Appl. No. 17/592,027 US20220151828A1, filed Feb. 3, 2022 May 19, 2022, Combination Treatment Using ELT.

U.S. Appl. No. 16/389,460 US20200330274A1, U.S. Pat. No. 11,076,992, filed Apr. 19, 2019 Oct. 22, 2020 Aug. 3, 2021, Methods of Transverse Placement in ELT.

U.S. Appl. No. 17/363,726 US20220023098A1, filed Jun. 30, 2021 Jan. 27, 2022, Methods of Transverse Placement in ELT.

U.S. Appl. No. 16/389,425 US20200330280A1 U.S. Pat. No. 11,234,866, filed Apr. 19, 2019 Oct. 22, 2020 Feb. 1, 2022, Personalization of Excimer Laser Fibers.

U.S. Appl. No. 17/644,930 US20220183887, filed Dec. 17, 2021 Jun. 16, 2022, Personalization of Excimer Laser Fibers.

U.S. Appl. No. 16/389,386 US20200330157A1 U.S. Pat. No. 11,389,239, filed Apr. 19, 2019 Oct. 22, 2020 Jul. 19, 2022, Enhanced Fiber Probes for ELT.

U.S. Appl. No. 17/842,971, filed Jun. 17, 2022, Enhanced Fiber Probes for ELT.

U.S. Appl. No. 17/400,191, filed Aug. 12, 2021, Systems and Methods for Performing an Intraocular Procedure for Treating an Eye Condition.

U.S. Appl. No. 17/899,285, filed Aug. 30, 2022, Systems and Methods for Prophylactic Treatment of an Eye Using an Excimer Laser Unit.

U.S. Appl. No. 17/899,330, filed Aug. 30, 2022, Systems and Methods for a Combined Excimer Laser and Phacoemulsification Unit.

U.S. Appl. No. 17/899,350, filed Aug. 30, 2022, Systems and Methods for Applying Excimer Laser Energy With Transverse Placement in the Eye.

* cited by examiner

FIG. 11
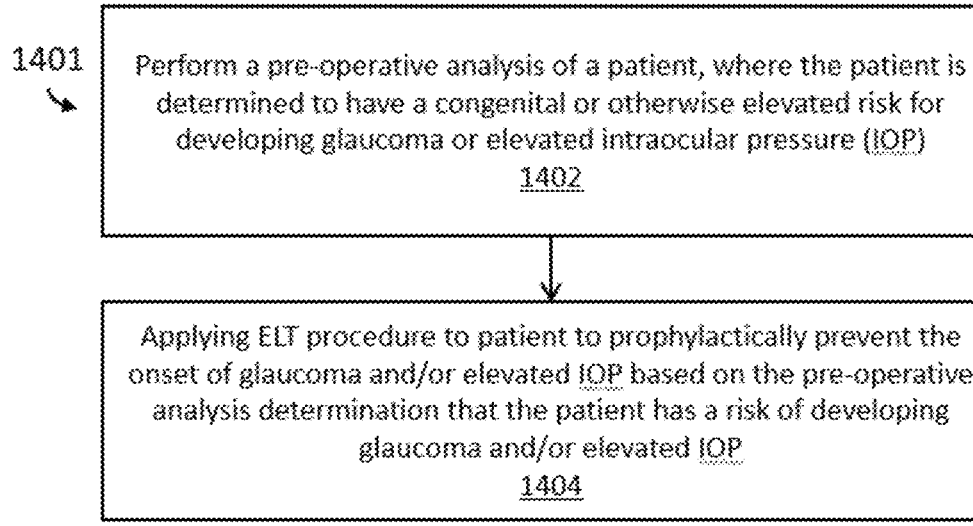
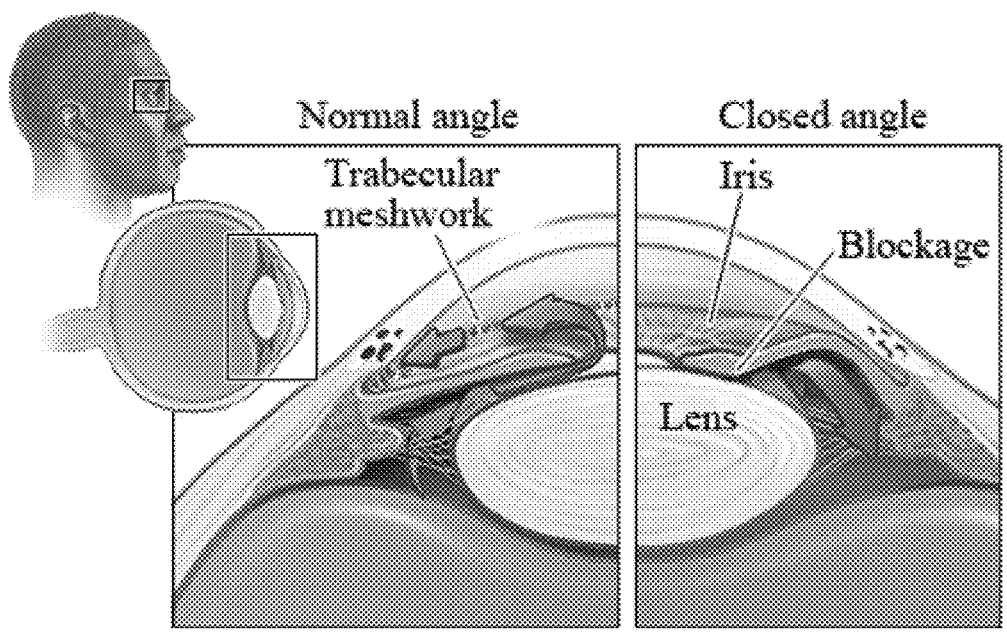
FIG. 12A  FIG. 12B

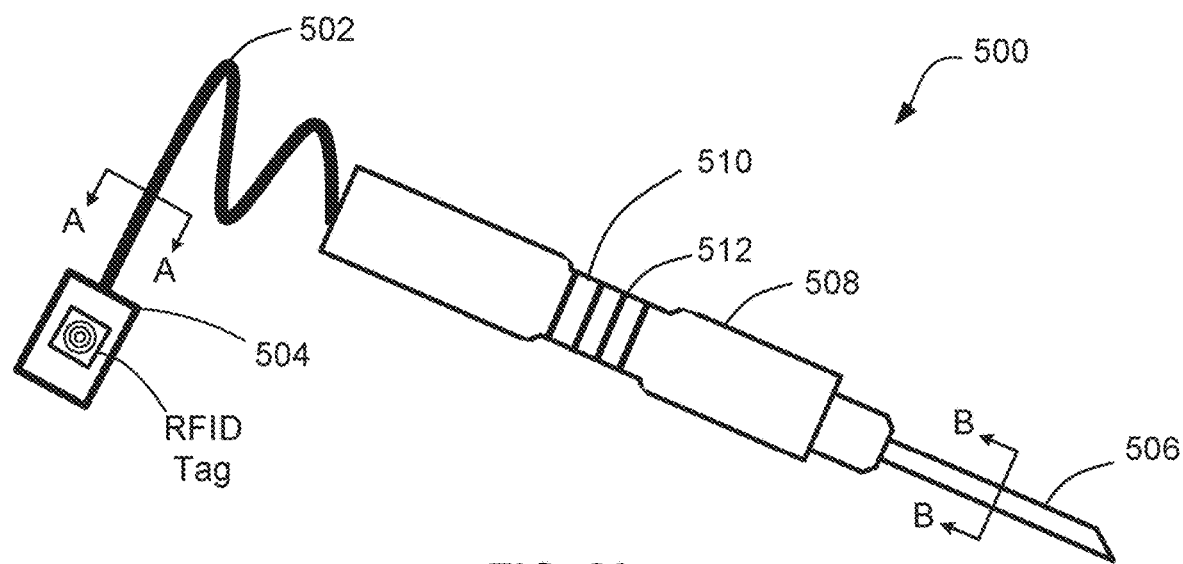
FIG. 29
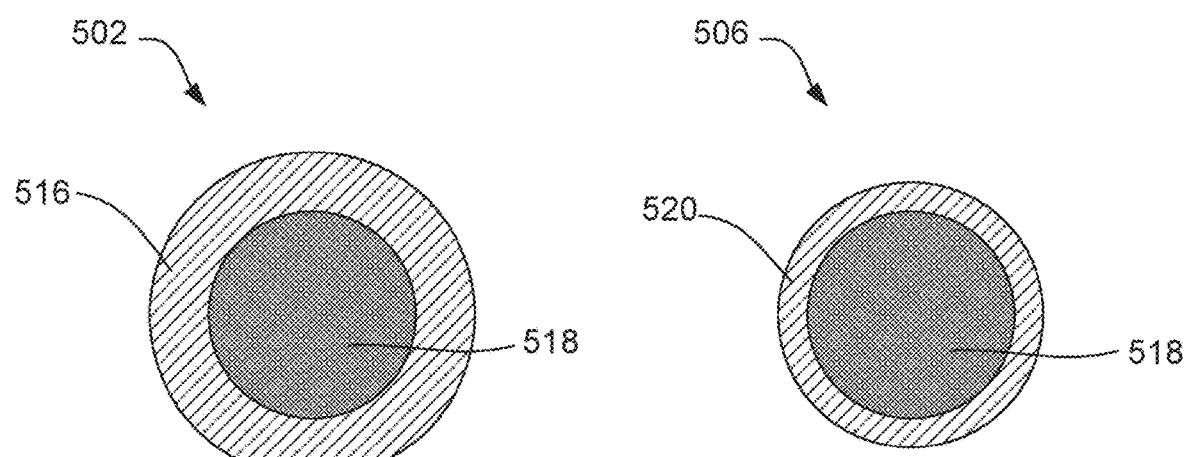
FIG. 30  FIG. 31

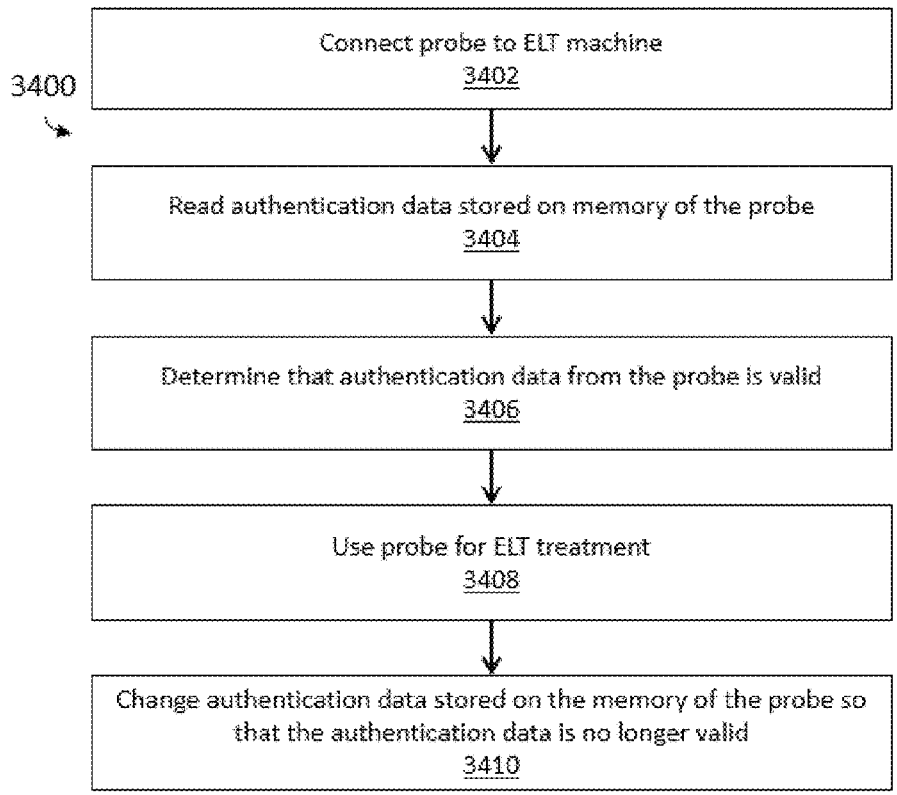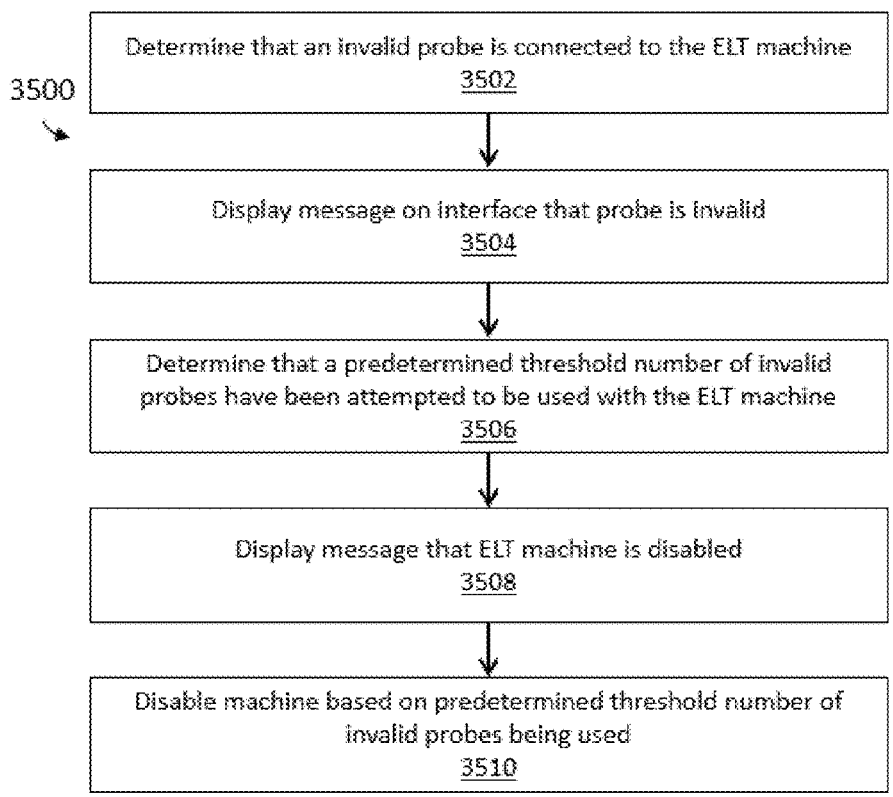

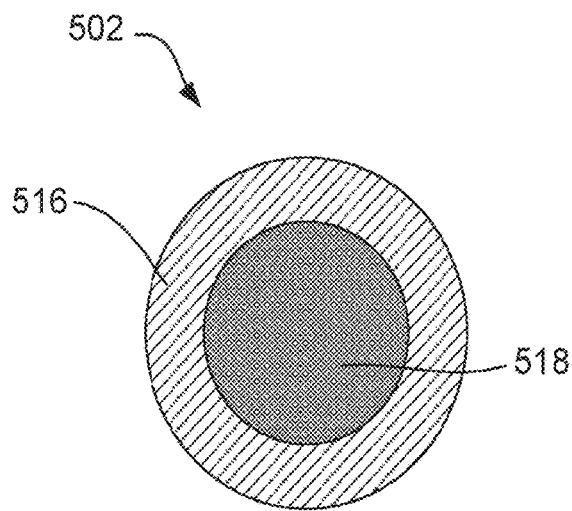
FIG. 46
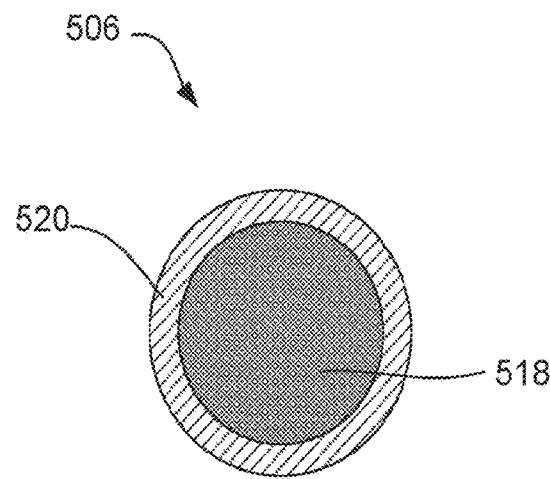
FIG. 47
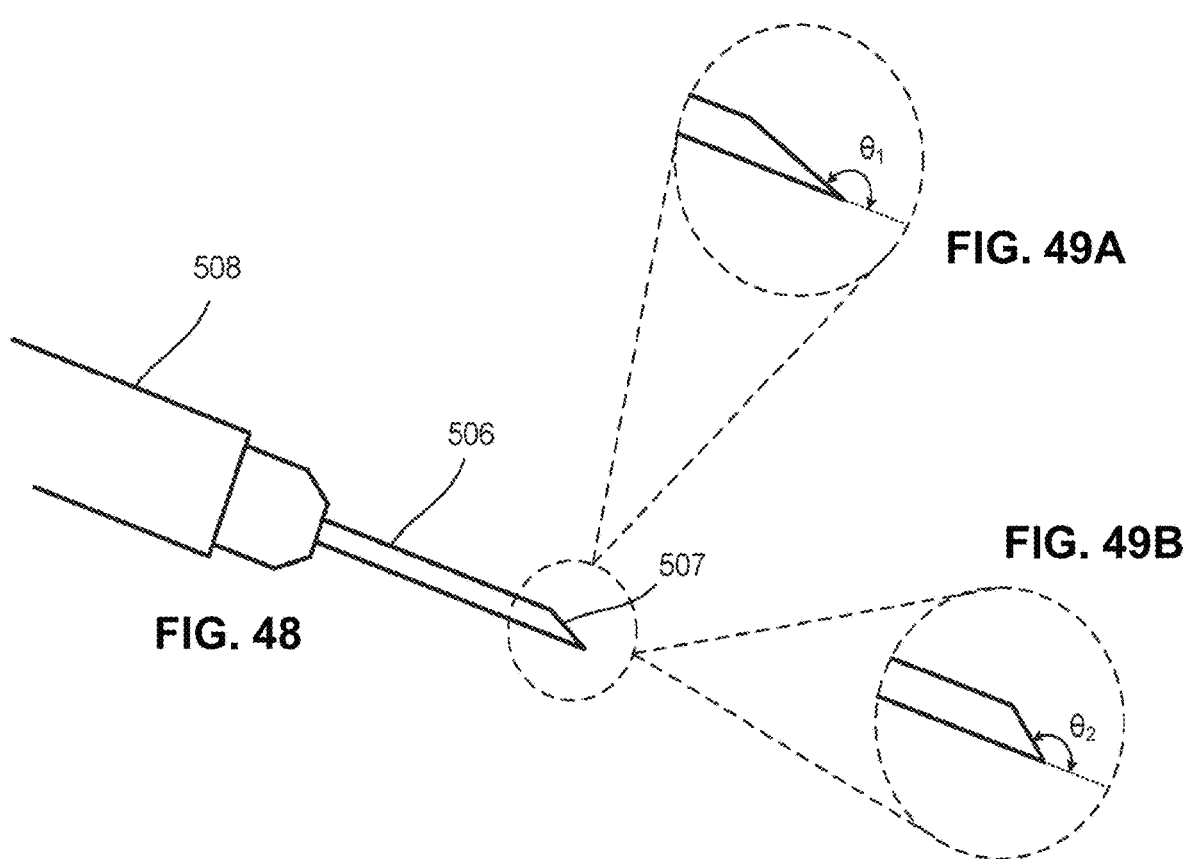
FIG. 48
FIG. 49A
FIG. 49B

SYSTEMS AND METHODS FOR TREATING PATIENTS WITH CLOSED-ANGLE OR NARROW-ANGLE GLAUCOMA USING AN EXCIMER LASER UNIT

BACKGROUND

Glaucoma is a group of eye conditions which result in damage to the optic nerve and lead to vision loss. While glaucoma can occur at any age, it is more common in older adults and is one of the leading causes of blindness for people over the age of 60. Glaucoma may be caused by higher than normal intraocular pressure within an eye, where elevated intraocular pressure can lead to atrophy of the optic nerve, subsequent visual field disturbances, and eventual blindness if left untreated.

SUMMARY

An illustrative method of treating a patient having an eye condition includes determining, during a pre-operative analysis of the patient, that the patient has a risk of developing glaucoma. The method further includes treating the patient with an excimer laser to prophylactically treat glaucoma based on the pre-operative analysis determination that the patient has the risk of developing glaucoma.

In various embodiments, during the pre-operative analysis the patient is diagnosed as having cataracts and has the risk of developing glaucoma.

In various embodiments, the applying of the excimer laser energy to prophylactically treat glaucoma occurs without the patient having been diagnosed with glaucoma.

In various embodiments, the applying of the excimer laser energy to prophylactically treat glaucoma occurs prior to elevated intraocular pressure (TOP) being identified in the eye of the patient.

In various embodiments, the applying of the excimer laser energy to prophylactically treat glaucoma occurs without the patient actually having glaucoma.

In various embodiments, the risk is a congenital risk.

In various embodiments, the congenital risk is associated with a family history, a race, a gender, or a combination thereof of the patient.

In various embodiments, the risk is a presence of a comorbidity.

In various embodiments, the presence of the comorbidity includes ocular hypertension, obesity, diabetes, closed-angled glaucoma, tobacco use, alcohol use, or a combination thereof.

In various embodiments, the risk is an age-related risk.

In various embodiments, the age-related risk includes being at or above age 40, at or above age 45, at or above age 50, at or above age 55, at or above age 60, at or above age 65, at or above age 70, at or above age 75, or at or above age 80.

In various embodiments, the method includes determining, during the pre-operative analysis of the patient, that the patient has cataracts and applying phacoemulsification ultrasound to the patient diagnosed as having the cataracts.

In various embodiments, the phacoemulsification ultrasound and the treating the patient with the excimer laser to prophylactically treat the glaucoma is performed in a same surgical procedure on the patient.

In various embodiments, the phacoemulsification ultrasound and the treating the patient with the excimer laser to prophylactically treat the glaucoma are applied through a same incision in an eye of the patient In various embodiments, the method includes administering anesthesia to the patient before applying the phacoemulsification ultrasound and the excimer laser.

In various embodiments, treating the patient with the excimer laser includes applying shots of pulsed energy from the excimer laser.

An illustrative method of treating a patient having an eye condition includes determining, during a pre-operative analysis of the patient, that the patient has a risk of developing glaucoma. The method further includes applying, through an incision in an eye of the patient, phacoemulsification ultrasound to the patient, the patient having been diagnosed as having cataracts in the eye. The method further includes applying, through the incision in the eye, an excimer laser energy to prophylactically treat glaucoma based on the pre-operative analysis determination that the patient has the risk of developing glaucoma.

In various embodiments, the risk is a congenital risk associated with a family history, a race, a gender, or a combination thereof of the patient.

In various embodiments, the risk is an age-related risk or a presence of a comorbidity.

An illustrative apparatus for delivering laser energy to a surface of a trabecular meshwork of an eye includes an excimer laser source and a probe configured to connect to the excimer laser source. The apparatus further includes a delivery tip connected to the probe. The probe is configured to insert into the eye of a subject that does not have glaucoma. The subject has been determined to be at risk of developing glaucoma during a pre-operative analysis of the subject. The probe is further configured to deliver shots from the excimer laser source to create perforations in the trabecular meshwork.

An illustrative method of treating a patient having an eye condition includes determining that the patient has a closed-angle or narrow-angle glaucoma. The method further includes treating the closed-angle or narrow-angle glaucoma during a surgical procedure performed on the patient. The method further includes, during the surgical procedure, treating the patient with an excimer laser to create a plurality of perforations in the trabecular meshwork by applying a plurality of shots to the trabecular meshwork from the excimer laser.

In various embodiments, the treating the closed-angle or narrow-angle glaucoma includes applying phacoemulsification ultrasound to the patient.

In various embodiments, the phacoemulsification ultrasound includes breaking up a lens of the eye.

In various embodiments, the method includes, after breaking up the lens, removing the lens from the eye of the patient.

In various embodiments, the method includes, after removing the lens, replacing the lens of the eye with an artificial lens.

In various embodiments, the artificial lens is thinner than the lens of the eye that is removed from the eye.

In various embodiments, the artificial lens provides a path for fluid drainage between the artificial lens and an iris of the eye.

In various embodiments, the closed-angle or narrow-angle glaucoma causes at least partial blockage of fluid flow from an anterior chamber of the eye located between a cornea of the eye and a lens of the eye through the trabecular meshwork due to bulging of an iris of the eye.

In various embodiments, the treating of the closed-angle or narrow-angle glaucoma causes the bulging of the iris to decrease.

In various embodiments, the treating of the patient with the excimer laser occurs after the bulging of the iris decreases.

In various embodiments, the treating of the patient with the excimer laser includes inserting an excimer laser probe into an incision of the eye of the patient.

In various embodiments, the treating the closed-angle or narrow-angle glaucoma includes inserting a phacoemulsification ultrasound probe into the incision of the eye of the patient.

In various embodiments, the incision has a length of about one eighth of an inch or smaller.

In various embodiments, the plurality of shots includes at least ten shots.

In various embodiments, the method further includes administering anesthesia to the patient before the treating of the closed-angle or narrow-angle glaucoma and before the treating of the patient with the excimer laser.

In various embodiments, the excimer laser includes a xenon chloride laser source.

An illustrative method of treating a patient having an eye condition includes determining that the patient has a closed-angle or narrow-angle glaucoma. The method further includes applying a phacoemulsification ultrasound to the patient to treat the closed-angle or narrow-angle glaucoma during a surgical procedure performed on the patient. The phacoemulsification ultrasound is applied via a phacoemulsification probe inserted through an incision in an eye of the patient. The method further includes, during the surgical procedure, treating the patient with an excimer laser to create a plurality of perforations in the trabecular meshwork by applying a plurality of shots to the trabecular meshwork from the excimer laser. The plurality of shots is applied via an excimer laser probe inserted through the incision.

In various embodiments, the phacoemulsification ultrasound includes breaking up a lens of the eye.

In various embodiments, the treating the patient with the excimer laser occurs after applying the phacoemulsification ultrasound.

An illustrative apparatus for delivering laser energy to a surface of a trabecular meshwork of an eye includes an excimer laser source and a probe configured to connect to the excimer laser source. The apparatus further includes a delivery tip connected to the probe. The probe is configured to insert into the eye of a subject having a closed-angle or narrow-angle glaucoma. The probe is further configured to insert into the eye after a treatment of the closed-angle or narrow-angle glaucoma is performed on the subject. The probe is further configured to deliver shots from the excimer laser source to create perforations in the trabecular meshwork.

An illustrative apparatus for treating an eye includes a housing, an excimer laser source within the housing, an ultrasound generator within the housing, an irrigation source within the housing, and an aspiration source within the housing.

In various embodiments, the housing is a single housing.

In various embodiments, the apparatus further includes wheels attached to the housing such that the apparatus is movable.

In various embodiments, the apparatus further includes two foot pedals or the housing includes two receptacles each configured to receive a connector for a foot pedal.

In various embodiments, the excimer laser source is controllable using a first foot pedal of the two foot pedals.

In various embodiments, at least one of the ultrasound generator, the irrigation source, or the aspiration source is controllable using a second foot pedal of the two foot pedals.

In various embodiments, the apparatus further includes a single power cord connected to the housing and connectable to a wall outlet.

In various embodiments, each of the excimer laser source, the ultrasound generator, the irrigation source, and the aspiration source are powered via the single power cord.

In various embodiments, the apparatus further includes a port for connecting an excimer laser probe to the housing.

In various embodiments, the port is a first port, and wherein the apparatus further comprises a second port for connecting a phacoemulsification probe to the housing.

In various embodiments, the ultrasound generator, the irrigation source, and the aspiration source are together configured for use with the phacoemulsification probe to perform a phacoemulsification ultrasound on an eye of a subject.

In various embodiments, the excimer laser source is configured for use with the excimer laser probe to perform an excimer laser trabeculostomy (ELT) procedure on the eye of the subject.

In various embodiments, the apparatus further includes a display on the housing.

In various embodiments, the apparatus further includes an energy monitor port on the housing.

In various embodiments, the energy monitor port is configured to receive a first distal end of a phacoemulsification probe and is configured to receive a second distal end of an excimer laser probe.

In various embodiments, the apparatus further includes a sensor in the energy monitor port configured to receive light emitted by the phacoemulsification probe and the excimer laser probe to calibrate power being emitted by the phacoemulsification probe and the excimer laser probe, respectively.

An illustrative apparatus for treating an eye includes a housing and an excimer laser source within the housing configured to perform an excimer laser trabeculostomy (ELT). The apparatus further includes components configured to perform a phacoemulsification ultrasound including, an ultrasound generator within the housing, an irrigation source within the housing, and an aspiration source within the housing.

In various embodiments, the apparatus further includes a single power cord connected to the housing and connectable to a wall outlet.

In various embodiments, the apparatus further includes a first port for connecting an excimer laser probe to the housing and a second port for connecting a phacoemulsification probe to the housing.

An illustrative method for treating an eye includes performing an excimer laser trabeculostomy (ELT) with an excimer laser source housed in a single housing. The method further includes performing a phacoemulsification ultrasound with components housed in the single housing. The components include an ultrasound generator within the housing, an irrigation source within the housing, and an aspiration source within the housing.

An illustrative method of delivering laser energy to a surface of a trabecular meshwork of an eye includes inserting a probe into the eye and delivering, at multiple locations along the trabecular meshwork, shots of the laser energy via the probe to create a plurality of perforations in the trabecular meshwork. The plurality of perforations form a line or curve that is transverse to a Schlemm's canal in the eye.

In various embodiments, the laser energy is delivered from an excimer laser source.

In various embodiments, the plurality of perforations are created in the trabecular meshwork in order to treat glaucoma.

In various embodiments, at least one of the plurality of perforations in the trabecular meshwork is not aligned with the Schlemm's canal.

In various embodiments, at least one of the plurality of perforations in the trabecular meshwork does not create a fluid connection between the Schlemm's canal and an anterior chamber of the eye located between a cornea of the eye and a lens of the eye.

In various embodiments, at least one of the plurality of perforations in the trabecular meshwork is aligned with the Schlemm's canal.

In various embodiments, at least one of the plurality of perforations in the trabecular meshwork creates a fluid connection between the Schlemm's canal and an anterior chamber of the eye located between a cornea of the eye and a lens of the eye.

In various embodiments, a light source comprising a Gonio lens, endoscope, or other illumination source aids in adjusting placement of the probe.

In various embodiments, the plurality of shots comprises 10 shots per eye.

In various embodiments, the plurality of shots comprises greater than 10 shots per eye.

In various embodiments, each of the plurality of perforations has a diameter of approximately 200 μm.

In various embodiments, the probe is inserted into an incision in the eye.

In various embodiments, the method further includes analyzing effectiveness of the shots by visualizing drainage of aqueous humor and bloody reflux.

In various embodiments, the probe is an optical fiber probe.

In various embodiments, the laser energy is delivered from an excimer laser source comprising a xenon chloride laser.

In various embodiments, the method further includes physically contacting the trabecular meshwork with the probe while delivering the plurality of shots. The plurality of perforations are created while the probe is physically contacting the trabecular meshwork.

An illustrative method of delivering laser energy to a surface of a trabecular meshwork of an eye includes inserting a probe into an eye of a subject having glaucoma and adjusting placement of the probe to a first position proximate to the trabecular meshwork in the eye. The method further includes delivering a first shot from a laser source to create a first perforation in the trabecular meshwork. The method further includes adjusting placement of the probe to a second position proximate to the trabecular meshwork. The method further includes delivering a second shot from the laser source to create a second perforation in the trabecular meshwork. The first perforation and the second perforation form a line that runs transverse to a Schlemm's canal of the eye.

In various embodiments, the method further includes adjusting placement of the probe to subsequent positions proximate to the trabecular meshwork and delivering subsequent shots from the laser source to create subsequent perforations in the trabecular meshwork. The first perforation, the second perforation, and the subsequent perforations form a line or curve that runs transverse to the Schlemm's canal of the eye.

In various embodiments, the laser source includes an excimer laser source.

An illustrative apparatus for delivering laser energy to a surface of a trabecular meshwork of an eye to treat glaucoma includes an excimer laser source and a probe configured to connect to the excimer laser source. The apparatus further includes a delivery tip connected to the probe. The probe is configured to insert into the eye of a subject having the glaucoma, move to a first position proximate to the trabecular meshwork in the eye, deliver a first shot from the excimer laser source to create a first perforation in the trabecular meshwork, move to a second position proximate to the trabecular meshwork, and deliver a second shot from the excimer laser source to create a second perforation in the trabecular meshwork. The first perforation and the second perforation form a line that runs transverse to a Schlemm's canal of the eye.

BRIEF DESCRIPTION OF THE DRAWINGS

FIG. 11 is a flowchart of an embodiment of performing a pre-operative analysis and ELT treatment of a patient.

FIGS. 12A and 12B demonstrate a normal eye and an eye with closed angle glaucoma.

FIG. 29 shows an embodiment of a probe for use with the excimer laser system.

FIG. 30 shows a cross-sectional view of the probe taken along line A-A of FIG. 4.

FIG. 31 shows a cross-sectional view of the probe taken along line B-B of FIG. 4.

FIG. 34 is a flowchart of an embodiment for authenticating a probe for use with an excimer laser unit.

FIG. 35 is a flowchart of an embodiment for preventing use of an unauthenticated probe. with an excimer laser unit.

FIG. 46 shows a cross-sectional view of the probe taken along line A-A of FIG. 6.

FIG. 47 shows a cross-sectional view of the probe taken along line B-B of FIG. 6.

FIG. 48 shows an enlarged view of a distal portion of a probe.

FIGS. 49A and 49B show enlarged views of delivery tips of a probe having different bevel angles.

DETAILED DESCRIPTION

A major risk factor in glaucoma is ocular hypertension, in which intraocular pressure is higher than normal. An elevated intraocular pressure can lead to atrophy of the optic nerve, subsequent visual field disturbances, and eventual blindness if left untreated.

Intraocular pressure is a function of the production of aqueous humor fluid by the ciliary processes of the eye and its drainage through a tissue called the trabecular meshwork. The trabecular meshwork is an area of tissue in the eye located around the base of the cornea and is responsible for draining the aqueous humor into a lymphatic-like vessel in the eye called Schlemm's canal, which subsequently delivers the drained aqueous humor into the bloodstream. Proper flow and drainage of the aqueous humor through the trabecular meshwork keeps the pressure inside the eye normally balanced. In open-angle glaucoma, the most common type of glaucoma, degeneration or obstruction of the trabecular meshwork can result in slowing or completely preventing the drainage of aqueous humor, causing a buildup of fluid, which increases the intraocular pressure. Under the strain of this pressure, the optic nerve fibers become damaged and may eventually die, resulting in permanent vision loss.

If treated early, it is possible to slow or stop the progression of glaucoma. Depending on the type of glaucoma, treatment options may include eye drops, oral medications, surgery, laser treatment, or a combination of any of these. For example, treatment of open-angle glaucoma may include surgical treatments, such as filtering surgery, in which an opening is created in the sclera of the eye and a portion of the trabecular meshwork is removed, and surgical implantation of stents or implants (i.e., drainage tubes), in which a small tube shunt is positioned within the eye to assist in fluid drainage. However, such treatments are highly invasive and may present many complications, including leaks, infections, hypotony (e.g., low eye pressure), and require post-operative, long-term monitoring to avoid late complications.

More recently, minimally invasive laser treatments have been used to treat glaucoma. In such treatments, the surgeon uses a laser to thermally modify and/or to puncture completely through various structures, including the trabecular meshwork and/or Schlemm's canal. For example, a laser trabeculostomy is a procedure in which a surgeon guides a working end of a laser fiber through a corneal incision of the eye and towards the trabecular meshwork and applies laser energy to destroy portions of the meshwork to create channels in the meshwork which allow aqueous humor to flow more freely into the Schlemm's canal.

Figure 1:
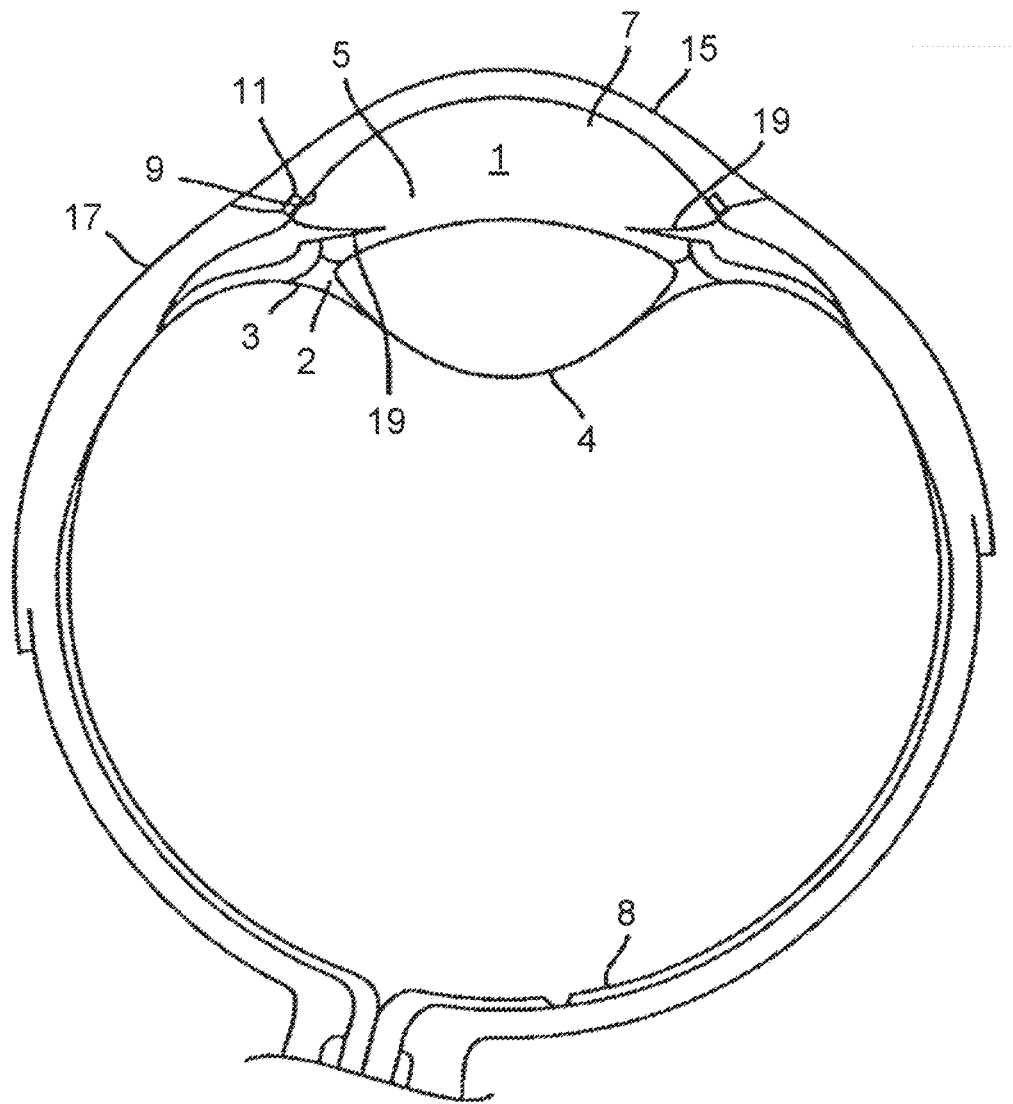
FIG. 1 is schematic sectional view of an eye illustrating the interior anatomical structure.

In order to fully appreciate the various embodiments described herein, a brief overview of the anatomy of the eye is provided. FIG. 1 is schematic sectional view of an eye illustrating the interior anatomical structure. As shown, the outer layer of the eye includes a sclera 17 that serves as a supporting framework for the eye. The front of the sclera includes a cornea 15, a transparent tissue that enables light to enter the eye. An anterior chamber 7 is located between the cornea 15 and a crystalline lens 4. The anterior chamber 7 contains a constantly flowing clear fluid called aqueous humor 1. The crystalline lens 4 is connected to the eye by fiber zonules, which are connected to the ciliary body 3. In the anterior chamber 7, an iris 19 encircles the outer perimeter of the lens 4 and includes a pupil 5 at its center. The pupil 5 controls the amount of light passing through the lens 4. A posterior chamber 2 is located between the crystalline lens 4 and the retina 8.

Figure 2:
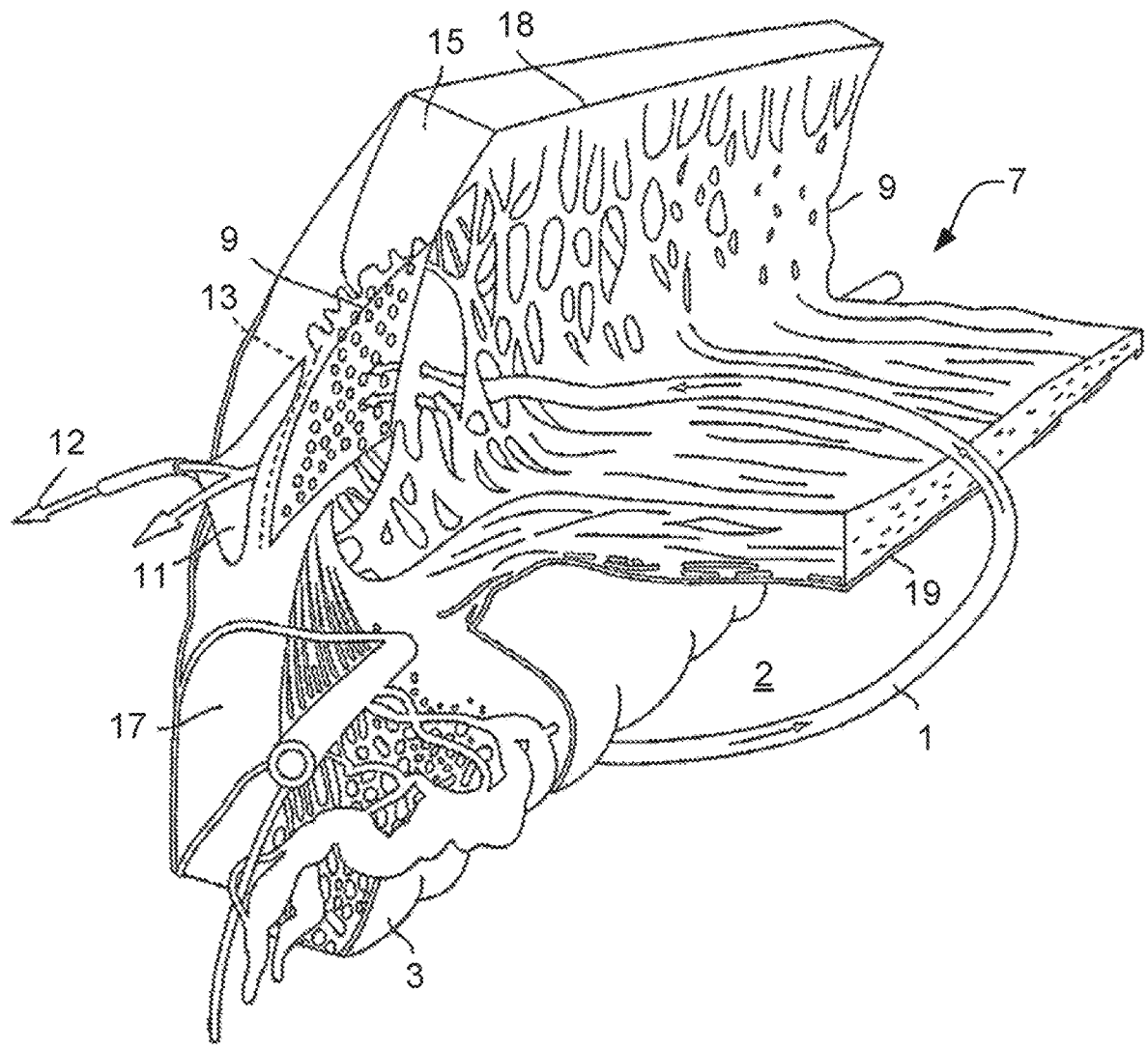
FIG. 2 is a perspective fragmentary view of the anatomy within the anterior chamber of an eye depicting the corneo-scleral angle.

FIG. 2 is a perspective fragmentary view of the anatomy within the anterior chamber of an eye depicting the corneoscleral angle. As shown, the anatomy of the eye further includes a trabecular meshwork 9, which is a narrow band of spongy tissue that encircles the iris 19 within the eye. The trabecular meshwork has a variable shape and is microscopic in size. It is of a triangular cross-section and of varying thickness in the range of 100-200 microns. It is made up of different fibrous layers having micron-sized pores forming fluid pathways for the egress of aqueous humor. The trabecular meshwork 9 has been measured to about a thickness of about 100 microns at its anterior edge, Schwalbe's line 18, which is at the approximate juncture of the cornea 15 and sclera 17.

The trabecular meshwork widens to about 200 microns at its base where it and iris 19 attach to the scleral spur. The passageways through the pores in trabecular meshwork 9 lead through very thin, porous tissue called the juxtacanalicular trabecular meshwork 13 that in turn abuts the interior side of a structure called Schlemm's canal 11. Schlemm's canal 11 is filled with a mixture of aqueous humor and blood components and branches off into collector channels 12 which drain the aqueous humor into the venous system. Because aqueous humor is constantly produced by the eye, any obstruction in the trabecular meshwork, the juxtacanalicular trabecular meshwork or in Schlemm's canal prevents the aqueous humor from readily escaping from the anterior eye chamber which results in an elevation of intraocular pressure within the eye.

The eye has a drainage system for the draining aqueous humor 1 located in the corneoscleral angle. In general, the ciliary body 3 produces the aqueous humor 1. This aqueous humor flows from the posterior chamber 2 through the pupil 5 into the anterior chamber 7 to the trabecular meshwork 9 and into Schlemm's canal 11 to collector channels 12 to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork 13, which is located between the trabecular meshwork 9 and Schlemm's canal 11, more specifically, the inner wall of Schlemm's canal. It is desirable to correct this outflow obstruction by enhancing the eye's ability to use the inherent drainage system.

When an obstruction develops, for example, at the juxtacanalicular trabecular meshwork 13, intraocular pressure gradually increases over time, thereby leading to damage and atrophy of the optic nerve, subsequent visual field disturbances, and eventual blindness if left untreated. The laser probe of the present embodiments is well suited for use in treating glaucoma. In particular, as will be described in greater detail herein, the laser probe is configured to be coupled to a laser source and transmit laser energy from the laser source to the trabecular meshwork 13, resulting in photoablation of tissue (including at least the trabecular meshwork 13 and, in some instances, the Schlemm's canal 11) for the creation of channels in the meshwork (and potentially Schlemm's canal 11, thereby improving fluid drainage into the Schlemm's canal 11 and reducing intraocular pressure in the eye.

Figure 3:
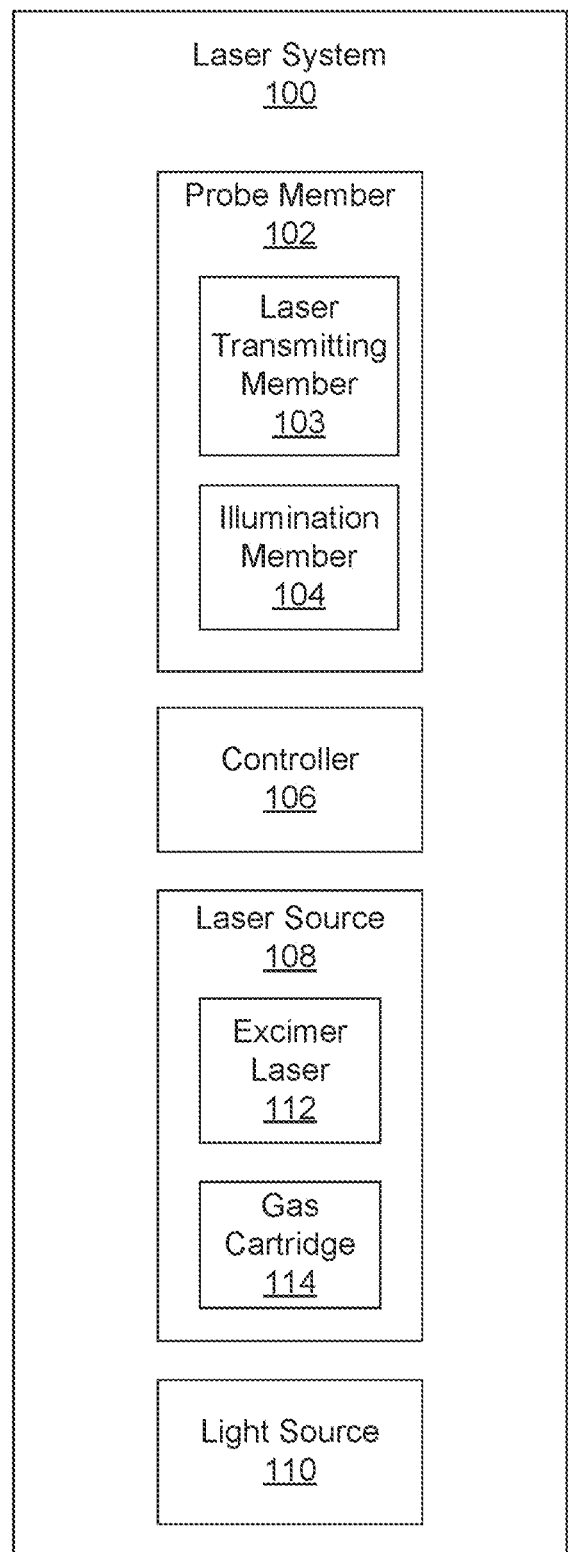
FIG. 3 diagrams an excimer laser system of the present disclosure.

FIG. 3 diagrams an excimer laser system 100 of the present disclosure. The system 100 includes a probe member 102, which includes a laser transmitting member 103 and an illumination member 104, a controller 106, a laser source 108, and a light source 110. As will be described in greater detail herein, many of the components of the laser system 100 may be contained in a housing, such as a moveable platform, to be provided in a setting in which the procedure is to be performed (e.g., operating room, procedure room, outpatient office setting, etc.) and the probe member 102 may connect to the housing for use during treatment. Upon coupling the probe member 102 to the housing, the laser transmitting member 103 and illumination member 104 are each coupled to the respective laser source 108 and light source 110. The controller 106 provides an operator (i.e., surgeon or other medical professional) with control over the output of laser signals (from the laser source 108 to the laser transmitting member 103) and, in turn, control over the transmission of laser energy from the laser transmitting member 103 of the probe 102. The controller 106 further provides the operator with control over the output of light signals (from the light source 110 to the illumination member 104) and, in turn, control over the emission of light from the illumination member 104.

The controller 106 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 106 may include a hardware processor coupled to non-transitory, computer-readable memory containing instructions executable by the processor to cause the controller to carry out various functions of the laser system 100 as described herein, including controller laser and/or illumination output.

The laser source 108 may include an excimer laser 112 and a gas cartridge 114 for providing the appropriate gas combination to the laser 112. The excimer laser 112 is a form of ultraviolet laser that generally operates in the UV spectral region and generates nanosecond pulses. The excimer gain medium (i.e., the medium contained within the gas cartridge 114) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 112 of the present system 100 is an XeCl excimer laser and emits a wavelength of 308 nm.

The light source 110 provides a light signal to the illumination member 104 within the visible light spectrum. Accordingly, the illumination source 110 may include, but is not limited to, an incandescent light source, a fluorescent light source, a halogen light source, a high-intensity discharge light source, a metal halide light source, and a light emitting diode (LED) light source.

Figure 4:
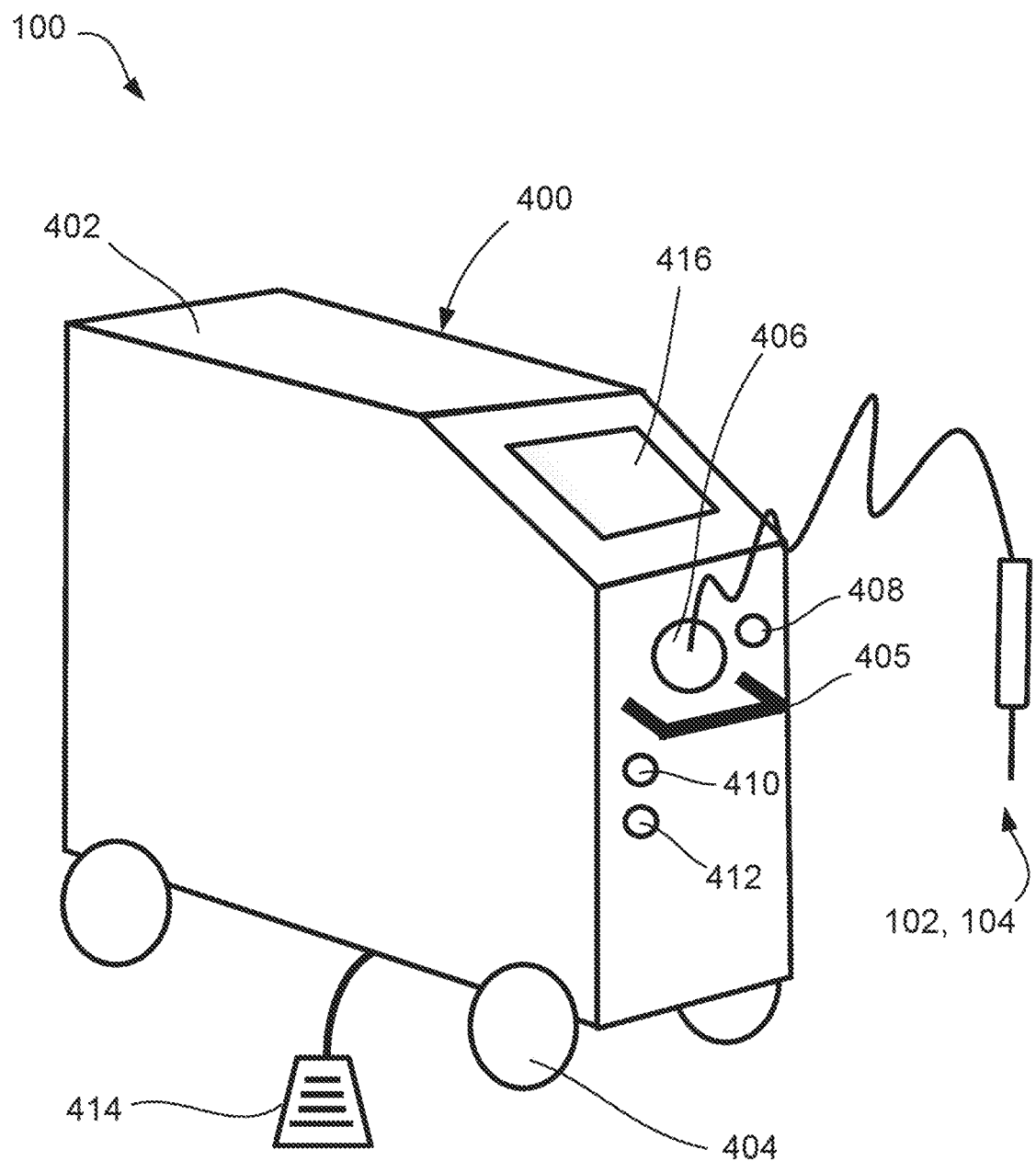
FIG. 4 shows an embodiment an excimer laser system.

FIG. 4 shows an embodiment an excimer laser system 100 provided in an instrument 400. As previously described, one or more components of the system 100 can be contained within the instrument 400. In the present embodiment, the controller 106, the laser source 108 (including the excimer laser 112 and gas cartridge 114), and the light source 110 are contained within a housing 402. The housing 402 has wheels 404 and is portable. The instrument 400 further includes a push-pull handle 405 which assists with portability of the instrument 400. The instrument 400 further includes a connection port 406 for receiving a connecting end of the probe member 102 to establish a connection between the laser transmitting member 103 and illumination member 104 and the respective laser source 108 and light source 110. The instrument 400 further includes various inputs for the operator, such as a fiber probe cap holder 408, an emergency stop button 410, and a power switch 412. The instrument 400 further includes a foot pedal 414 extending from the housing 402 and is operable to provide control over the delivery of shots from the excimer laser 412 to the laser transmitting member 103 of the probe 102. The instrument 400 further includes a display 416, which may be in the form of an interactive user interface. In some examples, the interactive user interface 410 displays patient information, machine settings, and procedure information.

Figure 5:
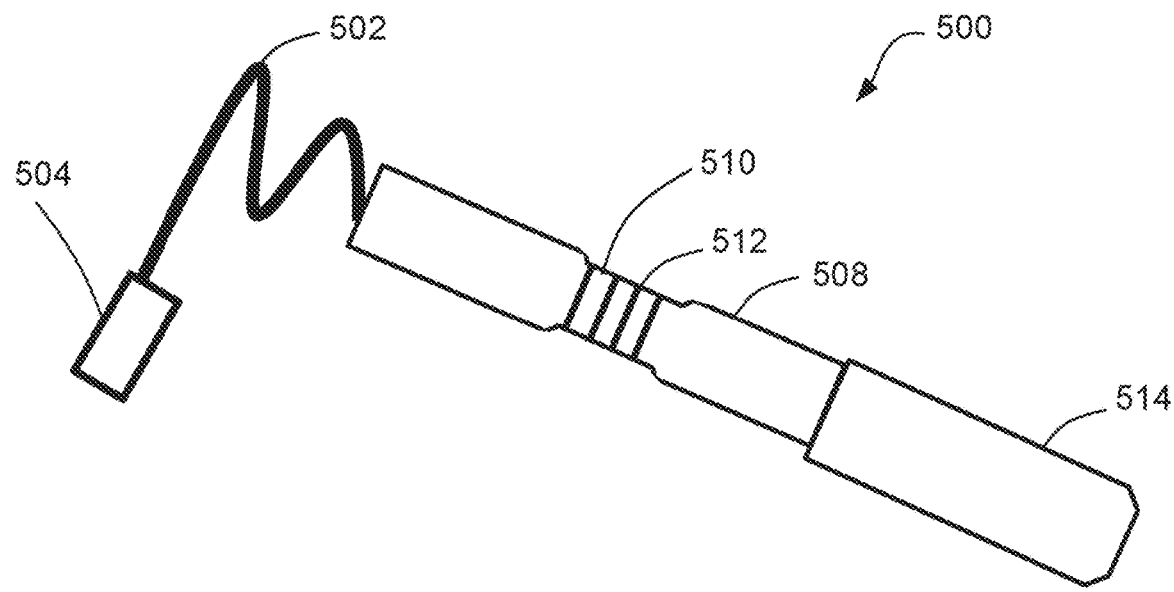
FIG. 5 shows an embodiment of a probe for use with the excimer laser system.
Figure 6:
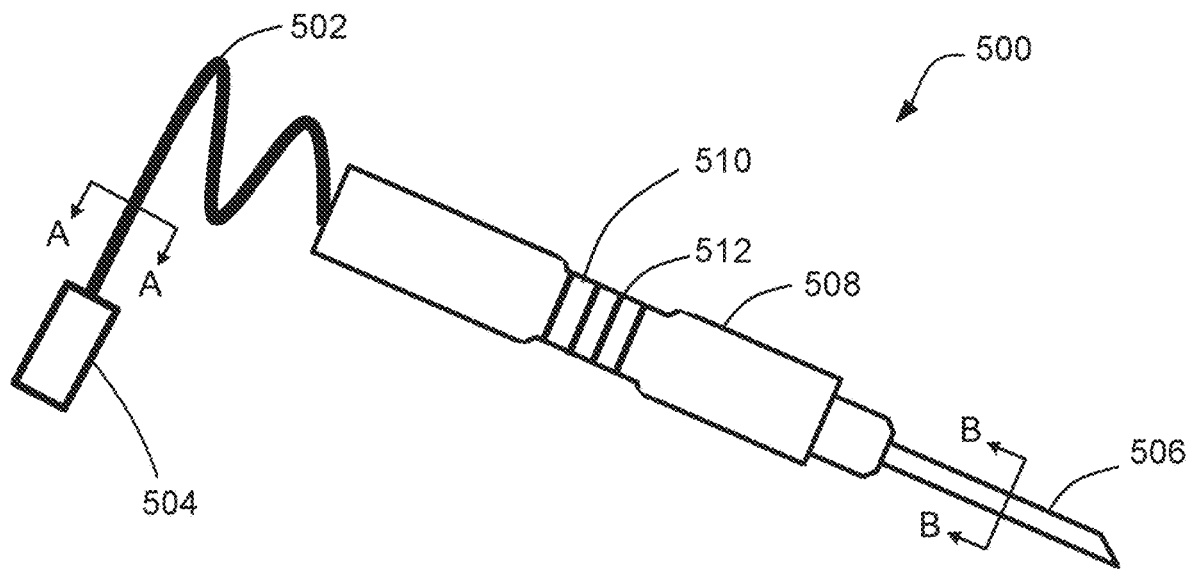
FIG. 6 shows an embodiment of a probe for use with the excimer laser system.

FIG. 5 shows an embodiment of a probe 500 for use with the excimer laser system 100, illustrating the probe 500 having a capped, distal delivery tip 506. FIG. 6 shows an embodiment of the probe 500 with the cap 514 removed, exposing the delivery tip 506 of the probe 500. The probe 500 is a single use, disposable unit. The probe 500 generally includes a laser transmitting member and an illumination member as previously described herein, wherein each are coupled to their respective sources (i.e., laser source 108 and light source 110) by way of a connector 502 (elongated cord) extending from the body of the probe 500 and having a connection assembly 504 configured to be received within the connection port 406 of the instrument 400. The probe 500 further includes a delivery tip 506 from which laser energy (from the laser transmitting member) and visible light (from the illumination member) may be emitted. The probe 500 includes a handheld body 508, which may include a finger grip 510 with ridges or depressions 512. The body 508 of the handheld probe 500 may be metal or plastic.

Figure 7:
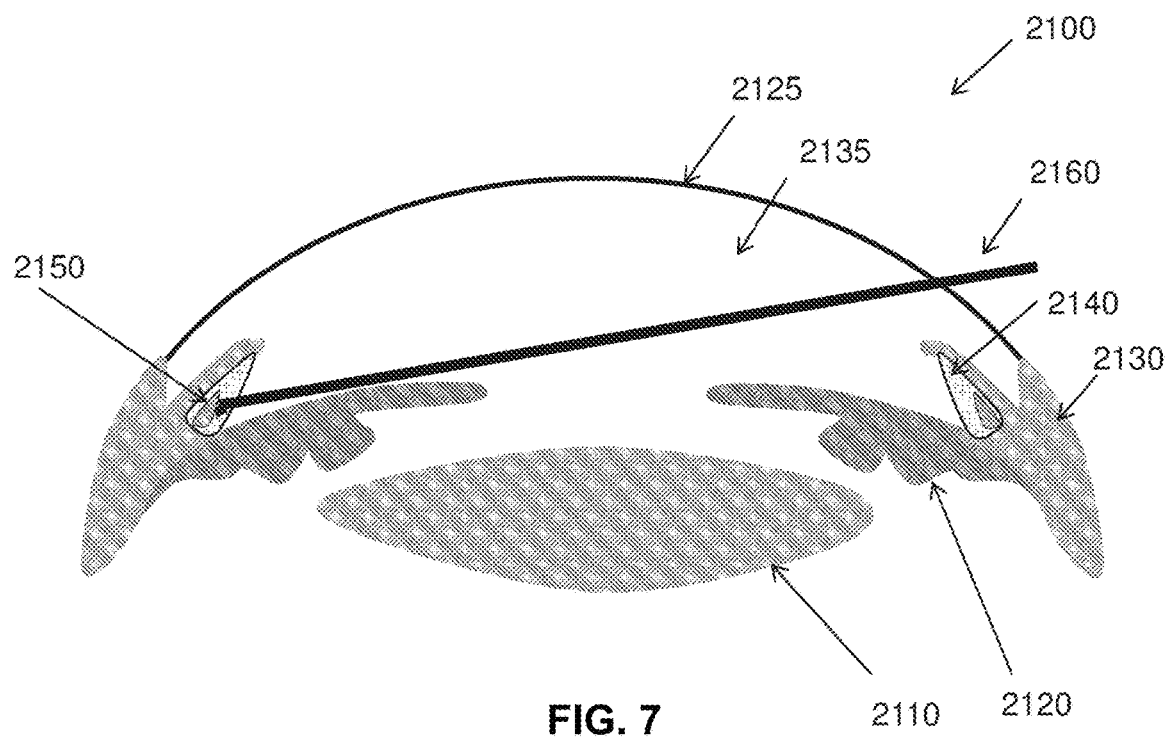
FIG. 7 is a schematic sectional view of an embodiment in an eye.
Figure 8:
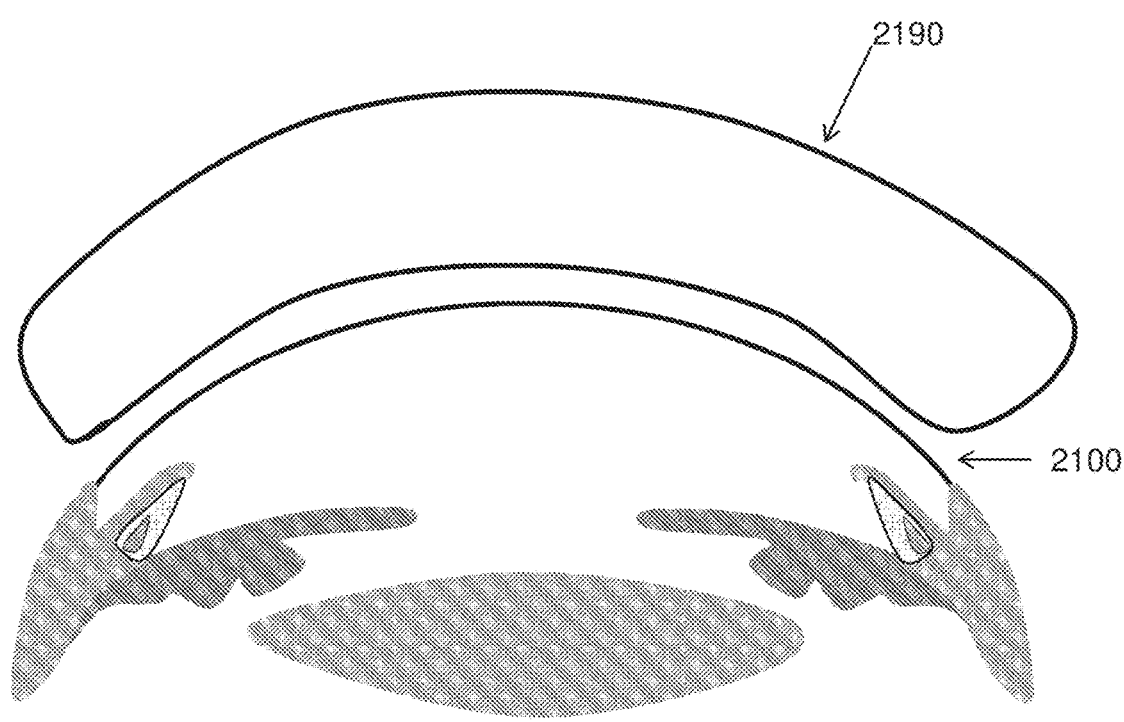
FIG. 8 shows the schematic section view of an eye with a light source aid.
Figure 9:
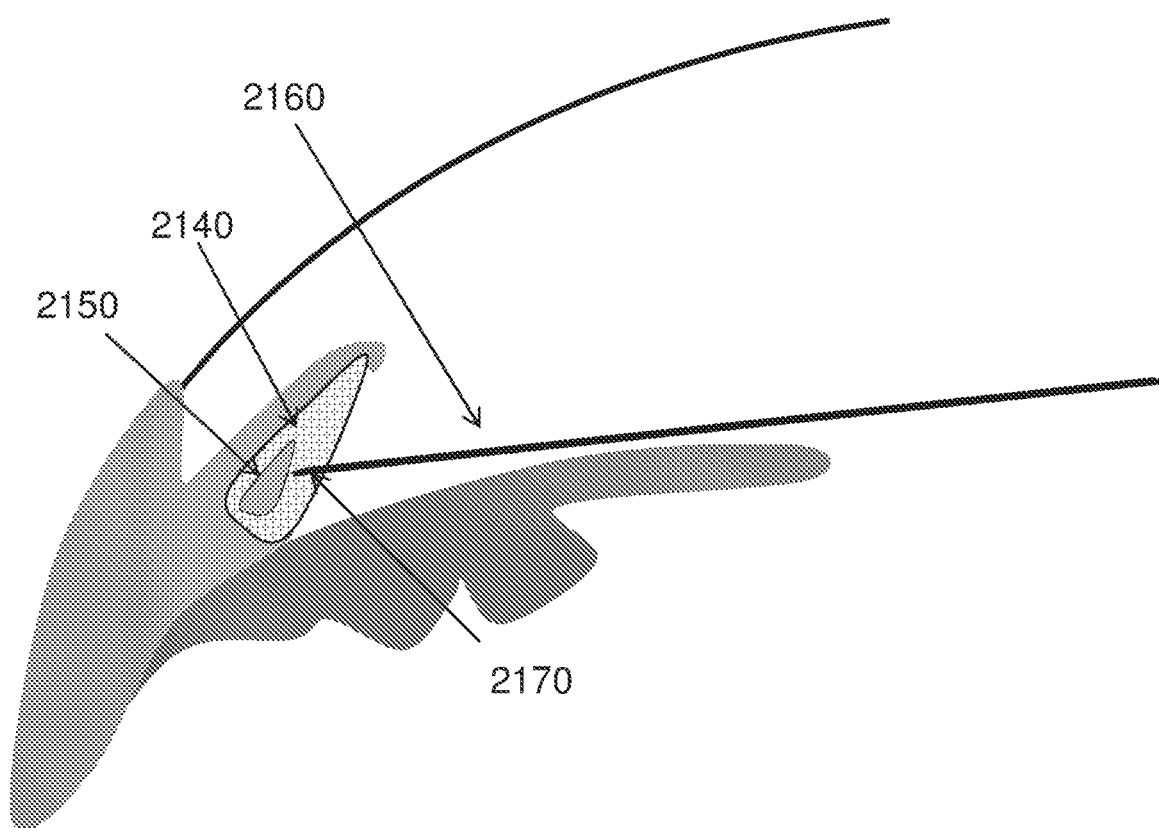
FIG. 9 is an enlarged schematic sectional view of an embodiment.

FIG. 7 is schematic sectional view of an eye 2100 illustrating the interior anatomical structure. FIG. 8 shows the schematic section view of an eye 2100 with a light source 2190, such as a Gonio lens, endoscope, or other light source. FIG. 9 is an enlarged schematic sectional view of the eye. The outer layer, or sclera, 2130 serves as a supporting framework for the eye, and the front of the outer layer 2130 includes a cornea 2125, a transparent tissue that enables light to enter the eye. An anterior chamber 2135 is located between the cornea 2125 and a crystalline lens 2110, and a posterior chamber is located behind the lens 2110. The anterior chamber 2135 contains a constantly flowing clear fluid called aqueous humor. In the anterior chamber 2135, an iris 2120 encircles the outer perimeter of the lens 2110 and includes a pupil at its center, which controls the amount of light passing through the lens 2110.

The eye further includes a trabecular meshwork 2140, which is a narrow band of spongy tissue that encircles the iris 2120 within the eye. The trabecular meshwork has a variable shape and is microscopic in size. It is of a triangular cross-section and of varying thickness in the range of 100-200 microns. It is made up of different fibrous layers having micron-sized pores forming fluid pathways for the egress of aqueous humor. The trabecular meshwork 2140 has been measured to about a thickness of about 100 microns at its anterior edge, known as Schwalbe's line, which is at the approximate juncture of the cornea and sclera.

The trabecular meshwork widens to about 200 microns at its base where it and iris 2120 attach to the scleral spur. The passageways through the pores in trabecular meshwork 2140 lead through very thin, porous tissue called the juxtacanalicular trabecular meshwork that abuts the interior side of a structure called Schlemm's canal 2150. Schlemm's canal 2150 is filled with a mixture of aqueous humor and blood components and branches off into collector channels which drain the aqueous humor into the venous system. Because aqueous humor is constantly produced by the eye, any obstruction in the trabecular meshwork, the juxtacanalicular trabecular meshwork or in Schlemm's canal prevents the aqueous humor from readily escaping from the anterior eye chamber which results in an elevation of intraocular pressure within the eye.

The eye has a drainage system for the draining aqueous humor. The aqueous humor flows from a posterior chamber behind the lens 2110 through the pupil into the anterior chamber 2135 to the trabecular meshwork 2140 and into Schlemm's canal 2150 to collector channels and then to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork located between the trabecular meshwork 2140 and Schlemm's canal 2150, more specifically, the inner wall of Schlemm's canal. When an obstruction develops, such as at the juxtacanalicular trabecular meshwork or at Schlemm's canal, intraocular pressure gradually increases over time, leading to damage and atrophy of the optic nerve, subsequent visual field disturbances, and eventual blindness if left untreated.

A laser probe according to various embodiments is used to treat glaucoma. The delivery tip of the laser probe 2160 is guided through a small incision, typically about ⅛ inch or smaller, in the cornea 2125 of the eye and across the anterior chamber 2135 to a position proximate to the Schlemm's canal 2150. The probe is guided very flat through the anterior chamber to avoid perforating the cornea in the visual field. The laser probe is coupled to a laser source and transmits laser energy from the laser source to the trabecular meshwork 2140 and Schlemm's canal 2150, resulting in photoablation of tissue including at least the trabecular meshwork 2140 and, in some instances, the Schlemm's canal 2150. The photoablation from the laser energy creates perforations in the meshwork and Schlemm's canal, thereby improving fluid drainage into the Schlemm's canal 2150 and reducing intraocular pressure in the eye.

FIG. 9 shows the arrangement of the delivery tip 2160 at a position proximate 2170 to the Schlemm's canal 2150. Arrangement of the laser at a proximate position to the Schlemm's canal allows the laser path to travel crosswise through the trabecular meshwork to the Schlemm's canal. By positioning the laser proximate to the Schlemm's canal, the laser is able to provide photoablation to a greater amount of surface area of the trabecular meshwork in comparison to a laser arranged at positions perpendicular or parallel to the Schlemm's canal. Moreover, if the delivery tip of the laser was positioned parallel to the Schlemm's canal, the laser would not provide photoablation to any surface area of the trabecular meshwork or Schlemm's canal.

ELT Treatment Based on Risk Factors and Combination Treatments Using Phaco and ELT Many people suffer vision loss due to cataracts or glaucoma. Cataracts are a common condition that occurs when light is blocked from entering the eye due to cloudiness or opacity in the lens of the eye. Patients suffering from glaucoma experience vision loss caused by damage to the optic nerve due to buildup of fluid in the anterior chamber of the eye.

The risk of developing cataracts, glaucoma, or both, increases with age; and many people over the age of 60 suffer from both vision-altering conditions. Moreover, patients diagnosed with cataracts at a young age have a higher risk of developing glaucoma later in life. Patients diagnosed with either condition undergo treatment ranging from medication to surgery.

The various embodiments provide systems and methods for prophylactic treatment of glaucoma in patients being treated for cataracts. According to various embodiments, a patient who presents for cataracts removal is evaluated and, if appropriate, prophylactically treated to prevent glaucoma. The various embodiments take advantage of the insight that certain patients with cataracts, especially at a younger age, are likely to develop glaucoma later in life, may be in the early stages of developing glaucoma, or may be at high risk for developing glaucoma do to family history, racial background, underlying medical conditions, or other factors. The various embodiments include evaluating cataracts patients to determine whether an additional procedure as describe below would be beneficial to prevent the onset of glaucoma. Accordingly, methods of the various embodiments comprise selecting patients being treated for cataracts for prophylactic treatment of glaucoma. It should be noted that, while an excimer laser trabeculostomy (ELT) procedure is the preferable prophylactic glaucoma treatment in accordance with the various embodiments herein, other procedures known in the art may be used for prophylactic glaucoma treatment.

In various embodiments described herein an ELT procedure may be performed prophylactically with or without performing the other types of treatment described herein, such as the phacoemulsification treatments described below. As such, the ELT procedure may be performed based on a diagnosis of a patient that they are at high risk for developing glaucoma or have a congenital or other risk factor for developing glaucoma as described herein.

Phacoemulsification treatment (also referred to herein as "phaco") is a common method for removal of cataracts. Various embodiments comprise administering phaco and ELT during the same surgical visit, thereby minimizing the amount of surgeries for a patient having multiple eye conditions. Because phaco and ELT are less invasive than traditional surgeries, the amount of recovery time for the patient is minimized. In fact, both phaco and ELT are performed through one small incision made within a patient's eye. In various embodiments, a laserphaco procedure may be used in lieu of a phacoemulsification treatment. In such embodiments, a laserphaco machine and/or a combined ELT/laserphaco machine may be used in accordance with the various embodiments herein in the same way a phacoemulsification and/or a combined ELT/phacoemulsification machine may be used. In various embodiments however, regardless of what type of machine is used (stand-alone ELT or combined ELT/phaco machine), an ELT procedure may alone be performed (without a cataracts treatment such as phaco), for example to treat glaucoma and/or to prophylactically treat glaucoma as described herein.

Any cataracts treatment suffices for use in various embodiments. Phacoemulsification is a preferred cataracts treatment in which a small incision is made in the peripheral cornea and an ultrasonic probe is inserted. The incision is long enough to allow entry of the ultrasonic probe and additional instruments used for removal of the cataract. Typically, the incision is about ⅛ inch long. The ultrasonic probe breaks the cataract into small pieces which are then removed from the eye. The ultrasonic probe typically has a titanium or steel needle that vibrates at ultrasonic frequency to emulsify the cataract while a pump aspirates particles through the tip of the needle. To facilitate removal, the physician may use a chipping tool and an irrigator. A clear replacement intraocular lens (IOL) is then inserted through the incision.

Before closing the incision, methods of the various embodiments allow for the performance of an excimer laser trabeculostomy for prophylactic treatment of glaucoma. In various embodiments, an excimer laser may be used to create perforations in the Schlemm's canal and/or the trabecular meshwork of the eye, thereby allowing drainage of fluid from the eye. ELT treats open-angle glaucoma at the site of occurrence by increasing the permeability of the trabecular meshwork. During ELT, the laser creates a direct connection between the front chamber of the eye and the Schlemm's canal by using a fiber probe in physical contact with the trabecular meshwork. The fiber probe comprises an optical fiber suitable for UV light that is embedded into a handheld laser applicator. In some examples, a FIDO LASER APPLICATOR manufactured by MLase AG is used as the fiber probe.

The ELT procedure comprises guiding a laser light to the trabecular meshwork in the iridocorneal angle via a small corneal incision. A goniolens may be used to achieve effective, precise positioning of an end of the fiber probe at the trabecular meshwork to create a passageway into Schlemm's canal. A physician uses the goniolens to intraoperatively observe quality criteria, including reflux hemorrhage and minor reflux bleeding.

To achieve easier drainage of the aqueous humor in order to reduce IOP, a total of about ten ELT sites or perforations, each included a diameter of approximately 200 µm, are lasered into the trabecular meshwork and/or Schlemm's canal by way of laser ablation or photoablation. In comparison, stents and implants have smaller individual diameters that are between about 80 µm to about 120 µm. The photoablative excimer laser operates at a wavelength of 308 nm. In some examples, the excimer laser is an encapsulated xenon chloride (XeCl) excimer laser such as the EX TRA LASER manufactured by MLase AG. Because ELT is a non-thermal procedure, tissue reactions in the trabecular meshwork are not shown or activated post-operatively. The lack of heat generation in ELT allows for a nearly absent activation of postoperative tissue reactions and provides long-term stability of the pressure-reducing effects. Moreover, unlike the traditional glaucoma treatment method of shunt or stent placement, the stability of Schlemm's canal using ELT treatment remains unchanged.

Methods of the various embodiments comprise treating a subject having one or more eye conditions and providing ELT as preventative treatment. Phacoemulsification ultrasound is applied to a subject having one or more eye conditions, and an excimer laser is applied to an eye of the subject to increase blood flow to an eye of the subject. Applying an excimer laser to the eye comprises applying shots of pulsed energy from the excimer laser. In some examples, about 10 shots of pulsed energy are applied to the eye. In an example, the one or more eye conditions comprise cataracts and glaucoma.

In some cases, applying an excimer laser prophylactically treats glaucoma. Methods of the various embodiments further comprise administering anesthesia to the subject before applying the phacoemulsification ultrasound and the excimer laser. In some embodiments, methods of the various embodiments further comprise post-operative analysis. For example, post-operative analysis comprises observing fluid flowing from Schlemm's canal in the eye.

Systems of the various embodiments are used for treatment of a subject having one or more eye conditions. Systems of the various embodiments are used to treat cataracts and preventatively treat glaucoma during the same surgical visit, thereby eliminating the need for multiple surgeries to treat the two conditions. By preventatively treating glaucoma, irreversible vision loss from glaucoma may be avoided. Systems include a phacoemulsification ultrasound system comprising an ultrasound probe for treating a cataract in an eye of a subject, and an excimer laser system comprising an excimer laser and a fiber probe for increasing blood flow to the eye of the subject. In some examples, increasing blood flow to the eye prophylactically treats glaucoma in the subject.

Moreover, methods of the various embodiments provide treatment for both conditions and can decrease the amount of, or eliminate the need for, medications to manage the eye conditions. In an example, cataract medication is eliminated because phaco is effective in reversing vision loss due to cataracts. In an example, the IOP is lowered by the ELT procedure, and medication to treat glaucoma is reduced or eliminated because eye drops that lower IOP by decreasing the amount of fluid produced or increasing fluid flow output are unnecessary.

In an embodiment, a physician uses systems of the various embodiments to perform phaco for the treatment of cataracts and ELT for the preventative treatment of glaucoma. An interactive user interface displays patient information, machine settings, and procedure information. The physician uses different instruments and probes depending on the treatment procedure. For example, the physician uses an ultrasonic handheld probe for phaco and a fiberoptic probe for ELT. The fiber probe comprises an optical fiber having a tip. In some embodiments, the tip comprises the optical fiber jacketed in stainless steel. In some cases, the tip is beveled. In certain embodiments, the fiber probe is disposable.

The physician is able to keep both hands free for use with the respective probes and other instruments during the procedure by using a foot pedal as the power source for each procedure. In some embodiments, the phacoemulsification ultrasound system further comprises a foot pedal to power application of ultrasound, irrigation, and aspiration to remove the cataract from the eye of the subject. In some embodiments, the excimer laser system further comprises a foot pedal to power the excimer laser and deliver a shot from the excimer laser to the eye of the subject. For example, the foot pedal is used by the physician to provide power to the fiber used for ELT, such as by providing laser shots.

Other instruments used by the physician include a goniolens, a chipping tool, and an irrigator. The user interface provides any suitable information. For instance, the user interface provides settings of the machine, such as number of laser shots administered with each tap of the foot pedal. The user interface displays patient information or procedure information.

In some embodiments, the patient is administered an anesthetic before surgery. In some examples, the anesthesia is topical. In some examples, the anesthesia comprises anesthetic drops. In some instances, general anesthesia is administered to the patient. In an example, the eye is anesthetized first with eye drops and then an injection of anesthetic is administered around the eye to prevent pain and excessive eye movement during surgery.

A method of treating a subject having one or more eye conditions comprises applying phacoemulsification ultrasound to a subject having one or more eye conditions; and applying an excimer laser to the subject to preventatively treat glaucoma. A system for treatment of one or more eye conditions in a subject comprises a phacoemulsification ultrasound system and an excimer laser system. Methods and systems of the various embodiments prophylactically treat glaucoma in the subject. The phaco system comprises an ultrasound probe for treating cataracts in the subject. The excimer laser system comprises an excimer laser and a fiber probe that applies pulsed shots of energy from the excimer laser to the eye.

Various embodiments provide methods and systems for treatment of both cataracts and glaucoma during one surgical procedure. Methods of the various embodiments treat a subject having cataracts and glaucoma with phacoemulsification (phaco) and excimer laser trabeculostomy (ELT). Phaco removes the cataract and inserts a clear replacement lens. ELT increases the flow of aqueous humor in the eye by perforating the trabecular meshwork with a laser. Phaco and ELT are administered during the same surgical visit, thereby minimizing the amount of surgeries for a patient having multiple eye conditions. Because phaco and ELT are less invasive than traditional surgeries, the amount of recovery time for the patient is minimized. In fact, both phaco and ELT are performed through one small incision that is made in the eye.

In some cases, various embodiments provide methods of treating a diagnosed eye condition and prophylactically treating a second eye condition during the same procedure. For example, a patient may be diagnosed with cataracts and require phaco surgery. Because certain of those patients with cataracts have a congenital risk of developing glaucoma, methods of the various embodiments administer prophylactic ELT treatment during the same surgical procedure as phaco treatment. The ELT provides treatment of glaucoma by increasing and/or improving outflow of aqueous humor to the eye. Thus, the patient diagnosed with cataracts will receive treatment for both eye conditions—cataracts and glaucoma—during the same surgical procedure.

Figure 10:
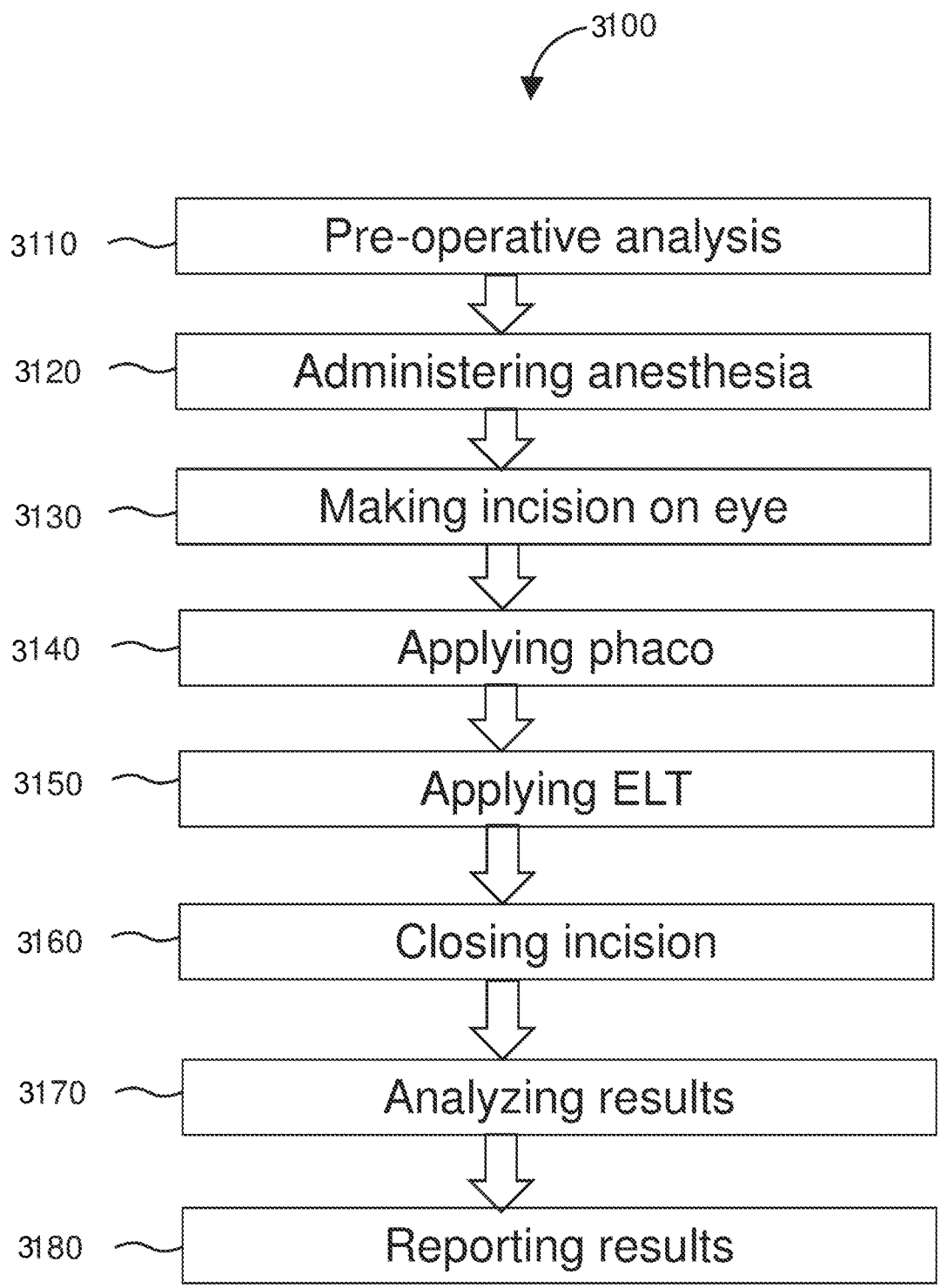
FIG. 10 is a flowchart of an embodiment of methods for applying ELT after a pre-operative analysis.

FIG. 10 shows a flowchart of an embodiment 3100. Methods of the various embodiments are directed to treatment of multiple eye conditions in a patient. In some examples, methods include 3110 pre-operative analysis and diagnosis of the eye conditions. In some embodiments, the diagnosed eye condition is cataracts and requires phacoemulsification surgery. The patient may also suffer from glaucoma. In various embodiments, excimer laser trabeculostomy (ELT) is used to treat glaucoma. In some cases, the ELT is provided as prophylactic treatment for glaucoma, as individuals with cataracts have an increased risk of developing glaucoma.

A patient having one or more eye conditions is prepared for surgery. The method includes 3120 administering anesthesia to the patient. Topical anesthesia is most commonly employed, typically by the instillation of a local anesthetic such as tetracaine or lidocaine. Alternatively, lidocaine and/or longer-acting bupivacaine anesthetic may be injected into the area surrounding (peribulbar block) or behind (retrobulbar block) the eye muscle cone to more fully immobilize the extraocular muscles and minimize pain sensation. A facial nerve block using lidocaine and bupivacaine may occasionally be performed to reduce lid squeezing. General anesthesia is recommended for children, traumatic eye injuries with cataract, for very apprehensive or uncooperative patients and animals. Cardiovascular monitoring is preferable in local anesthesia and is mandatory in the setting of general anesthesia. Proper sterile precautions are taken to prepare the area for surgery, including use of antiseptics like povidone-iodine. Sterile drapes, gowns and gloves are employed. A plastic sheet with a receptacle helps collect the fluids during phacoemulsification. An eye speculum is inserted to keep the eyelids open.

A physician 3130 makes a small incision on the eye of the patient. Before the phacoemulsification or ELT procedures can be performed, a small incision is made in the eye to allow the introduction of surgical instruments. Through the small incision, treatment procedures are administered during one surgical procedure.

The procedure includes 3140 applying phacoemulsification (phaco) treatment to the patient. Phacoemulsification is a modern cataract surgery in which the eye's internal lens is emulsified with an ultrasonic handpiece and aspirated from the eye. The physician removes the anterior face of the capsule that contains the lens inside the eye. The probe used during phaco is an ultrasonic handpiece with a titanium or steel needle. The tip of the needle vibrates at ultrasonic frequency and is used to sculpt and emulsify the cataract. A pump aspirates particles through the tip of the ultrasonic handpiece. In some techniques, a second fine steel instrument called a "chopper" is used from a side port to help with chopping the nucleus into smaller pieces. The cataract is usually broken into two or four pieces and each piece is emulsified and aspirated out with suction. The nucleus emulsification makes it easier to aspirate the particles. After removing all hard central lens nucleus with phacoemulsification, the softer outer lens cortex is removed with suction only.

An irrigation-aspiration probe or a bimanual system is used to aspirate out the remaining peripheral cortical matter, while leaving the posterior capsule intact. An intraocular lens implant (IOL), is placed into the remaining lens capsule. In some examples, the implant is a poly(methyl methacrylate) (PMMA) IOL, and the incision has to be enlarged. In some examples, the implant is a foldable IOL made of silicone or acrylic and is folded either using a holder, folder, or insertion device provided with the IOL. The IOL is inserted and placed in the posterior chamber in the capsular bag for in-the-bag implantations.

The procedure includes 3150 applying excimer laser trabeculostomy (ELT) treatment to the patient. In various embodiments, ELT and cataract surgery are performed through the same corneal incision. In some examples, a physician creates about 10 ELT sites in an eye of the patient after completing phacoemulsification in that eye.

The obstruction of aqueous outflow at the trabecular meshwork and inner wall of Schlemm's canal is the primary cause of elevated IOP in open-angle glaucoma (OAG). Various embodiments use excimer laser to perforate the Schlemm's canal. Other lasers, such as ruby and argon lasers, cannot achieve a permanent perforation of the trabecular meshwork to create an internal, rather than external, outflow channel. Though the photothermal and photodisruptive lasers were initially successful in puncturing the meshwork, the effect was short-lived due to inflammatory and healing responses. Excimer laser trabeculostomy (ELT) reestablishes the natural aqueous outflow of the eye without inciting a healing response at the target tissue.

Ablation with excimer lasers causes almost no thermal damage, therefore minimizing inflammation and the formation of scar tissue. A 308-nm xenon-chloride ultraviolet excimer laser causes minimal thermal damage compared with visible or infrared lasers. Unlike argon and selective laser trabeculoplasty, ELT precisely excises tissue without causing thermal injury or scarring the surrounding tissue. ELT treatment thus creates a long-term opening that connects the anterior chamber of the eye directly to Schlemm's canal. To avoid the corneal absorption of laser radiation, an optical fiber is used to deliver the energy. The fiber probe, or fiberoptic probe, is advanced through the incision and across the anterior chamber of the eye to contact the trabecular meshwork. A gonioscope or endoscope may be used by the physician to visualize placement of the fiber probe.

The physician applies pulsed photoablative energy. Typically, the physician creates 10 sites in one or two inferior quadrants. A small amount of bloody reflux from Schlemm's canal confirms each opening. The fiber probe is removed from the eye. Notably, the IOP decreases immediately after administering the ELT procedure. Topical antibiotics and steroid drops are used by the patient for 1 to 2 weeks post-operatively.

After applying phaco and ELT treatments, a physician 3160 closes the incision. Secure closure of the incision is necessary to prevent endophthalmitis. Typically, a physician uses sutures to close the incision. Some physicians place a suture in the incision and other physicians reserve a suture for when there is persistent leakage. The number of sutures required also depends on the type of IOL implanted during the phaco procedure. For example, a foldable IOL requires few or no sutures because the foldable IOL may be inserted through an incision that is smaller than required for insertion of a PPMA IOL.

Methods of the various embodiments include 3170 analyzing post-operative results and 3180 reporting results and scheduling post-operative follow-up with the patient after surgery. For example, the physician's analysis may include observing a small amount of bloody reflux from Schlemm's canal to confirm each opening. In turn, the physician may report the results to the patient, prescribe post-operative medication, such as topical antibiotics and steroid drops, and schedule a follow-up post-operative visit with the patient.

FIG. 11 shows a flowchart of an embodiment 1401 for diagnosing and performing an ELT procedure. As described herein, an ELT procedure may be performed without performing a phaco treatment or in conjunction with a phaco treatment. Similarly the embodiment 1401 may be performed regardless of whether a phaco treatment is given to a patient. Specifically the method 1401 may be used to prophylactically treat a patient to prevent them from developing glaucoma and/or an elevated intraocular pressure (TOP).

The embodiment 1401 includes, at 1402, performing a pre-operative analysis of a patient, where the patient is determined during the pre-operative analysis to have a congenital or otherwise elevated risk for developing glaucoma or elevated TOP. The risk factors that may be considered during the pre-operative analysis at 1402 may include one or more of age, family history, race, gender, presence of a comorbidity (e.g., presence of a condition that is associated with risk for developing glaucoma and/or elevated TOP).

Because the ELT treatment has relatively high levels of success in perforating a patient's trabecular meshwork without significant risk of damage to the tissue surrounding the perforations, ELT treatments are considered relatively safe and typically have quick recoveries without complications. As such, since risks associated with ELT treatments are low and positive outcomes are high, ELT procedures may be safely performed on patients that may not yet have glaucoma and/or elevated TOP, but may be at risk of glaucoma and/or elevated TOP. In other words, since ELT procedures are less invasive, ELT treatments may be performed on more patients that have one or more risk factors for glaucoma and/or elevated TOP without high risk of side effects or failure of the treatment over time.

During the pre-operative analysis, the risk factors assessed may be one or more risk factors, where if the risk factor (or more than one risk factor) is present, the patient may be considered to be at risk of developing glaucoma and/or elevated TOP. For example, if a patient is at or above a certain age, the patient may be determined to be at risk of developing glaucoma and/or elevated TOP and therefore may be qualify for an ELT procedure during the pre-operative analysis. For example, the patient may be at or above age 40, at or above age 45, at or above age at or above age 55, at or above age 60, at or above age 65, at or above age 70, at or above age or at or above age 80 to be considered at risk for glaucoma and/or elevated TOP. In various examples, the patient may be considered at risk if they have a congenital risk that is associated with higher incidences of glaucoma, such as if they are of a particular race, such as African American or black, Latino, south Asian or Indian, East Asian (e.g., Chinese, Japanese, and/or Korean), etc. A congenital risk may also be determined based on a family history of glaucoma and/or elevated TOP. In various examples, the patient may be considered at risk if they are a particular gender. In various examples, the patient may be considered at risk if they have other illnesses or conditions present, such as ocular hypertension, obesity, diabetes, etc (e.g., comorbidities). In various examples the patient may be considered at risk if they are a tobacco or alcohol user, or if their alcohol or tobacco use has occurred for a minimum threshold of years or if the frequency of their alcohol or tobacco use is above a particular threshold.

At 1404, if the patient has been determined to have a congenital or otherwise sufficient risk factor for developing glaucoma and/or elevated TOP, the ELT procedure may be performed on the patient to prophylactically prevent the onset of glaucoma and/or elevated TOP based on the pre-operative analysis and determination.

In various embodiments, the pre-operative analysis at 1402 may also include a genetic analysis or test of the patient. For example, a patients genetic cellular material (e.g., DNA, RNA) may be sampled and analyzed to look for markers or indicators that a patient may be at risk of glaucoma and/or elevated TOP.

One risk factor may be race as discussed above. A certain type of glaucoma called closed angle glaucoma may be more likely to occur in East Asian (e.g., Chinese, Japanese, Korean) persons. As such, an ELT procedure may be performed if a patient is East Asian (either with or without identification of another risk factor) due to a risk of developing closed angle glaucoma. In addition, certain aspects of an eye of a patient may be measured or examined to see if the patient is at risk of developing closed angle glaucoma (e.g., monitor or measure the thickness of the patient's lens of the eye and/or angle of the iris). Such aspects may represent a higher risk or indication of developing closed angle glaucoma, and therefore may be considered a risk factor for developing glaucoma and/or elevated TOP.

Angle-closure glaucoma, also called closed-angle glaucoma, occurs when an iris of the eye bulges forward to narrow or block the drainage angle formed by the cornea and iris. As a result, fluid can't circulate through the eye and pressure increases. This is demonstrated in FIGS. 12A and 12B. In FIG. 12A, fluid can move normally from the underside of the iris, between the iris and the lens to the topside of the iris, and drain normally through the trabecular meshwork. When the fluid can drain normally, IOP can stay at an appropriate level.

In FIG. 12B, a closed angle is shown that can increase IOP and cause glaucoma. In particular, the lens is thickened, causing it to press up against the iris and block flow of fluid from underneath the iris to the topside of the iris. The iris may further bulge, which may further block drainage paths out of the trabecular meshwork. As such, fluid in the eye may not drain properly and may cause elevated IOP and glaucoma. Bulging of the iris, thickening of the lens, and buildup of pressure below the iris may further cause pressure on the Schlemm's canal through which fluid may drain, thereby reducing the fluid that may flow through Schlemm's canal.

In certain individuals, the lens of the eye may continue to grow and thicken as a person ages. As such, closed angle glaucoma risks may be associated with certain races and certain ages of a patient during pre-operative analysis. One method of treatment for closed angle glaucoma is through use of a phaco procedure, where the lens of the eye that has thickened is replaced with an artificial lens that is thinner, and a path for fluid drainage between the lens and the iris, as well as possibly between the iris and trabecular meshwork, may also be opened again. In this way, the phaco procedure gets the iris to move downward so that the trabecular meshwork may be accessed and therefore an ELT procedure may be successful. As described herein, it may be desirable to perform phaco and ELT treatments during a same procedure. As such, when a patient is either identified as being at risk for closed angle glaucoma or is being treated for closed angle glaucoma, it may be advantageous to perform an ELT treatment on the patient. In this way, drainage of fluid out of the eye may improve and a phaco procedure may be delayed if not yet necessary, or the ELT and phaco procedures may be advantageously performed together as described herein.

As such, according to the various embodiments described herein, ELT may be performed with or without performing a phaco procedure based on the condition of a patient and the risk factors present in the patient. Risk factors such as congenital risk factors may be determined during a pre-operative analysis of the patient and their eyes to determine if the patient is at risk of developing glaucoma and/or elevated IOP, if the patient already has elevated IOP but does not yet have glaucoma, etc. In other words, an ELT treatment may be applied prophylactically to treat glaucoma even if the patient has not yet been diagnosed with glaucoma and/or without the patient actually having glaucoma. Similarly, if one or more risk factors are identified as being present in the patient, and the patient has not yet been identified as having elevated TOP, an ELT treatment may still be performed on the patient due to the identified risk factor(s).

In various embodiments, a specific risk factor may not even be identified. The trabecular meshwork in every human eye becomes more impermeable with age. As such, after a particular age, an ELT procedure may be applied to a patient regardless of specific congenital risk factors. In other words, the ELT procedure may be applied completely prophylactically, despite the absence of (or lack of knowledge of) any particular risk factors other than age. As such, the ELT procedure may be used as a preventative measure, even before a patient has elevated TOP or before any risk factor is identified in a patient.

Figure 13:
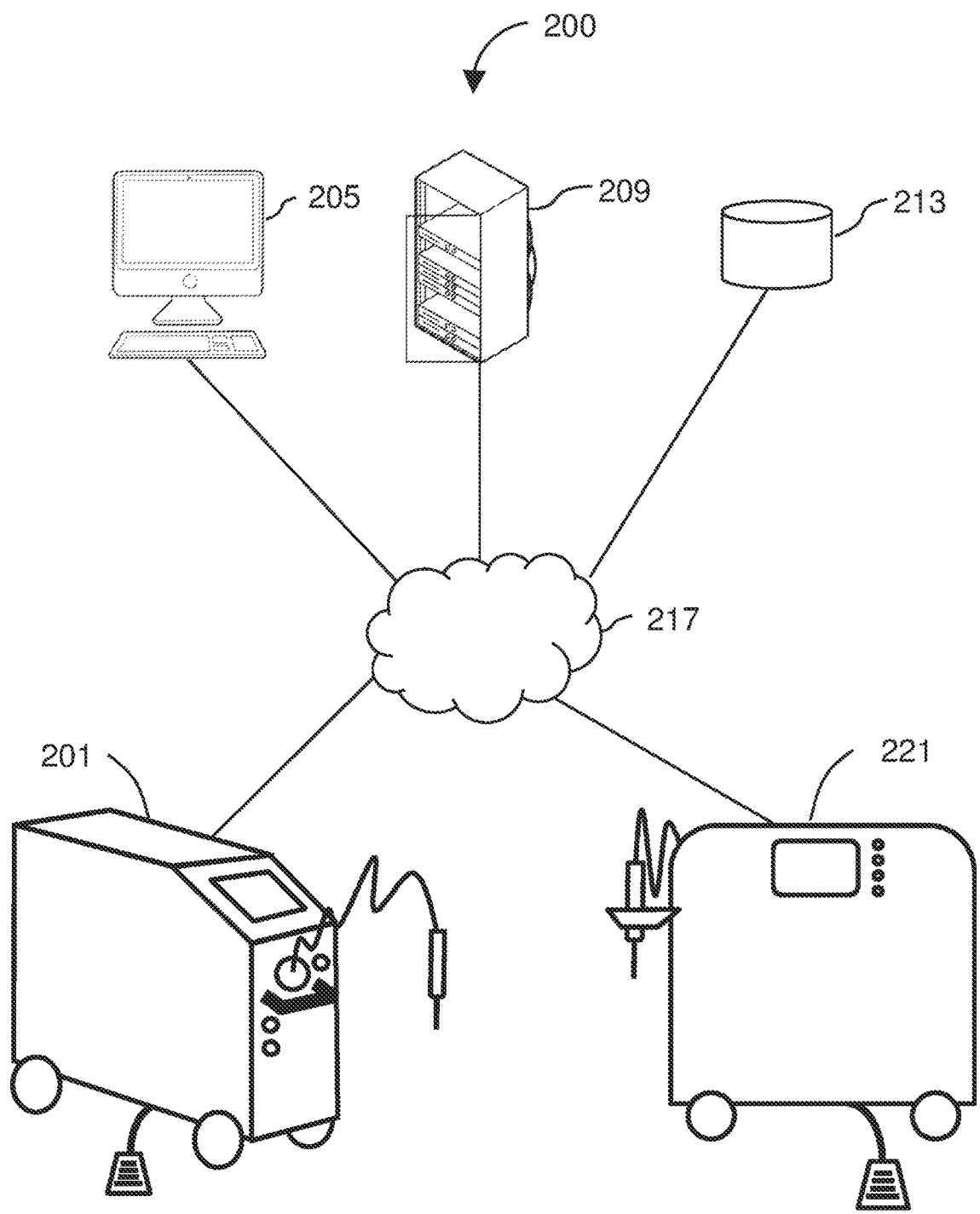
FIG. 13 shows an embodiment of systems for phaco and ELT treatment.

FIG. 13 diagrams a schematic of system 200 according to various embodiments. The system 200 includes an ELT instrument 201 and a phaco instrument 221 communicatively coupled to a computer 205. The system 200 optionally includes a server 209 and storage 213. Any of the ELT instrument 201, phaco instrument 221, the computer 205, the server 209, and the storage 213 that are included may exchange data via communication network 217. Where methods of the various embodiments employ a client/server architecture, steps of methods of the various embodiments may be performed using the server, which includes one or more of processors and memory, capable of obtaining data, instructions, etc., or providing results via an interface module or providing results as a file. The server may be provided by a single or multiple computer devices, such as the rack-mounted computers sold under the trademark BLADE by Hitachi. In system 200, each computer may include at least one processor coupled to a memory and at least one input/output (I/O) mechanism.

A processor generally includes a chip, such as a single core or multi-core chip, to provide a central processing unit (CPU). A processor may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. A computer of the various embodiments may include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. The system 200 may be used to perform methods described herein. Instructions for any method step may be stored in memory and a processor may execute those instructions.

Figure 14:
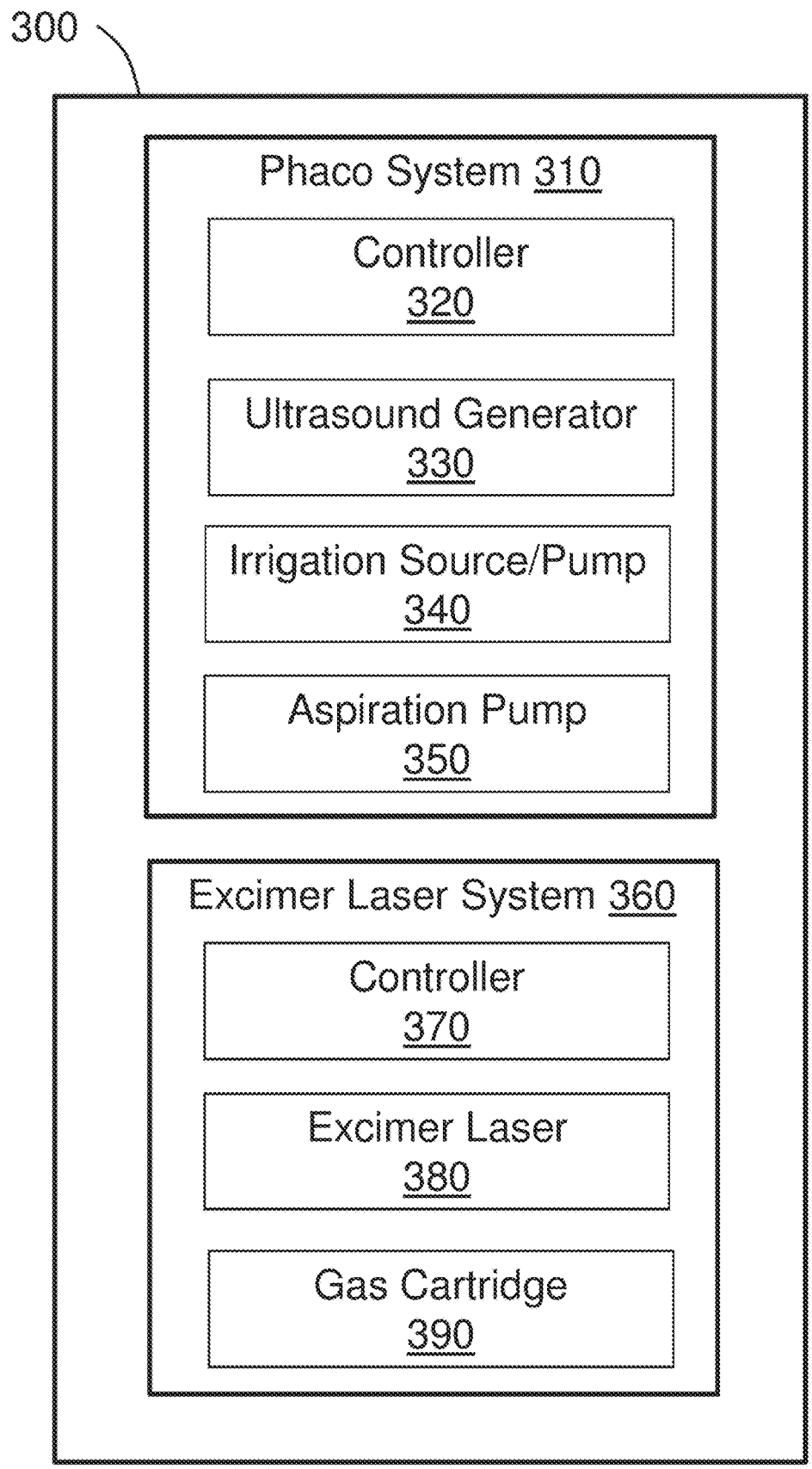
FIG. 14 shows an embodiment of systems for combined phaco and ELT treatment.

FIG. 14 is a diagram of a treatment system 300 according to the various embodiments. The system 300 is used to treat multiple eye conditions, such as cataracts and glaucoma. The treatment system 300 comprises a phacoemulsification (phaco) system 310 and an excimer laser trabeculostomy (ELT) system 360. The phaco system 310 includes a controller 320, ultrasound generator 330, irrigation source and/or pump 340, and aspiration source and/or pump 350. The phaco system 310 may be housed in an instrument. An ultrasound probe may connect to the phaco system and instrument for use during phaco treatment. The excimer laser system 360 comprises a controller 370, excimer laser 380, and gas cartridge 390. The excimer laser system 360 may be contained in a housing, and a fiber probe may connect to the housing for use during ELT treatment.

FIG. 4 shows an embodiment of the excimer laser trabeculostomy (ELT) instrument 400. An excimer laser is contained in the housing 402. The housing has wheels 404 and is portable. The push-pull handle 405 assists with portability of the ELT instrument 400. A foot pedal 414 extends from the housing 402 and is operable to provide power for delivering shots from the laser through the fiber probe 102, 104. A connector of the fiber probe 102, 104 connects to the excimer laser in the housing 402 at the fiber connection port 406. The housing comprises an interactive user interface 416. In some examples, the interactive user interface 416 displays patient information, machine settings, and procedure information. The housing 402 includes control buttons, switches, and dials, such as a fiber probe cap holder 408, an emergency stop button 410, and a power switch 412.

FIG. 5 shows a capped version of the fiber probe 500. FIG. 6 shows an embodiment of the probe 500 with the cap 514 removed, exposing the delivery tip 506 of the probe 500. The probe 500 is a single use, disposable unit. In some embodiments, the fiber probe 500 has a tag that determines operability. In some examples, a radio frequency identification (RFID) tag must match an RFID on the instrument in order to operate. The probe 500 generally includes a laser transmitting member and an illumination member as previously described herein, wherein each are coupled to their respective sources (i.e., laser source 108 and light source 110) by way of a connector 502 (elongated cord) extending from the body of the probe 500 and having a connection assembly 504 configured to be received within the connection port 406 of the instrument 400. The probe 500 further includes a delivery tip 506 from which laser energy (from the laser transmitting member) and visible light (from the illumination member) may be emitted. The probe 500 includes a handheld body 508, which may include a finger grip 510 with ridges or depressions 512. The body 508 of the handheld probe 500 may be metal or plastic. The fiber tip 506 at the distal end of the probe comprises an optical fiber jacketed in metal, such as stainless steel or titanium. The jacketed fiber at the distal end of the probe is inserted into the trabecular meshwork of the eye. A foot pedal is depressed to power the laser. When powered, the laser delivers a shot from the laser that travels through the optical fiber to the trabecular meshwork and Schlemm's canal.

Figure 15:
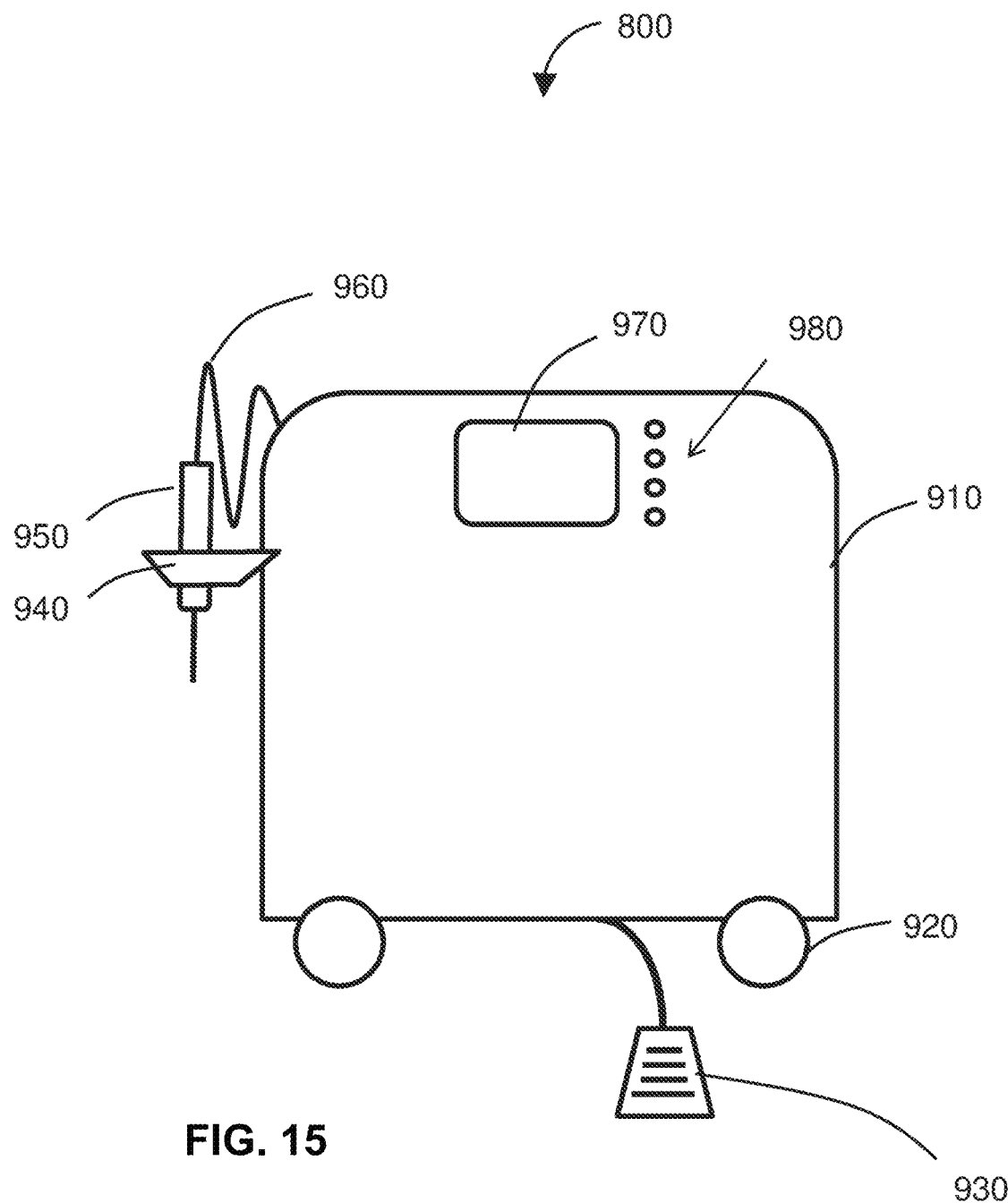
FIG. 15 shows an embodiment of a phaco system.

FIG. 15 shows a phaco system or instrument 800. The phaco instrument 800 has a housing 910 that houses the ultrasound generator. The housing 910 is portable and has wheels 920. A foot pedal 930 extends from the housing 910 and is used to provide energy from the ultrasound generator to the ultrasound probe 950. A holder 940 extends from the housing 910 to hold the ultrasound probe 950 when it is not in use. The ultrasound probe 950 is connected to the ultrasound generator through connector 960. The phaco instrument includes an interactive display 970 and additional controls 980. For example, the controls 980 may be control dials or buttons and may include a power switch and emergency stop switch. The interactive display 970 may display irrigation flow rate, suction flow rate, and ultrasound frequency and amplitude.

Figure 16:
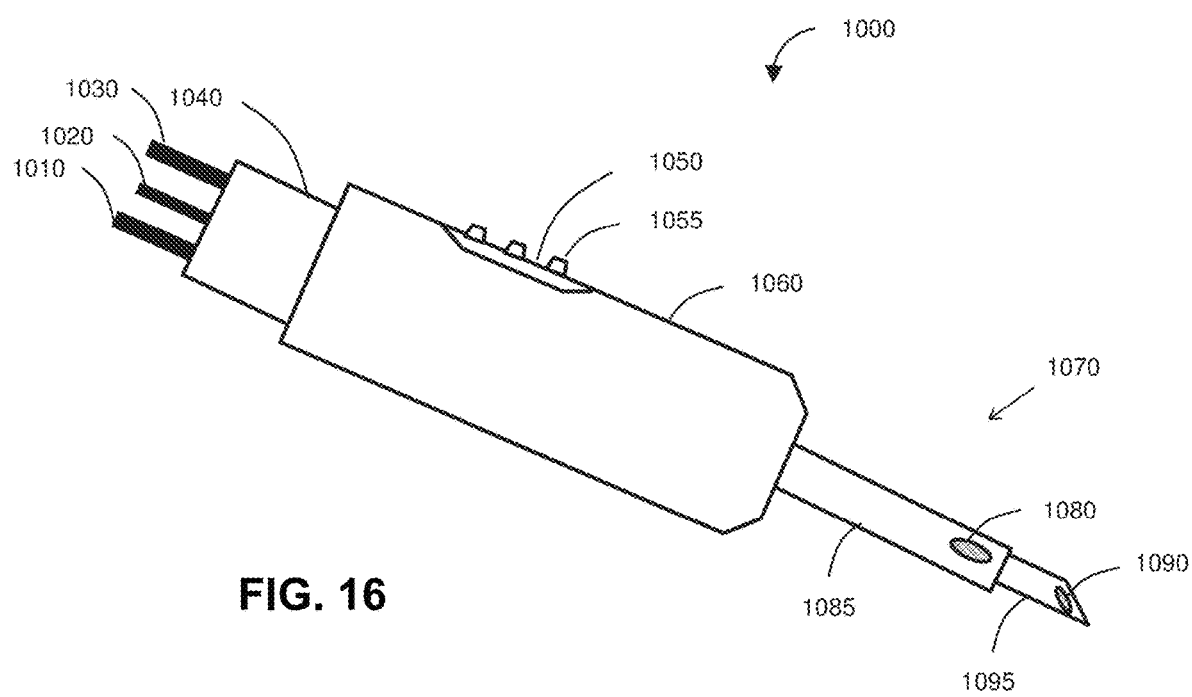
FIG. 16 shows an embodiment of a phaco probe.

FIG. 16 shows the ultrasound probe 1000 used during phaco. The ultrasound probe 1000 may also be referred to as a phaco probe, an ultrasonic probe, or a phaco handpiece. The phaco probe connects to the phaco system with connector 1040, which may be a protective plastic sheath. The protective sheath of connector 1040 covers the irrigation line 1010, ultrasound power line 1020, and aspiration line 1030. The connector 1040 connects the phaco system with the body 1060 of the phaco ultrasonic probe 1000. The body 1060 of the ultrasonic probe 1000 optionally has a finger grip 1050 with ridges 1055. The phaco probe is sterilized by any suitable method that provides sterilized equipment suitable for use on humans. In some embodiments, the phaco probe is disposable. The body 1060 of the ultrasound probe 1000 has a tip 1070. The tip 1070 includes the needle 1095 and the irrigation sleeve 1085. The needle 1095 is made of titanium or steel. The needle has a beveled tip (e.g., at 0°, 15°, 30°, and 45° with respect to the tip). The phaco needle operates at a frequency of 40 kHz with amplitude of $3/1000$ of an inch. At the distal opening of the needle is the aspiration port 1090. The aspiration port 1090 communicatively coupled to the aspiration source/pump and subsequently to a drain source. The needle also has one or more irrigation ports 1080. The irrigation port 1080 is communicatively coupled to the irrigation source/pump. The silicone irrigation sleeve 1085 or silicon material covers the phaco tip and protects the cornea and iris from heat energy transmitted by the probe. In certain examples, the pumps used for irrigation and aspiration are selected from peristaltic pumps, Venturi pumps, and diaphragmatic pumps.

Figure 17:
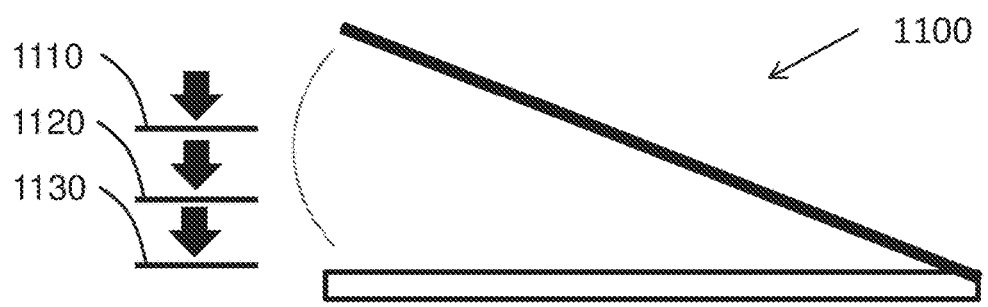
FIG. 17 shows an embodiment of a foot pedal.
Figure 18:
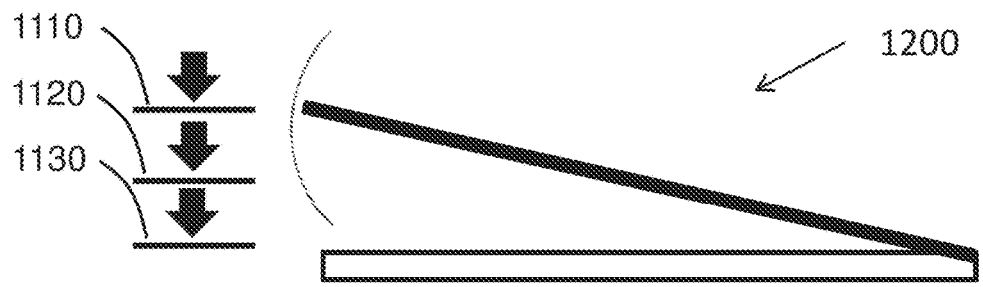
FIG. 18 shows an embodiment of a foot pedal.
Figure 19:
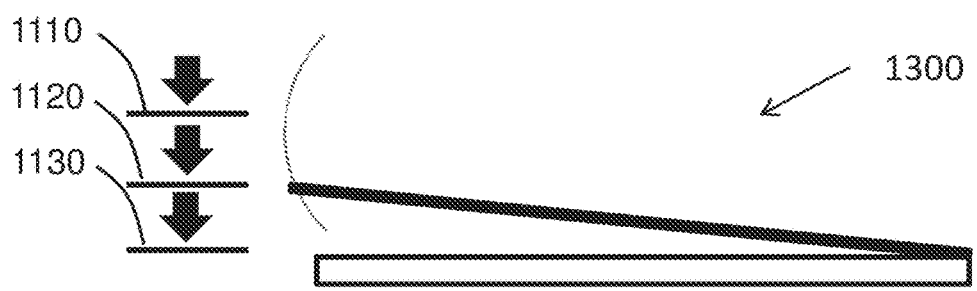
FIG. 19 shows an embodiment of a foot pedal.
Figure 20:
FIG. 20 shows an embodiment of a foot pedal.

FIGS. 17-20 show embodiments of the foot pedal according to various embodiments. In certain embodiments, the instrument comprises one foot pedal for the phaco procedure and one foot pedal for the ELT procedure. The foot pedal has a number of positions. As shown in FIGS. 17-20, there are four positions. The initial position is when the foot pedal 1100 is not depressed, as shown in FIG. 17. In FIG. 18, the foot pedal 1200 is in a first position 1110 and is slightly depressed. In FIG. 19, the foot pedal 1300 is in a second position 1120 and is moderately depressed. In FIG. 20, foot pedal 1400 is in a third position 1130 and is fully depressed.

In an embodiment, the foot pedal is used for the phaco procedure. In the first position, the phaco foot pedal provides irrigation only. In the second position, the phaco foot pedal provides irrigation and aspiration. In the third position, the phaco foot pedal provides irrigation, aspiration, and phaco power.

In an embodiment, the foot pedal is used for the ELT procedure. Each depression of the foot pedal may result in one shot from the laser. For example, when the foot pedal is depressed to the first position, as shown in FIG. 18, one shot is fired from the laser. When the foot pedal is depressed to the second position, as shown in FIG. 19, one shot is fired from the laser. When the foot pedal is depressed to the third position, as shown in FIG. 20, one shot is fired from the laser. Alternatively, the energy provided by the foot pedal may increase with each position of the laser. For example, at the first position, one shot may be fired from the laser, while the second position fires two shots from the laser, and the third position fires three shots from the laser.

Figure 21A:
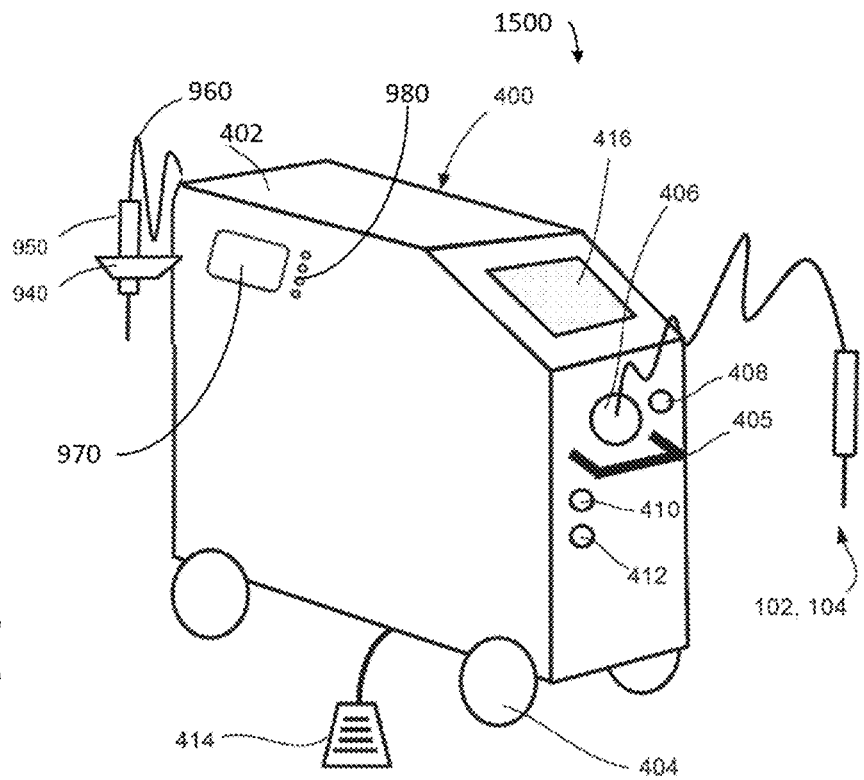
FIG. 21A shows an embodiment of combined ELT and phaco system.

While FIGS. 4 and 15 show separate machines/systems for ELT and phaco procedures, phaco and ELT systems may further be combined into a single machine according to the embodiments described herein. For example, FIG. 21A shows a machine 1500 that includes components of both the ELT system of FIG. 4 and the phaco system of FIG. 15. Such a machine may take up less space in an operating room, which may be advantageous to allow an operator and anyone else in the operating room more space to maneuver. In addition, such a system may be advantageous where, as described herein, phaco and ELT treatments are performed together on the same patient during a same operation or procedure. The operator may therefore not have to move and switch between machines if they are using a combined machine as in FIG. 21A.

The machine 1500 of FIG. 21A shows a single pedal 414 that may be configured to operate and or work with both of the probe 950 for phaco treatments and the probe 102, 104 for the ELT treatments. In such embodiments, the operator may be able to toggle a switch or otherwise make an input into the machine 1500 to indicate whether they are using the ELT probe 102, 104 or the phaco probe 950. In another example, the machine 1500 may be programmed or configured to determine which probe is being used by the operator. For example, the handle of the probes may be equipped with a touch sensor so that only the probe that is being held by the operator may be operated using the pedal 414. In another example, the probes may be further actuated by a button or other switch on the probe in combination with the pedal, such that the pedal may only control a probe on which a button or other switch is depressed or otherwise activated (e.g., like a safety). In another example of the probes being actuated with a button on the handle and the pedal 414, the button on the handle and the pedal may be used for different functions. For example, the pedal may be used to set the power delivered by the laser/probe, and a button on the handle may be used to actually deliver a shot of energy per the setting of the pedal. As such, the machine 1500 may not accidentally fire a laser for a probe not in use because a button on the probe may still have to be actuated in order to get the given laser/probe to fire. In various embodiments, other combined machines for ELT and phaco treatments may have more than one pedal, such as one pedal used for the phaco system/treatments and one pedal used specifically for the ELT system/treatments.

Figure 21B:
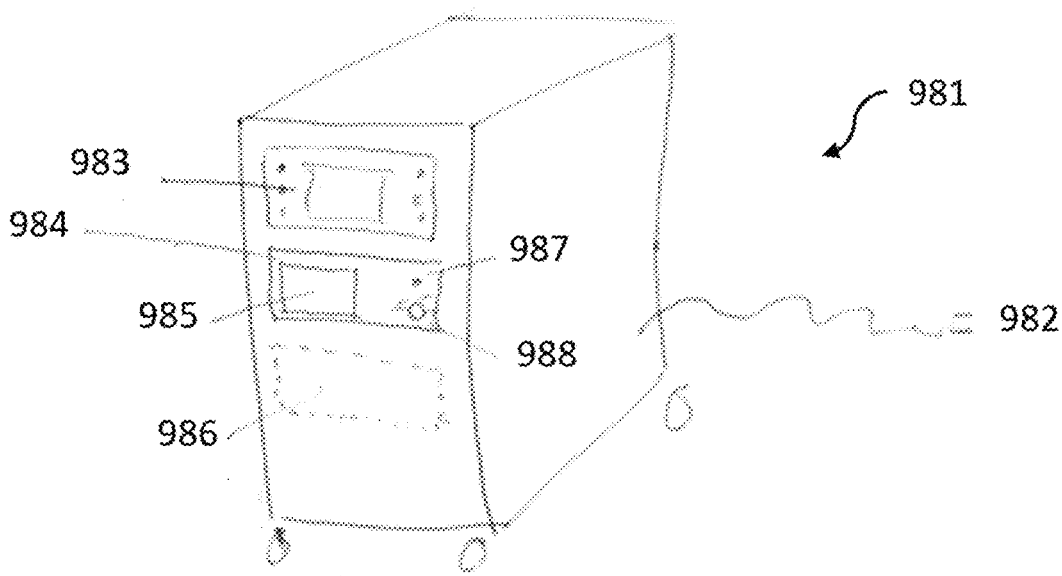
FIG. 21B shows an embodiment of combined ELT and phaco system.

FIG. 21B shows another example of a combined ELT/phaco machine 981. The machine 981 may advantageously have only a single power cord 982 for plugging into external power. The machine 981 may include a phaco unit 983 and an ELT unit 984. Each of the phaco and ELT units 983 and 984 may be at a height that is convenient for a user to plug in and/or remove probes from the machine. In the example of FIG. 21B, the phaco unit 983 and the ELT unit 984 are at different heights, but still oriented toward a top of the machine 981 for ease of access by a user. In other embodiments, the phaco unit 983 and the ELT unit 984 may be oriented at a same height. The ELT unit 984 may include a display 985, a receiver 987 to connect to a fiber probe, and an energy monitor 988 configured to receive the distal end of a fiber probe, so that laser light emitted by the probe may be received by a sensor of the machine 981 to calibrate the laser power being emitted by a probe. When inserted into the energy monitor, the distal end of the probe may have a sterile adapter attached to it that may be discarded after calibration. In this way, the distal end of the probe that will be inserted into an eye does not come into contact with the machine 981 or the energy monitor 988. The energy monitor 988 may also have a shutter, so that the sensor is only exposed when the probe is inserted and the shutter is therefore pushed back. In various embodiments, a single sensor and port for calibrating a laser probe may be used for both an excimer laser for the ELT procedure and a laser and probe used in a phaco procedure. A section 986 shown in phantom of the machine 981 may also include other internal aspects of the machine, such as vitrectomy components, irrigation/aspiration components, feeds for both ELT and phaco lasers, etc. The section 986 may also include or may be an access panel that allows the machine 981 to be serviced as desired.

In various embodiments, an excimer laser (and any components associated therewith described herein) for performing an ELT (e.g., an ELT laser, ELT components) may be combined with different components than those associated with a phacoemulsification unit. For example, the excimer or ELT components may be combined with any other components that may be used to treat a cataract or other eye condition. For example, the excimer or ELT components may also be located in a same housing as, powered by a same cord/outlet as, etc. components for a femtolaser cataract surgery. In such an example, a femtolaser is used to create an opening in a front layer of the lens of an eye, and the laser is also used to break up a cloudy lens that has the cataract(s) and then may be suctioned out. As such, the femtolaser and suction components may be included in a same housing as the excimer or ELT components similar to the embodiments with ELT and phacoemulsification components described above. As a result, a femtolaser treatment for cataracts may also be combined with an ELT procedure, similar to the embodiments described herein that combine an ELT procedure with a phacoemulsification procedure.

Such machines may save space in an operating room and therefore increase efficiency during procedures performed on a patient. In various embodiments, an ELT laser that fits into existing phaco machines (or phaco machines designed to house other laser components) may also be manufactured, and then inserted into a phaco machine. Such a process may include inserting the ELT components, fixing them to the phaco machine structure, and connecting the ELT components to a power output or bus of the phaco machine.

Excimer Laser Fiber Illumination

In current laser trabeculostomy procedures, a surgeon utilizes a gonio lens, a special contact lens prism, held over the eye, in combination with light, in order to visualize the working end of the laser fiber when positioning the laser fiber relative to the trabecular meshwork.

While a surgeon may have some view of the target site (i.e., the trabecular meshwork), the combination of the gonio lens and the current light source relied upon for illuminating the target site is inadequate. In particular, current procedures rely on an external beam of light (from a slit lamp) in an attempt to illuminate the anterior chamber angle where the cornea and the iris meet (i.e., the location of the trabecular meshwork). However, the external light source may fail to provide a comprehensive view within the eye and is limiting. As such, a surgeon is unable to visually verify, with confidence, the position of the laser relative to the trabecular meshwork, the effectiveness of laser treatment to any given portion of the meshwork, as well as drainage of the aqueous humor upon laser treatment. For example, without proper visualization, a surgeon may position the laser too close or too far from the trabecular meshwork and/or position the laser at improper angles relative to the trabecular meshwork, resulting in unintended collateral tissue damage or the creation of channels that inadequate and do not provide the desired drainage. As a result, the laser treatment may be inadequate, as the desired drainage may not be achieved, and thus patients may require additional post-operative procedures to lower the intraocular pressure.

Systems of the embodiments herein include a laser probe for performing an intraocular procedure. The laser probe is a single use, disposable probe configured to be coupled to a laser source and transmit laser energy from the laser source to a target tissue for treatment thereof. The laser probe includes both a laser transmitting member and a light emitting member in a single component. In particular, the laser probe includes a fiber optic core comprising a delivery tip for transmitting laser energy from the laser source to the target tissue during a procedure. The laser probe further includes a light emitting member providing illumination in a field of view proximate to the delivery tip of the fiber core, thereby providing a clear field of view for a surgeon during laser treatment of the target tissue.

The laser probe of various embodiments herein may be particularly well suited for a laser trabeculostomy procedure. During such a procedure, it is critical that the surgeon has a clear field of view within the eye, particularly of the anterior chamber angle where the cornea and the iris meet so that the position of the laser relative to the trabecular meshwork can be clearly visualized. A surgeon may guide the delivery tip of the fiber optic core of the laser probe through a corneal incision of the eye and towards the trabecular meshwork. The light emitting member emits a visible light signal within the eye and proximate to the delivery tip, thereby illuminating a field of view in which the surgeon can better visualize positioning of the delivery tip and subsequent transmission of laser energy upon the trabecular meshwork. By providing a laser probe with an integrated lighting member, illumination is provided internally (i.e., within the eye), as opposed to current procedures which rely on an external light source, and thus provides a much more comprehensive view within the eye and the improved view of the target location. By providing an improved view, a surgeon is able to better position the delivery tip relative to the trabecular meshwork so as to achieve optimal photoablation and channel formation in the meshwork and/or Schlemm's canal. In particular, the orientation and positioning of the delivery tip is critical when attempting to create optimal channel formation in the tissue, particularly when attempting to achieve placement of channels in the meshwork relative to Schlemm's canal, which will provide optimal drainage. Furthermore, the surgeon is able to visually verify, with more confidence, the effectiveness of the laser treatment by visualizing drainage of the aqueous humor as a result of the laser treatment.

In various embodiments herein, an excimer laser probe may be provided for performing an intraocular procedure. The intraocular procedure may include a laser trabeculostomy and thus the target tissue includes trabecular meshwork and/or Schlemm's canal. However, it should be noted that a laser probe consistent with the present disclosure can be used in any laser treatment of eye conditions, including, but not limited to, diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism.

The laser probe may include a fiber optic core comprising a proximal end couplable to an excimer laser source and a distal end comprising a delivery tip for transmitting laser energy from said excimer laser source to a target tissue for treatment thereof. The laser probe further includes an illumination member for providing illumination in a field of view proximate to said delivery tip of said fiber core.

In various embodiments, the illumination member comprises an optical fiber for receipt of a light signal from an illumination source. The illumination source provides a light signal within the visible light spectrum. Accordingly, the illumination source may include, but is not limited to, an incandescent light source, a fluorescent light source, a halogen light source, a high-intensity discharge light source, a metal halide light source, and a light emitting diode (LED) light source.

In various embodiments, the optical fiber is coaxially aligned with the fiber core. In other embodiments, the optical fiber is adjacent to the fiber core. The laser probe further includes an outer jacket surrounding the optical fiber and fiber core.

Another aspect of the various embodiments described herein may be an excimer laser system for performing an intraocular procedure. Again, the intraocular procedure may include a laser trabeculostomy and thus the target tissue includes trabecular meshwork and/or Schlemm's canal. The excimer laser system includes an excimer laser source, an illumination source, and a disposable, single use probe operably couplable to the excimer laser source and illumination source and configured to be used in the intraocular procedure. The laser probe includes a fiber optic core comprising a proximal end couplable to the excimer laser source and a distal end comprising a delivery tip for transmitting laser energy from said excimer laser source to a target tissue for treatment thereof. The laser probe further includes an illumination member for receiving an illumination signal from the illumination source and for providing illumination in a field of view proximate to said delivery tip of said fiber core.

In various embodiments, the illumination member comprises an optical fiber for receipt of a light signal from an illumination source. The illumination source provides a light signal within the visible light spectrum. Accordingly, the illumination source may include, but is not limited to, an incandescent light source, a fluorescent light source, a halogen light source, a high-intensity discharge light source, a metal halide light source, and a light emitting diode (LED) light source.

In various embodiments, the optical fiber is coaxially aligned with the fiber core. In other embodiments, the optical fiber is adjacent to the fiber core. The laser probe further includes an outer jacket surrounding the optical fiber and fiber core.

In various embodiments, a laser probe may provided. The laser probe may be a single use, disposable probe configured to be coupled to a laser source and transmit laser energy from the laser source to a target tissue for treatment thereof. The laser probe includes both a laser transmitting member and an illumination member in a single component. In particular, the laser probe includes a fiber optic core comprising a delivery tip for transmitting laser energy from the laser source to the target tissue during a procedure. The laser probe further includes a light emitting member providing illumination in a field of view proximate to the delivery tip of the fiber core, thereby providing a clear field of view for a surgeon during laser treatment of the target tissue.

The laser probe of various embodiments may be suited for intraocular procedures in which laser treatment of target tissues is desired. In particular, the laser probe of various embodiments may be used for treating glaucoma and useful in performing a laser trabeculostomy. However, it should be noted that a laser probe consistent with the present disclosure can be used in any laser treatment of eye conditions, including, but not limited to, diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism.

During a laser trabeculostomy procedure, it is critical that the surgeon has a clear field of view within the eye, particularly of the anterior chamber angle where the cornea and the iris meet so that the position of the laser relative to the trabecular meshwork can be clearly visualized. By using the laser probe, a surgeon may guide the delivery tip of the fiber optic core of the laser probe through a corneal incision of the eye and towards the trabecular meshwork. The light emitting member emits a visible light signal within the eye and proximate to the delivery tip, thereby illuminating a field of view in which the surgeon can visualize, with the aid of a gonio lens, positioning of the delivery tip and subsequent transmission of laser energy upon the trabecular meshwork. By providing a laser probe with an integrated lighting member, illumination is provided internally (i.e., within the eye), as opposed to current procedures which rely on an external light source, and thus provides a much more comprehensive view within the eye and the improved view of the target location. By providing an improved view, a surgeon is able to better position the delivery tip relative to the trabecular meshwork so as to achieve optimal photoablation and channel formation in the meshwork and/or Schlemm's canal. In particular, the orientation and positioning of the delivery tip is critical when attempting to create optimal channel formation in the tissue, particularly when attempting to achieve placement of channels in the meshwork relative to Schlemm's canal, which will provide optimal drainage. Furthermore, the surgeon is able to visually verify, with more confidence, the effectiveness of the laser treatment by visualizing drainage of the aqueous humor as a result of the laser treatment.

As discussed above, FIG. 4 shows an embodiment an excimer laser system 100; FIG. 5 shows an embodiment of a probe 500 for use with the excimer laser system 100, illustrating the probe 500 having a capped, distal delivery tip 506; and FIG. 6 shows an embodiment of the probe 500 with the cap 514 removed, exposing the delivery tip 506 of the probe 500.

Figure 22:
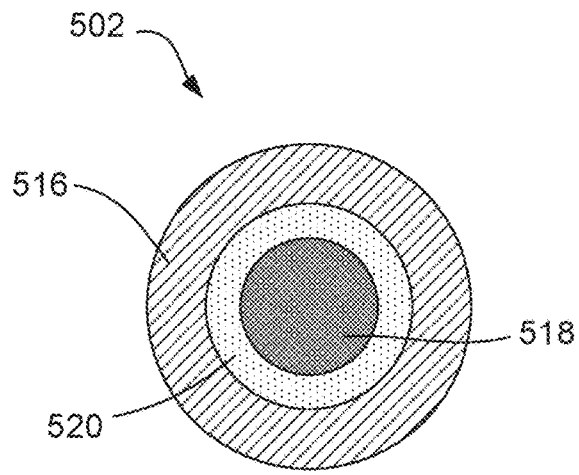
FIG. 22 shows a cross-sectional view of the probe taken along line A-A of FIG. 6.
Figure 23:
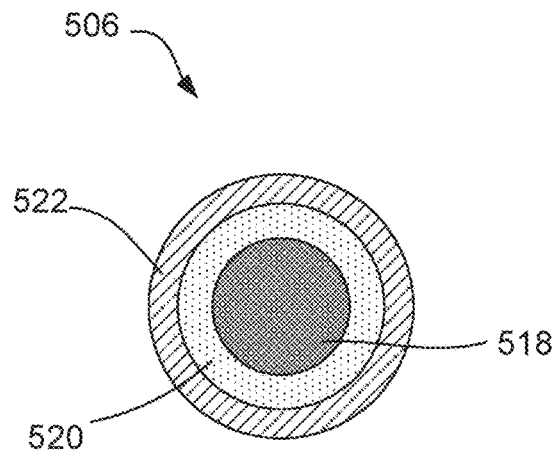
FIG. 23 shows a cross-sectional view of the probe taken along line B-B of FIG. 6.

FIGS. 22 and 23 show cross-sectional views of the probe 500 taken along line A-A and line B-B of FIG. 6, respectively. As shown, the laser transmitting member may include fiber optic core 518 that runs through the fiber probe 500 and forms part of the connector 502. Similarly, the illumination member may include an optical fiber 520 that also runs through the fiber probe 500 and forms part of the connector 502. A protective sheath 516 surrounds the fiber optic core 518 and optical fiber 520. In some examples, the protective sheath 516 is a protective plastic or rubber sheath. The fiber optic core 518 and optical fiber 520 further form part of the delivery tip 506 of the probe 500. A metal jacket 522 surrounds the fiber optic core 518 and optical fiber 520. In some instances, a stainless steel jacket 522 surrounds and protects the fiber optic core 518 and optical fiber 520. As illustrated, in some embodiments, the optical fiber 520 is coaxially aligned with the fiber optic core 518, either surrounding the core 518, or, in other embodiments, the core 518 may surround the fiber 520. In other embodiments, the optical fiber 520 is adjacent to the fiber optic core 518.

Figure 24:
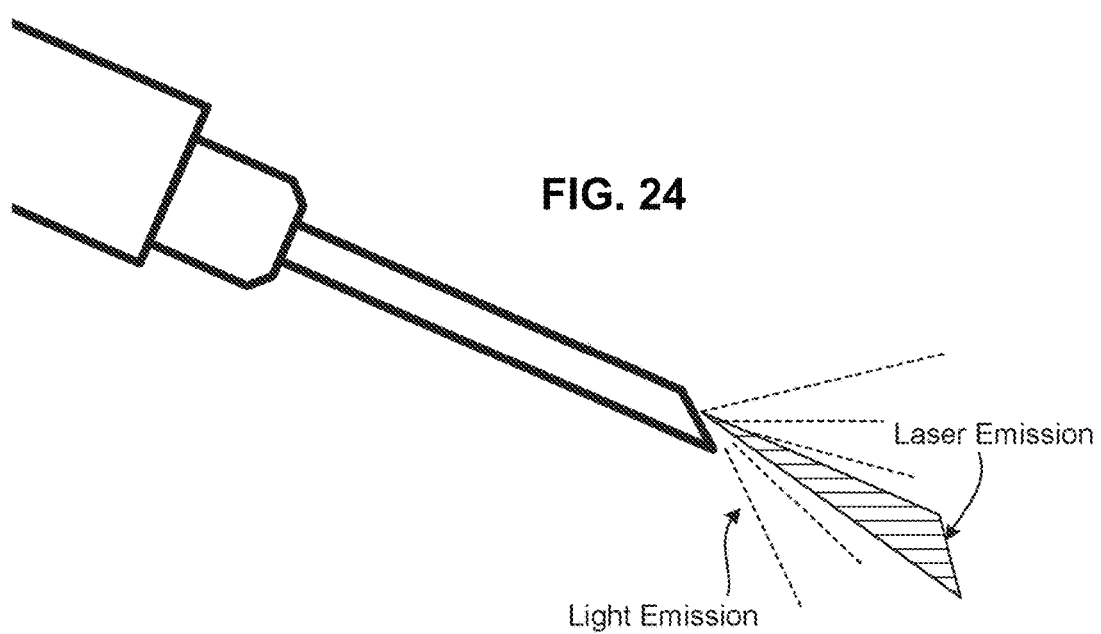
FIG. 24 shows an enlarged view of the delivery tip of a probe emitting both visible light for illuminating a field of view and laser energy for photoablation of a target tissue.

FIG. 24 shows an enlarged view of the delivery tip 502 of a probe 500 emitting visible light (via emission from the optical fiber 520 upon receipt of light signals from the light source 110) and emitting laser energy (via emission from the fiber optic core 518 upon receipt of laser pulses from the laser source 108) for photoablation of a target tissue.

Figures 25, 26:
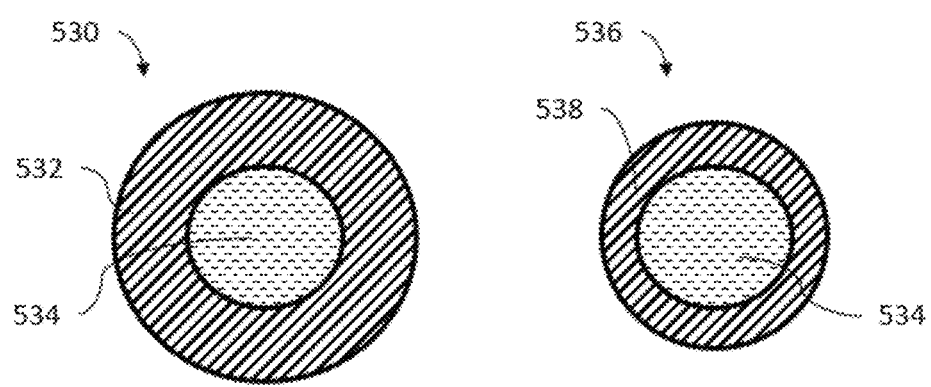
FIG. 25 shows an alternative cross-sectional view of the probe taken along line A-A of FIG. 6.
FIG. 26 shows an alternative cross-sectional view of the probe taken along line B-B of FIG. 6.

FIGS. 25 and 26 show alternate embodiments of a probe, with cross-sectional views 530 and 536 similar to FIGS. 22 and 23 of the probe 500 taken along line A-A and line B-B of FIG. 6, respectively. As shown, the laser transmitting member may include a fiber optic core 534 that runs through the fiber probe 500 and forms part of the connector 502. In this embodiment, visible light from the light source 110 of the laser system 100 may be transmitted through the fiber optic core 534 along with the laser used for a treatment for glaucoma. That is, in various embodiments, the laser system 100 may not have a separate illumination member 104 in its probe member 102. Rather, the probe member 102 may have a single fiber optic core (e.g., the fiber optic core 534) through which both excimer laser light and visible light for illuminating a treatment area inside the eye may pass. The visible light and excimer laser light may pass through the fiber optic core 534 without interfering with one another due to their different wavelengths, or may interfere with one another to a small enough degree that the use of the excimer laser for the eye treatment may not be impacted. In this way, both the excimer laser light and the visible light may pass through a single fiber optic core 534.

In addition to reducing the cost of the probes and fiber optics therein by having one instead of two optical fibers, the connector 502 (elongated cord) attached to a probe may be easier to manipulate having only one optical fiber inside instead of two. Such a configuration may make the connector 502 (elongated cord) less stiff, and may reduce the diameter, weight, etc. of the connector 502. In addition, the visible light output at the delivery tip 502 of the probe 500 may be even closer to where the laser is being applied for the laser trabeculostomy treatment. In this way, the light emitted by a single fiber optic core 534 through which both the excimer laser light and visible light is passed may more effectively illuminate a treatment area within the eye. A protective sheath or metal jacket 532 may also surround the fiber optic core 534 in FIG. 25. In some examples, the protective sheath 532 is a protective plastic or rubber sheath. A protective sheath or metal jacket 538 may surround the fiber optic core 534 in FIG. 26. In various embodiments, the protective sheath or metal jacket 532 may be a stainless-steel jacket and may surround and protect the fiber optic core 534. As illustrated, in various embodiments, the protective sheath or metal jacket 532 is coaxially aligned with the fiber optic core 534. As such, the protective sheath or metal jacket 532 is adjacent to the fiber optic core 534.

In various embodiments, different types of light may be used. For example, visible white light may be used to illuminate the angled structure of the trabecular meshwork for better visibility while approaching a fiber probe toward the trabecular meshwork before it comes into contact with the tissue of the trabecular meshwork. Visible white light may also illuminate structure in front of the delivery tip of the fiber probe while the probe is in contact with tissue, such as the trabecular meshwork. In various embodiments, specific wavelengths of visible light may be used in addition to or in the alternative to visible white light. For example, light of a wavelength that is highly absorptive by blood may be used, so that the operator may be able to more easily identify and/or visualize Schlemm's canal and other blood vessels present in the eye. Similarly, light of a wavelength that is not highly absorbed by blook may be used to visualize blood structure (e.g., a sort of negative picture of what would be shown with light that is highly absorptive by blood). Such wavelengths may offer an operator better visibility into structures of the eye, including vessels and other structures that are not on the surface of portions of the eye.

The laser probe may be suited for intraocular procedures in which laser treatment of target tissues is desired. In particular, the laser probe may be used for treating glaucoma and useful in performing a laser trabeculostomy. However, it should be noted that a laser probe consistent with the present disclosure can be used in any laser treatment of eye conditions, including, but not limited to, diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism.

During a laser trabeculostomy procedure, it is critical that the surgeon has a clear field of view within the eye, particularly of the anterior chamber angle where the cornea and the iris meet so that the position of the laser relative to the trabecular meshwork can be clearly visualized. By using the laser probe, a surgeon may guide the delivery tip of the fiber optic core of the laser probe through a corneal incision of the eye and towards the trabecular meshwork. The light emitting member emits a visible light signal within the eye and proximate to the delivery tip, thereby illuminating a field of view in which the surgeon can visualize, with the aid of a gonio lens, positioning of the delivery tip and subsequent transmission of laser energy upon the trabecular meshwork. By providing a laser probe with an integrated lighting member, illumination is provided internally (i.e., within the eye), as opposed to current procedures which rely on an external light source, and thus provides a much more comprehensive view within the eye and the improved view of the target location. By providing an improved view, a surgeon is able to better position the delivery tip relative to the trabecular meshwork so as to achieve optimal photoablation and channel formation in the meshwork and/or Schlemm's canal. In particular, the orientation and positioning of the delivery tip is critical when attempting to create optimal channel formation in the tissue, particularly when attempting to achieve placement of channels in the meshwork relative to Schlemm's canal, which will provide optimal drainage. Furthermore, the surgeon is able to visually verify, with more confidence, the effectiveness of the laser treatment by visualizing drainage of the aqueous humor as a result of the laser treatment.

Authentication Systems and Methods for an Excimer Laser System

In the medical industry, there are many surgical devices, instruments and systems comprised of individual components that must work together properly to ensure treatment is performed safely and as intended. For example, medical laser systems are used to treat various conditions in various practice areas (i.e., urology, neurology, otorhinolaryngology, general anesthetic ophthalmology, dentistry, gastroenterology, cardiology, gynecology, and thoracic and orthopedic procedures). Medical laser systems consist of a laser unit, which generates laser radiation, and a separate laser probe having an optical fiber adapted to direct laser radiation from the laser, through the fiber and to the treatment area.

Specific components of a laser system can be designed by a manufacturer to be utilized with other specific components. For example, there are a variety of medical optical fibers available in the marketplace that can be used with laser systems. Currently available laser systems may provide laser light at various wavelengths and thus may be used for particular purposes and procedures. As such, optical fibers to be used with these laser systems may have varying sizes (diameter, length, etc.), be made of various materials, operate at various temperatures, operate at various wavelengths, and have physical characteristics (e.g., bend radii). Specific components of a laser system can be designed by a manufacturer to be utilized with other specific components. For example, there are many varieties of medical optical fibers available in the marketplace that can be used with laser systems that are used in medical procedures. Furthermore, the manufacturer of one component may also manufacture other components of a laser system, or may certify that these other components can be used with the manufacturer's own components.

Prior to beginning a medical procedure, it is important that the proper optical fiber be connected to the laser unit that is to be used for the medical procedure. Oftentimes, the manufacturer of the laser unit recommends usage of particular brands of optical fibers and/or particular optical fibers with the laser unit. When one of the components being used is not a certified product, the full capabilities of the system may not be achieved and may further cause malfunctions, endangering patient safety. For example use of an improper optical fiber can result in damage to the equipment, delay in conducting a medical procedure until the proper optical fiber is obtained, and/or result in the potential for an ineffective, damaging, or potentially life-threatening medical procedure.

The various embodiments provides a system for authenticating laser probes for use with a laser system. In such a system, the elements generally include a laser unit and single-use, disposable laser probes to be coupled to the laser unit, each laser probe having an optical fiber adapted to direct laser radiation from the laser unit, through the fiber, and to the treatment area. The laser unit comprises a control system for operating the laser unit, including controlling output of laser radiation to a laser probe coupled to the laser unit. The laser unit further includes structure(s) configured to authenticate any given laser probe to determine whether the laser probe is suitable and/or authorized to operate with the laser unit. In particular, the laser unit includes an RFID reader for reading data embedded in an RFID tag associated with the laser probe upon attachment of the laser probe to the laser unit. The data from the RFID tag is analyzed by the control system and a determination is made as to whether the laser probe is authentic (i.e., suitable for use with the laser unit). In the event that the laser probe is determined to be authentic, the control system allows for transmission of laser radiation to the laser probe and thus a procedure can be performed using the laser probe. In the event that the laser probe is determined to not be authentic, the control system prevents transmission of laser radiation to the laser probe.

The authentication analysis is based on a correlation of the RFID tag data with known, predefined authentication data stored in a database, either locally in the laser unit, or stored in a remote database. The known, predefined authentication data is controlled by the owner/manufacturer of the laser unit, such that the owner/manufacturer can determine what laser probes are to be used with the laser unit. The owner/manufacturer may set a specific authentication key or provide for specific identity numbers that are proprietary to the owner/manufacturer. As such, the RFID tag data for any given laser probe must include a corresponding unique identifier (i.e., authentication key or identity number) in order to be deemed authentic. The RFID tag data may include other information and/or characteristics associated with the laser probe and optical fiber. For example, in some embodiments, the RFID tag data further includes operational history information of the laser probe. As such, in some embodiments, it is further possible to utilize the control system to deauthenticate a laser probe based on operational history, such as in the event that the probe has already been used and/or reached the suggested maximum number of laser pulses, thereby preventing further use of the laser probe with the laser unit.

Accordingly, the authentication system of the various embodiments ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

The various embodiments provide a system for authenticating laser probes for use with a laser system. In such a system, the elements generally include a laser unit and single-use, disposable laser probes to be coupled to the laser unit, each laser probe having an optical fiber adapted to direct laser radiation from the laser unit, through the fiber, and to the treatment area. The laser unit comprises a control system for operating the laser unit, including controlling output of laser radiation to a laser probe coupled to the laser unit. The laser unit further includes structure(s) configured to authenticate any given laser probe to determine whether the laser probe is suitable and/or authorized to operate with the laser unit. In particular, the laser unit includes an RFID reader for reading data embedded in an RFID tag associated with the laser probe upon attachment of the laser probe to the laser unit. The data from the RFID tag is analyzed by the control system and a determination is made as to whether the laser probe is authentic (i.e., suitable for use with the laser unit). In the event that the laser probe is determined to be authentic, the control system allows for transmission of laser radiation to the laser probe and thus a procedure can be performed using the laser probe. In the event that the laser probe is determined to not be authentic, the control system prevents transmission of laser radiation to the laser probe.

Accordingly, the authentication system of the various embodiments ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

The laser unit and laser probe of various embodiments may be suited for intraocular procedures in which laser treatment of target tissues is desired. In particular, the laser probe and laser unit of various embodiments may be used for treating glaucoma and useful in performing a laser trabeculostomy. However, it should be noted that a laser probe consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

Figure 27:
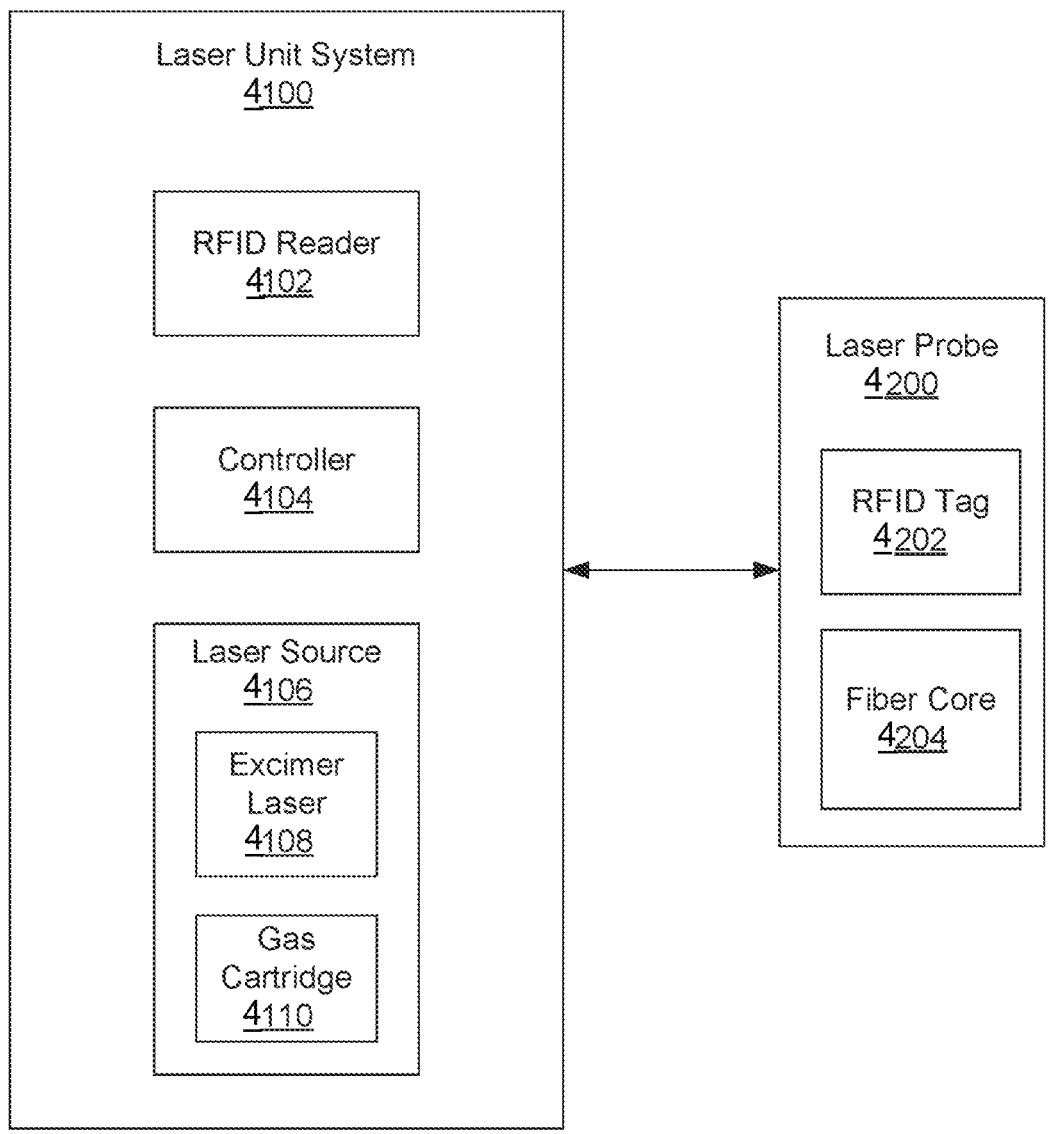
FIG. 27 diagrams an excimer laser system of the present disclosure.

FIG. 27 diagrams an excimer laser system, including a laser unit system 4100 and a laser probe 4200 to be attached to the laser unit system 4100. The system 4100 includes an RFID reader 4102, a controller 4104 (also referred to herein as a "control system 4104"), and a laser source 4106. The laser probe 4200 includes an RFID tag 4202 and a fiber core 4204. As will be described in greater detail herein, many of the components of the laser unit system 4100 may be contained in a housing, such as a moveable platform, to be provided in a setting in which the procedure is to be performed (e.g., operating room, procedure room, outpatient office setting, etc.) and the probe 4200 may connect to the housing for use during treatment. Upon coupling the probe 4200 to the housing, the fiber core 4204 is coupled to the laser source 4106 and adapted to direct laser radiation from the laser source 4106, through the fiber, and to the treatment area.

The laser source 4106 may include an excimer laser 4108 and a gas cartridge 4110 for providing the appropriate gas combination to the laser 4106. The excimer laser 4106 is a form of ultraviolet laser that generally operates in the UV spectral region and generates nanosecond pulses. The excimer gain medium (i.e., the medium contained within the gas cartridge 4110) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 4108 of the present system 4100 is an XeCl excimer laser and emits a wavelength of 308 nm.

The controller 4104 provides an operator (i.e., surgeon or other medical professional) with control over the output of laser signals (from the laser source 4106 to the fiber core 4204) and, in turn, control over the transmission of laser energy from the fiber core 4204 of the probe 4200. However, prior to providing an operator with control over laser output, the laser probe 4200 undergoes an authentication procedure to determine whether the laser probe 4200 is in fact suitable for use with the laser unit system 100. In particular, upon coupling the laser prober 4200 to the system 4100, the RFID reader 4102 reads data embedded in the RFID tag 4202 of the laser probe 4200, wherein such RFID tag data is analyzed to determine authenticity of the laser probe 4200.

Figure 28:
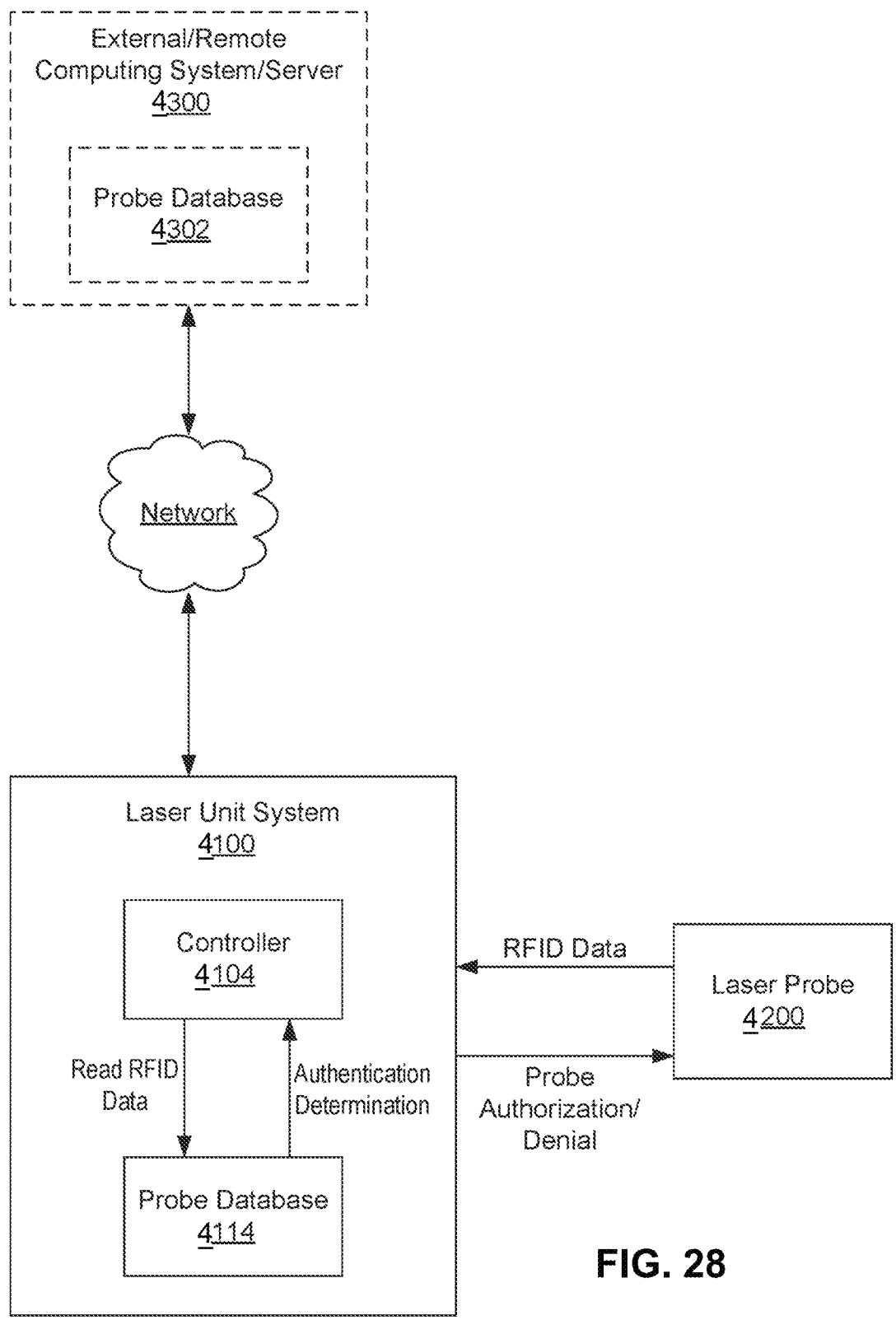
FIG. 28 diagrams the excimer laser system of the present disclosure and authentication of a laser probe to be used with the excimer laser system.

FIG. 28 diagrams the laser system 4100 and authentication of a laser probe 4200 to be used with the laser system 4100. The data from the RFID tag is read by the RFID reader, and then analyzed by the controller 4104. A determination is made as to whether the laser probe is authentic (i.e., suitable for use with the laser unit) based on the authentication analysis. In the event that the laser probe is determined to be authentic, the controller 104 allows for transmission of laser radiation to the laser probe 4200 and thus a procedure can be performed using the laser probe 4200. In the event that the laser probe is determined to not be authentic, the controller 4104 prevents transmission of laser radiation to the laser probe 4200.

The controller 4104 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 4104 may include a hardware processor coupled to non-transitory, computer-readable memory containing instructions executable by the processor to cause the controller to carry out various functions of the laser system 4100 as described herein, including controller laser and/or illumination output.

The authentication analysis is based on a correlation of the RFID tag data with known, predefined authentication data stored in a database, either a local database (i.e., probe database 4114) forming part of the laser unit system 4100, or a remote database hosted via a remote server 4300 (i.e., probe database 4302). For example, in some embodiments, the system 4100 may communicate and exchange data with a remote server 4300 over a network. The network may represent, for example, a private or non-private local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web).

The known, predefined authentication data stored in the database (database 4114 or database 4302) may be controlled by the owner/manufacturer of the laser unit 4100, for example, such that the owner/manufacturer can determine what laser probes are to be used with the laser unit. For example, the owner/manufacturer may set a specific authentication key or provide for specific identity numbers that are proprietary to the owner/manufacturer. As such, the RFID tag data for any given laser probe must include a corresponding unique identifier (i.e., authentication key or identity number) in order to be deemed authentic.

One approach to uniquely identifying a laser probe is to authenticate the probe by using a private key. In such an approach, both the laser system 4100 and the RFID tag 4202 are taught an identical key. The RFID tag 4202 and laser system 4100 then operate in conjunction to authenticate the key. More specifically, the laser system 4100 generates a random, unique challenge number. The RFID tag 4202 uses this challenge, in combination with the key to generate a response of an authentication code. The method for generating this code (known as a hash function) masks the value of the key. Another approach to uniquely identifying a laser probe is to use unique and unchangeable identity numbers. This approach can be used if there is a region of memory (e.g., a serial or model number), that can only be written by the RFID manufacturer. The protection is realized by ensuring that the manufacturer only provides tags with legal identification numbers, which prevents simple duplication of legitimate tags.

The RFID tag data may include other information and/or characteristics associated with the laser probe and optical fiber. For example, in some embodiments, the RFID tag data further includes operational history information of the laser probe. As such, in some embodiments, it is further possible to utilize the controller 4104 to deauthenticate a laser probe based on operational history, such as in the event that the probe has already been used and/or reached the suggested maximum number of laser pulses, thereby preventing further use of the laser probe with the laser unit.

As generally understood, RFID technology uses electromagnetic fields to automatically identify and track tags attached to objects. As previously noted, the RFID tag associated with the laser probe contains electronically-stored information. The RFID tag may either be read-only, having a factory-assigned serial number that is used as a key into a database, or may be read/write, where object-specific data can be written into the tag by the system user. Field programmable tags may be write-once, read-multiple; "blank" tags may be written with an electronic product code by the user. The RFID tag contains at least three parts: an integrated circuit that stores and processes information and that modulates and demodulates radio-frequency (RF) signals; a sensor configured to collect DC power from the incident reader signal; and an antenna for receiving and transmitting the signal. The tag information is stored in a non-volatile memory. The RFID tag includes either fixed or programmable logic for processing the transmission and sensor data, respectively.

The RFID reader transmits an encoded radio signal to interrogate the tag. The RFID tag receives the message and then responds with its identification and other information. This may be only a unique tag serial number, or may be product-related information such as a stock number, lot or batch number, production date, or other specific information. Since tags have individual serial numbers, the RFID system design can discriminate among several tags that might be within the range of the RFID reader and read them simultaneously.

In some embodiments, the RFID tag may be a passive tag, which collects energy from the RFID reader of the laser system interrogating radio waves. In some embodiments, the RFID tag may be an active tag, which includes a local power source (e.g., a battery) and may operate hundreds of meters from the RFID reader of the laser system. FIG. 4 shows an example excimer laser unit that may be used in accordance with various embodiments. The RFID reader 4102, controller 4104, and laser source 4106 may be contained within a housing 402. It should further be noted that the RFID reader 4102 may be located in proximity to the connection port 406 to allow reading of data from the RFID tag 4202 that is provided on a connecting end of the laser probe 4200.

FIG. 29 shows an embodiment of a probe 500 similar to that of FIG. 6, except the connection assembly may additionally have an RFID tag embedded therein or attached thereto. For example, the RFID tag 4202 is provided on the connection assembly 504, such that, upon coupling the connection assembly 504 to the connection port 406 of the laser unit system 100, data embedded in the RFID tag 4202 can be read by the RFID reader 4102.

FIGS. 30 and 31 show cross-sectional views of the probe 500 taken along line A-A and line B-B of FIG. 29, respectively. As shown, a fiber optic core 518 runs through the probe 500 and forms part of the connector 502. A protective sheath 516 surrounds the fiber optic core 518. In some examples, the protective sheath 516 is a protective plastic or rubber sheath. The fiber optic core 518 further form part of the delivery tip 506 of the probe 500. A metal jacket 520 surrounds the fiber optic core 518 and optical fiber 520. In some instances, a stainless steel jacket 520 surrounds and protects the fiber optic core 518.

Figure 32:
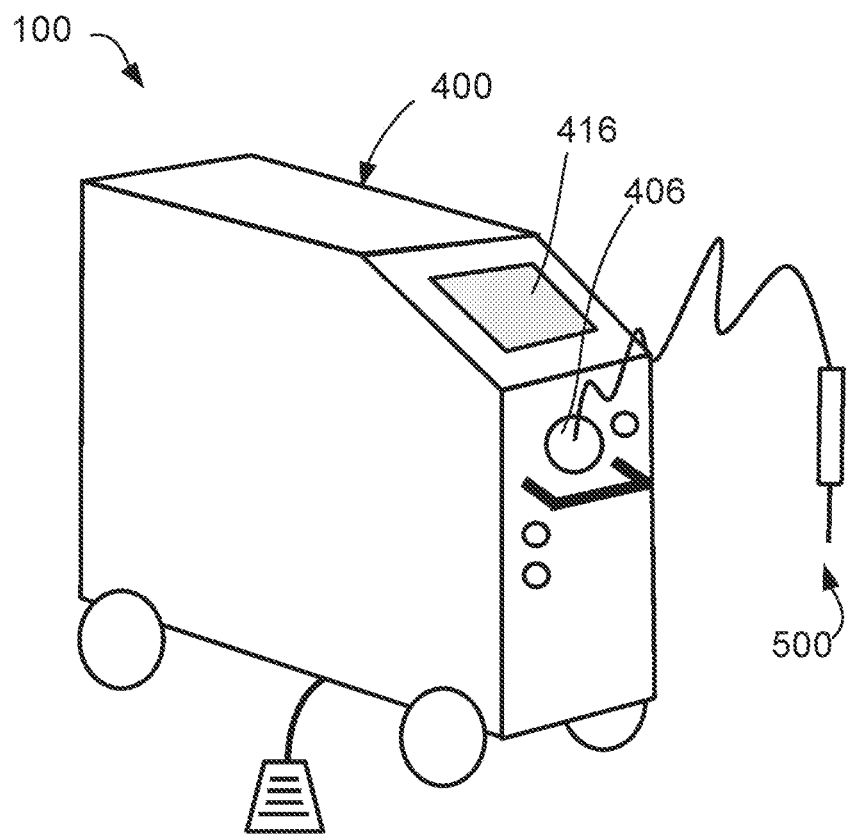
FIG. 32 shows an embodiment a laser probe attached to an excimer laser unit.
Figure 33:
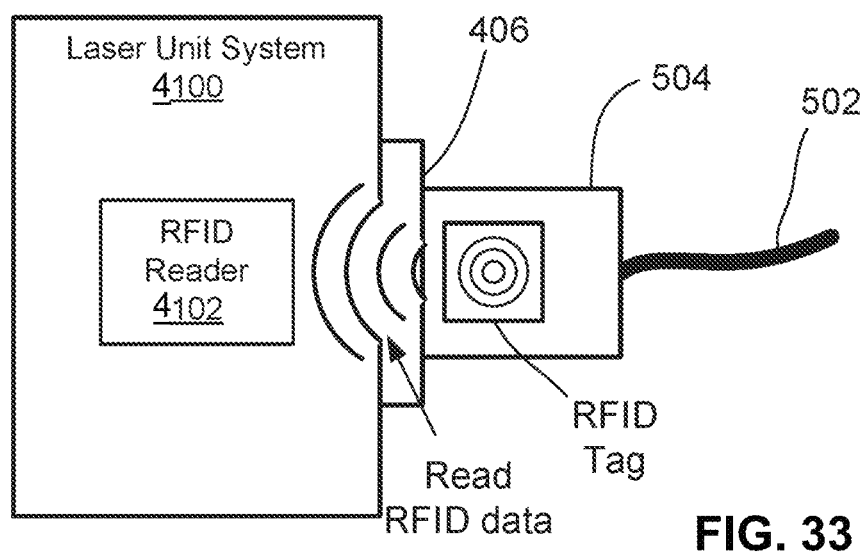
FIG. 33 shows an enlarged view of a connection between the laser probe and the excimer unit and initial RFID reading to determine authenticity of the laser probe.

FIG. 32 shows an embodiment a laser probe 500 attached to a laser unit system 100. As previously described, upon attachment of the laser probe 500 to the system 100 (i.e., coupling between the connection assembly 504 of the probe 500 and connection port 406 of the system 400), the RFID reader 4102 reads data embedded in the RFID tag associated with connection assembly 504. FIG. 33 shows an enlarged view of a connection between the laser probe 500 and the system 4100 and initial RFID reading to determine authenticity of the laser probe 4200. The data from the RFID tag is analyzed by the controller 4104 and a determination is made as to whether the laser probe is authentic (i.e., suitable for use with the laser unit). In the event that the laser probe 4200 is determined to be authentic, the controller allows for transmission of laser radiation to the laser probe 4200. In the event that the laser probe 4200 is determined to not be authentic, the controller 4104 prevents transmission of laser radiation to the laser probe.

Accordingly, the authentication system of various embodiments may ensure that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

FIGS. 34 and 35 show further examples of how probes may be authenticated for use with an excimer laser unit for ELT treatments. FIG. 34 is a flowchart of an embodiment for authenticating a probe for use with an excimer laser unit. FIG. 35 is a flowchart of an embodiment for preventing use of an unauthenticated probe.

At 3402, a probe may be connected to an ELT machine. The probe may have an RFID tag or other readable sensor or memory. The memory may include data that is used to authenticate the probe. At 3404, the authentication data stored on the probe may be read, for example, by a reader on the ELT machine. At 3406, the authentication data may be determined to be valid, for example by a processor of the ELT machine. In various embodiments, if the ELT machine is connected to a network of other computing devices, a processor of another device (e.g., a remote server) may be used to determine that the authentication data is valid. The authentication data may be encrypted or otherwise encoded so that the authentication data may be decoded or decrypted before determining its validity. Data stored on the probe may further be indicative of other information beyond its mere validity or invalidity. For example, data on the probe may indicate a country, city, or facility of origin (e.g., where the probe was made), a type of probe, a brand or trade name of the probe, a type of material used in the probe, an identity of a purchaser of the probe, an identity of a manufacturer of the probe, etc. As such, the ELT machine (either using its own processor or by way of another computing device) may determine various information about the probe stored on the probe. In various embodiments, the probe may determine the validity of the probe based on a lookup table or other database of probe information. For example, a lookup table or database may include information about valid probes, invalid probes, etc. If the authentication data matches data stored in the lookup table or database associated with valid probes, the probe may be considered valid. The lookup table may be stored on memory of the ELT machine or on the memory of another computing device connected to the ELT machine via a network.

If the probe is authenticated at 3406, the probe may be used for an ELT treatment at 3408. The probe may further be used in accordance with additional data stored on the probe or otherwise determined about the probe based on the data stored on the probe. For example, data stored on the probe may indicate how much total energy should be permitted to pass through the probe without significant degradation, may indicate how many total shots the probe should be used for, what wavelength of energy should be used with the probe, and/or any other aspect of using the probe. In various embodiments, instead of storing that data on the probe, the ELT machine or another computing device may identify the probe as a certain type of probe based on the data stored on the probe. In such embodiments, the ELT machine or other computing device may then determine, based on the type of probe that is attached, the additional information about how the probe should be used (e.g., how much total energy, number of shots, wavelength, etc.). Such information may further be stored in a lookup table or database, such that authentication can happen along with identifying other aspects of the probe even if those aspects are not specifically stored on the probe itself. Such lookup tables or databases may further be updated over time with information about new probes being manufactured so that ELT machines can properly determine whether probes are valid or not. Such updates may occur over a network, such as the internet.

At 3410, the authentication data on the probe is changed (e.g., the data stored on the memory of the probe is erased, changed, rewritten, added to, etc.) so that the authentication data is no longer valid. In other words, the data on the probe may be modified in some way such that, if the probe is reconnected to the ELT machine or another ELT machine, the ELT machine will determine that the probe is invalid and not permit usage of the probe. In this way, probes not made by a trusted manufacturer, probes that have already been used, probes that have been tampered with, etc., cannot be used. Similarly, if an ELT machine finds no data on a probe (e.g., the probe does not have an RFID tag, memory, etc.), the ELT machine may determine that the probe is invalid and prevent use of such a probe. Such methods protect patients, as counterfeit probes may not be manufactured properly and can lead to accidents where patient's eyes are damaged. Similarly, probes that have already been used may also be ineffective or dangerous for use on a patient, as the fiber optics in the probe may degrade after use.

Although embodiments described with respect to FIG. 34 relate to a probe having a memory which may be modified by an ELT machine, other embodiments of validating a probe are further contemplated herein. For example, the memory of a probe or RFID tag may have a static code or data stored thereon. The ELT machine may read that data from a probe, and check a database or lookup table to determine if that particular probe has been used before, and/or determine if the data on the probe is valid. If the data is valid but the lookup table or database does not indicate that the probe has been used before, the probe may be used with the ELT machine. Once the probe is used, a processor of the ELT machine or another computing device may update the lookup table or database to indicate that the particular probe associated with the data read from the probe has been used. Then if the ELT machine or other ELT machines read the data from that probe again, it can be determined from the lookup table or database that the probe has already been used, and the probe will not be permitted for use with the ELT machine.

FIG. 35 describes a method 3500 where probes are determined to be invalid. At 3502, it is determined that an invalid probe is connected to the ELT machine (e.g., based on data stored on the probe). At 3504, the ELT machine or a computing device associated with the ELT machine displays on an interface that the probe is invalid. As such, the probe may not be used with the ELT machine. In various embodiments, the method 3500 may end after 3504.

In other embodiments, at 3506, it may be determined that a predetermined threshold number of invalid probes have been attempted to be used with the ELT machine. In other words, if a particular number of invalid probes' use has been attempted, the machine may determine that a particular threshold has been met or exceeded. The threshold may be set by the manufacturer of the ELT machine, for example. After determining that the threshold has been exceed, the interface may display at 3508 that the ELT machine is disabled, not operating, or otherwise out of commission. Optionally, other information may be displayed, such as instructing an operator to get the ELT machine services, instructing the operator that the machine must be reset by a representative of the manufacturer due to too many invalid probe uses, etc. In various embodiments, such as when an ELT machine is connected to network, an alert or message may also be transmitted to a computing device controlled by or associated with a manufacturer of the ELT machine or other party than the operator of the ELT machine, so that the manufacturer or other party may be alerted to an attempted use of an invalid probe. An alert or message may similarly be sent only if a predetermined threshold of invalid probes are attempted to be used, which may be the same or a different threshold than the threshold that triggers disabling of the ELT machine. At 3510, the ELT machine itself may be disabled based on the threshold being met or exceeded. In this way, patients may be protected against operators that repeatedly attempt to use invalid probes for eye procedures.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Calibration System for Improving Manufacture Tolerance in Excimer Laser Optical Fibers In the medical industry, there are many surgical devices, instruments, and systems comprised of individual components that must work together properly to ensure treatment is performed safely and effectively. It is critical that any given component falls within an acceptable tolerance to ensure that the component physically fits and interacts appropriately with other components and functions as intended.

The actual production of any product (or operation of any system) involves some inherent variation of input and output. Measurement error and statistical uncertainty are also present in all measurements. Accordingly, tolerance is an inherent aspect when designing a device, instrument, or system. The concept of tolerance, sometimes referred to as engineering tolerance, relates to the permissible limit or limits of variation in a physical dimension of the component, a measured value or physical property of the component, spacing between the component and another component, and the like. Accordingly, if a component falls outside of a permissible tolerance (i.e., the component is too small, too large, fails to have acceptable properties, etc.), then the overall device, instrument, or system will fail to perform as designed.

One example of a surgical system composed of multiple components is a medical laser system. The medical laser system generally consists of a laser unit and a separate laser probe having an optical fiber for directing laser radiation from the laser unit to a treatment area. Laser units provide laser light at specific wavelengths and, as a result, may be designed to perform specific procedures. For example, certain procedures may require photocoagulation of a target tissue, which occurs upon delivery of laser radiation at a first wavelength, while other procedures may require photoablation of a target tissue, which occurs upon delivery of laser radiation at a second wavelength. In turn, optical fibers to be used with these laser systems may have specific dimensions, material compositions, and/or functional properties (i.e., operation at specific temperatures and wavelengths) so as to function as intended with the corresponding laser unit.

While current laser units allow for some tolerance (i.e., optical fiber dimensions, properties, or conditions may have some variation without significantly affecting functioning of the laser system), the range of permissible tolerance is exceedingly tight. For example, optical fibers have a very small diameter which is generally measured on the micron scale. The diameter of the optical fiber may impact the transmission of laser radiation through the optical fiber and thus may impact the laser radiation emitted from the delivery tip of the optical fiber. As such, there is very little room for variation in the manufacture of optical fibers. Manufacturing costs are increases as a result of the high degree of precision required to make sure the diameter of an optical fiber falls within the permissible tolerance. Furthermore, if a given optical fiber falls outside of a permissible tolerance (i.e., the diameter is too be or too small), use of the noncompliant optical fiber may result in transmission of laser radiation that is not at the desired wavelength. In turn, use of a noncompliant optical fiber runs the risk of providing an ineffective treatment and, in some instance, can cause additional unintended damage and harm.

Various embodiments provide a system for calibrating output from a laser source to compensate for increased variation in laser optical fibers. In such a system, the elements generally include a laser source for generating laser energy to be provided to one of a plurality of laser probes couplable thereto. Each laser probe includes an optical fiber, including a fiber optic core, adapted to direct laser radiation from the laser source, through the fiber, and to a desired the treatment area. The system further includes a laser management system for managing the laser source. The management system includes a control system configured to adjust laser energy output from the laser source to any given laser probe to maintain a consistent level of laser radiation delivered to the target area, despite variation in the fiber optic core of any given laser probe.

More specifically, as part of the initial setup, the control system receives data associated with a laser probe coupled to the laser source. The data may include one or more dimensions of the fiber optic core of the laser probe, including fiber optic core diameter. The data is then analyzed by the controller and, based on the analysis, a determination of an optimum level of laser energy output from the laser source is made. The optimum level of laser energy output from the laser source is based on a correlation of the laser probe data, such as specific dimensions of the fiber optic core, with calibration data. The calibration data may generally include a plurality of sets of values, wherein each set of values may include a laser energy output level from the laser source, a diameter of a fiber optic core of a laser probe to receive the laser energy output level, and the resulting wavelength value of laser radiation emitted from the delivery tip of the laser probe. The resulting wavelength value of laser radiation to be emitted from the delivery tip may remain constant, regardless of the diameter of the fiber optic core. In such an embodiment, the laser management system (i.e., the control system) automatically adjusts the laser energy output level from the laser source (i.e., increases or decreases output level) for any given diameter of a fiber optic core so as to maintain the emission of laser radiation upon a target area at a consistent wavelength, despite variation in the diameter of fiber optic cores from the plurality of laser probes.

Accordingly, the system of various embodiments may be able to compensate for wide range of variations across a plurality of laser probes by simply adjusting output of the laser source to account for such variations. In turn, the manufacture tolerance for optical fibers improves as less precision is required during the manufacturing process, which reduces overall costs. Furthermore, by fine tuning of the laser output, the laser radiation is maintained at a consistent wavelength, ensuring that the target area is treated as intended and patient safety is maintained.

The various embodiments provide a system for calibrating output from a laser source to compensate for increased variation in laser optical fibers. In such a system, the elements generally include a laser source for generating laser energy to be provided to one of a plurality of laser probes couplable thereto. Each laser probe includes an optical fiber, including a fiber optic core, adapted to direct laser radiation from the laser source, through the fiber, and to a desired the treatment area. The system further includes a laser management system for managing the laser source. The management system includes a control system configured to adjust laser energy output from the laser source to any given laser probe to maintain a consistent level of laser radiation delivered to the target area, despite variation in the fiber optic core of any given laser probe.

Accordingly, the system of various embodiments may be able to compensate for wide range of variations across a plurality of laser probes by simply adjusting output of the laser source to account for such variations. In turn, the manufacture tolerance for optical fibers improves as less precision is required during the manufacturing process, which reduces overall costs. Furthermore, by fine tuning of the laser output, the laser radiation is maintained at a consistent wavelength, ensuring that the target area is treated as intended and patient safety is maintained.

The system of various embodiments may be suited for intraocular procedures in which laser treatment of target tissues is desired. In particular, the laser source, laser management system, and laser probes of various embodiments may be used for treating glaucoma and useful in performing a laser trabeculostomy. However, it should be noted that the system consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

Figure 36:
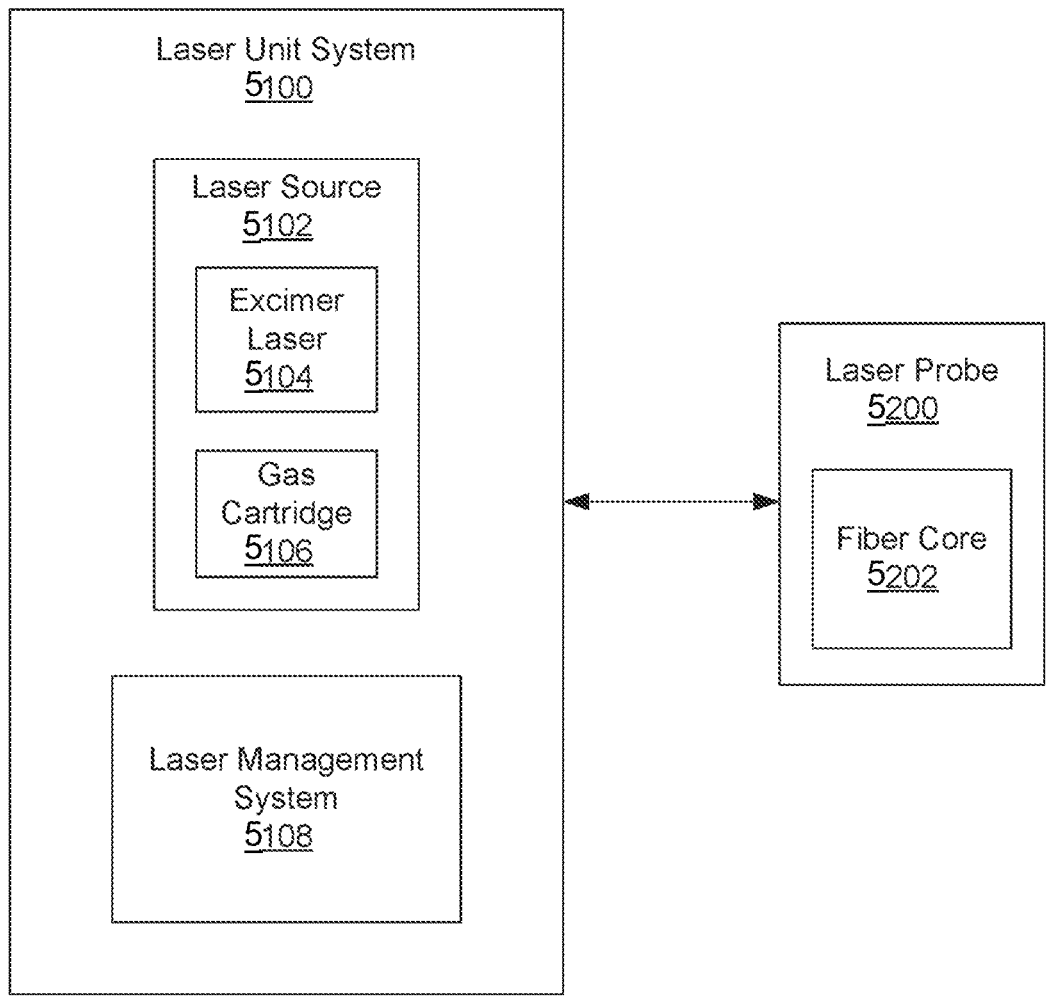
FIG. 36 diagrams an excimer laser system of the present disclosure.

FIG. 36 diagrams an excimer laser system, including a laser unit system 5100 and a laser probe 5200 to be attached to the laser unit system 5100. The system 5100 includes a laser source 5102, and a laser management system 5108. The laser probe 5200 includes a fiber core 5204. As will be described in greater detail herein, many of the components of the laser unit system 5100 may be contained in a housing, such as a moveable platform, to be provided in a setting in which the procedure is to be performed (e.g., operating room, procedure room, outpatient office setting, etc.) and the probe 5200 may connect to the housing for use during treatment. Upon coupling the probe 5200 to the housing, the fiber core 5202 is coupled to the laser source 5102 and adapted to direct laser radiation from the laser source 5102, through the fiber, and to the treatment area.

The laser source 5102 includes an excimer laser 5104 and a gas cartridge 5106 for providing the appropriate gas combination to the laser 5104. The excimer laser 5104 is a form of ultraviolet laser that generally operates in the UV spectral region and generates nanosecond pulses. The excimer gain medium (i.e., the medium contained within the gas cartridge 5106) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 5104 of the present system 5100 is an XeCl excimer laser and emits a wavelength of 308 nm.

Figure 37:
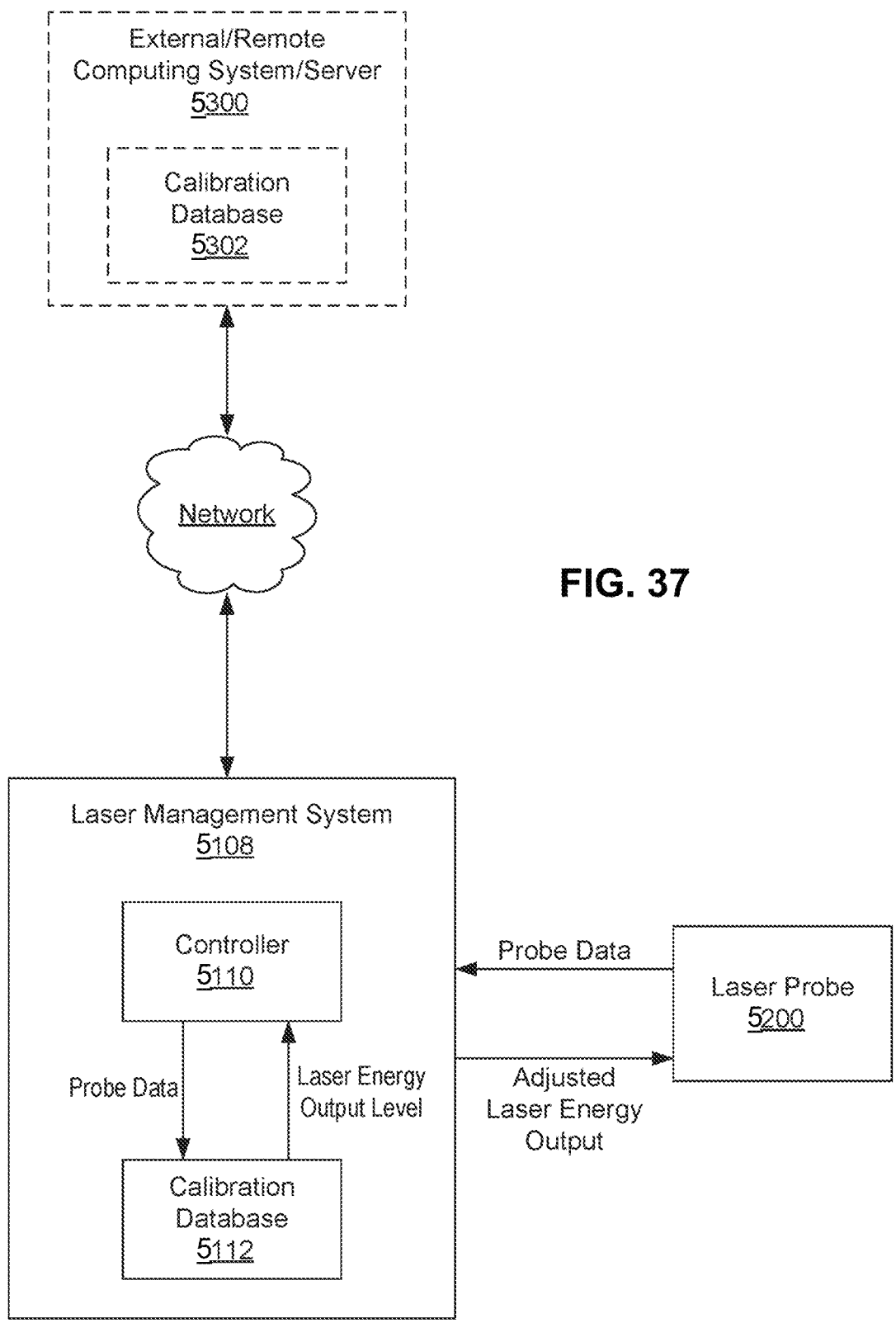
FIG. 37 diagrams the excimer laser system of the present disclosure and how the system may be used to calibrate laser output to compensate for increased variation in optical fibers of laser probes.

The laser management system 5108 manages the laser source 5102. In particular, as shown in FIG. 37, the laser management system 5108 includes a controller 5110 (also referred to herein as a "control system 5110"). The controller 5110 provides an operator (i.e., surgeon or other medical professional) with control over the output of laser signals (from the laser source 5102 to the fiber core 5202) and, in turn, control over the transmission of laser energy from the fiber core 5202 of the probe 5200. However, prior to providing an operator with control over laser output, the laser management system 5108 provides a calibration process in which laser energy output from the laser source 5102 to the laser probe 5200 is calibrated to maintain a consistent level of laser radiation delivered from the probe 5200 to the target area, despite any variation in the fiber optic core 5202 of the probe 5200.

Figure 38:
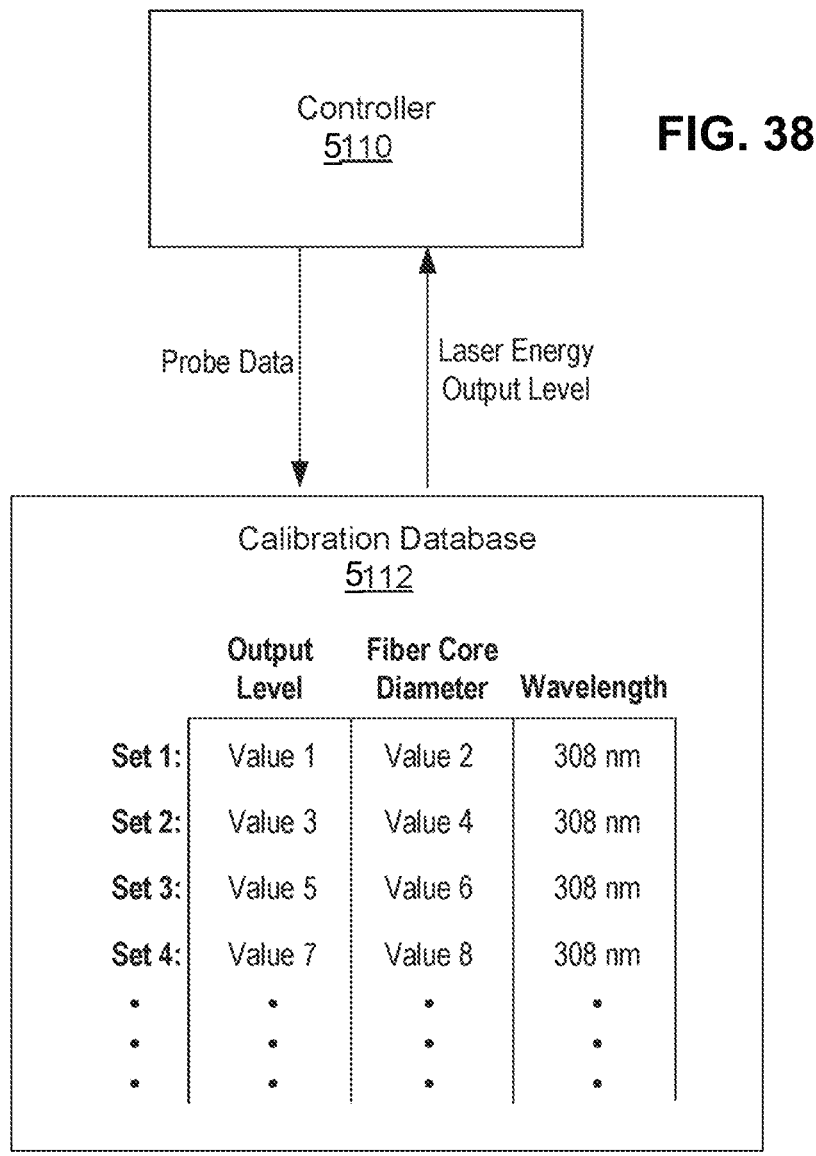
FIG. 38 diagrams a process of calibrating laser output, including adjustment of laser energy output from the laser source to a laser probe to account for variation in the fiber optic core of the laser probe.

FIG. 37 diagrams the laser unit system 5100 and calibration of laser output to a laser probe 5200 to be used with the system 5100 to account for variation in the fiber optic core of the laser probe 5200. FIG. 38 diagrams a process of calibrating laser output, including adjustment of laser energy output from the laser source to a laser probe to account for variation in the fiber optic core 5202 of the laser probe 5200.

As part of the initial setup, the controller 5110 receives data associated with a laser probe coupled to the laser source 5102. In this instance, data from laser probe 200 is provided to the controller 5110. This data may be manually entered (via a user interface provided on the system 5100) or may be automatically read from readable device or label on the probe 200 via an associated reader of the system 5100. The data may include physical characteristics of the probe 5200, including, but not limited to, physical dimensions of the fiber optic core 5202, one or more measured values or physical properties of the fiber optic core 5202, and physical dimensions and/or measured values or physical properties of other components of the probe 5200. In one embodiment, the data includes a diameter of the fiber optic core 5202.

The data is then analyzed by the controller 5110 and, based on the analysis, a determination of an optimum level of laser energy output from the laser source 5102 is made. The analysis is based on a correlation of the laser probe data, such as specific dimensions of the fiber optic core, with calibration data. The calibration data is stored in a database, either a local database (i.e., calibration database 5112) forming part of the laser unit system 5100, or a remote database hosted via a remote server 5300 (i.e., calibration database 5302). For example, in some embodiments, the system 5100 may communicate and exchange data with a remote server 5300 over a network. The network may represent, for example, a private or non-private local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web).

The calibration data may generally include a plurality of sets of values, wherein each set of values may include a laser energy output level from the laser source, a diameter of a fiber optic core of a laser probe to receive the laser energy output level, and the resulting wavelength value of laser radiation emitted from the delivery tip of the laser probe. The resulting wavelength value of laser radiation emitted from the delivery tip may remain constant, regardless of the diameter of the fiber optic core. In such an embodiment, the laser management system (i.e., the control system) automatically adjusts the laser energy output level from the laser source (i.e., increases or decreases output level) for any given diameter of a fiber optic core so as to maintain the emission of laser radiation upon a target area at a consistent wavelength, despite variation in the diameter of fiber optic cores from the plurality of laser probes.

The controller 5110 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 5104 may include a hardware processor coupled to non-transitory, computer-readable memory containing instructions executable by the processor to cause the controller to carry out various functions of the laser system 5100 as described herein, including the calibration process. For example, the controller 5110 may include custom, proprietary, known and/or after-developed statistical analysis code (or instruction sets), hardware, and/or firmware that are generally well-defined and operable to receive two or more sets of data and identify, at least to a certain extent, a level of correlation and thereby associate the sets of data with one another based on the level of correlation.

The excimer laser unit 100 of FIG. 4 may be similar to, may be used as (in whole or in part) as the laser unit system 5100 and/or the laser source 5102. In various embodiments, the laser source 5102 (including the excimer laser 5104 and gas cartridge 5106) and laser management system 5108, including the controller 5110, may be contained within the housing 402. An operator may manually input the laser probe data via the interactive user interface to thereby provide such data to the laser management system 5108 and controller 5110. However, in various embodiments, the data may be automatically read from a readable device or code (e.g., optically and/or electronically readable) and/or a label on the probe 5200 via an associated reader of the system 5100.

Figure 39:
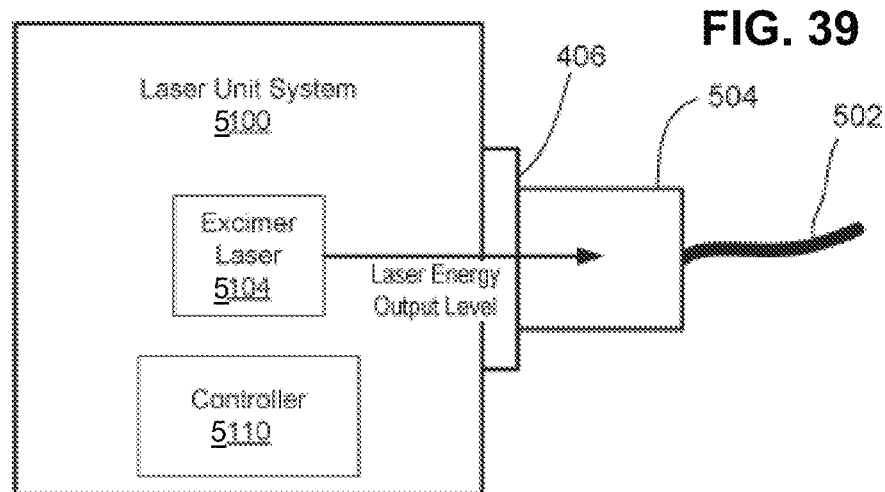
FIG. 39 shows an embodiment of a probe for use with the excimer laser system.

A probe, such as those shown in FIGS. 4-6, 21, 24, 29, and/or 32 may be used with the excimer laser system 5100. For example, FIG. 39 shows an embodiment of a laser probe 500 attached to a laser unit system 5100. As previously described, upon attachment of the laser probe 500 to the system 5100 (i.e., coupling between the connection assembly 504 of the probe 500 and connection port 406 of the system 400), the laser management system 5108 (including the controller 5110) perform calibration processes prior to use of the probe 500. In particular, data associated with characteristics of the probe 500, such as the diameter of the fiber optic core, is provided to the laser management system 5108. The data is then analyzed by the controller 5110 and, based on the analysis, a determination of an optimum level of laser energy output from the laser source is made. The optimum level of laser energy output from the laser source may be based on a correlation of the laser probe data, such as specific dimensions of the fiber optic core, with calibration data. The controller 5110 automatically adjusts the laser energy output level from the laser source (i.e., increases or decreases output level) for any given diameter of a fiber optic core so as to maintain the emission of laser radiation upon a target area at a consistent wavelength, despite variation in the diameter of fiber optic cores from the plurality of laser probes.

Accordingly, the system of the various embodiments is able to compensate for wide range of variations across a plurality of laser probes by simply adjusting output of the laser source to account for such variations. In turn, the manufacture tolerance for optical fibers improves as less precision is required during the manufacturing process, which reduces overall costs. Furthermore, by fine tuning of the laser output, the laser radiation is maintained at a consistent wavelength, ensuring that the target area is treated as intended and patient safety is maintained.

Combination Treatment Using ELT

In glaucoma, there is a build-up of fluid known as aqueous humor in the anterior chamber of the eye. The fluid normally drains from the eye in an area known as the trabecular meshwork, typically flowing through Schlemm's canal in the trabecular meshwork. However, when an individual suffers from glaucoma, the fluid build-up causes elevated intraocular pressure (TOP). The increased pressure gradually leads to damage of the optic nerve and causes irreversible vision loss.

Traditional methods of treating glaucoma manage the condition by decreasing the IOP or producing less aqueous humor. Traditional glaucoma treatment includes pharmaceutical treatments, laser treatments, surgical treatments, and combinations thereof. Pharmaceutical treatments do not provide a permanent solution and instead manage the condition by decreasing production of the fluid or increasing drainage of the fluid to lower IOP. Laser treatments are also used to reduce the TOP by increasing fluid outflow or decreasing fluid production. However, laser and pharmaceutical treatments often are not effective in treating advanced stages of glaucoma. Thus, individuals suffering from glaucoma are also treated by surgical procedures, such as inserting an implant into the eye to increase drainage. However, these procedures are accompanied by risks, such as dislodgment of the implant.

The various embodiments provide methods for combined treatment of glaucoma using excimer laser trabeculostomy (ELT). Methods include performing ELT on a subject having glaucoma who has previously undergone a failed treatment. Because glaucoma is a progressive disease, previous treatments may be rendered ineffective as the condition worsens. Therefore, glaucoma patients often endure several failed treatments. Methods of the various embodiments provide treatment of glaucoma using ELT and can be implemented even when previous treatment methods have failed. During the ELT procedure, a laser probe is positioned proximate to the Schlemm's canal to create perforations the trabecular meshwork and/or Schlemm's canal to immediately improve fluid drainage. The perforations can also increase outflow of aqueous humor and reduce pressure in the eye.

In various examples, the failed treatment is a traditional method of treating glaucoma, such as a prescribed medication or pharmaceutical treatment, laser treatment, surgical treatment, or combinations thereof. Typically, a prescribed medication or pharmaceutical treatment is a medicated eye drop, such as alpha agonists, beta blockers, carbonic anhydrase inhibitors, cholinergic agonists, prostaglandin/prostamide analogues, or combinations thereof. Examples of laser treatments include trabeculoplasty, iridotomy, iridectomy, and combinations thereof. Examples of trabeculoplasty include argon laser trabeculoplasty (ALT) and selective laser trabeculoplasty (SLT). Surgery is a traditionally a procedure of last resort after medical and laser therapies, due to relatively high complication rates and unpredictability of procedures such as trabeculectomies. Examples of surgical treatment include insertion of a shunt or implant, trabeculectomy, trabeculotomy, goniotomy, deep sclerectomy, viscocanalostomy, or combinations thereof.

An example is directed to providing glaucoma treatment to a subject who has been administered previous glaucoma treatments that have failed or have been rendered ineffective. For example, a pharmaceutical treatment may have been previously effective in treating the subject's glaucoma before the disease progressed to a state where the pharmaceutical treatment was rendered ineffective. The subject may have undergone a laser treatment, such as selective laser trabeculoplasty (SLT), for treatment of the glaucoma. SLT may have been effective in treating the glaucoma until the condition worsened. Various methods provide ELT as a treatment after the previously-administered treatments have failed or have been rendered ineffective, allowing for drainage of the fluid build-up in the anterior chamber. This includes a re-administration of ELT in the same or another part of the eye (quadrant).

In an example, a subject with advanced glaucoma was administered a prescription medication until the prescription was ineffective, SLT as a laser therapy until the SLT was ineffective, and implant of a stent, which has since become dislodged. Because the subject has advanced glaucoma, treatment methods such as pharmaceutical or existing laser therapy may not be effective in treating the condition. Moreover, because the surgical treatment resulted in a failed stent placement, the stent is not draining the build-up of aqueous humor in the anterior chamber of the eye. By providing ELT treatment according to various methods, perforations are created in the trabecular meshwork and/or Schlemm's canal, and the aqueous humor is allowed to drain. Thus, various embodiments are effective in draining the fluid build-up, even when previous treatments have failed.

In some embodiments, one or more previous treatments remain effective. In such instances, ELT is administered to provide combination treatment of glaucoma. Providing ELT in addition to other effective treatments creates increased drainage of the aqueous humor from the anterior chamber of the eye. For example, a subject having glaucoma that has undergone one failed treatment method, such as a pharmaceutical treatment, may be administered ELT and SLT as combination therapy. In some instances, such a combined treatment may be administered to the patient during the same surgical visit.

During the ELT procedure, a physician guides a delivery tip of a fiber probe through a corneal incision in the eye and towards the trabecular meshwork. In some examples, various embodiments further comprise administering anesthesia to the subject before making the incision and inserting the probe. Typically, the incision has a length of about ⅛ inch or smaller. In some examples, one or more sutures are used to close the incision after ELT treatment. The delivery tip is guided by the physician to a position proximate to the Schlemm's canal to create permanent perforations the trabecular meshwork and/or Schlemm's canal. Fluid drainage in the anterior chamber of the eye is immediately improved by the perforations created in Schlemm's canal and/or the meshwork by the excimer laser. The perforations can also increase outflow of aqueous humor and reduce pressure in the eye. In some cases, the physician uses a Gonio lens, endoscope, or other illumination source to aid in positioning the delivery tip of the fiber probe. Typically, a physician will use a gonio lens to intraoperatively observe a slight reflux hemorrhage as a quality criterion, thereby allowing effective positioning of the fiber at the trabecular meshwork to create a passageway into Schlemm's canal. A further quality criterion is minor reflux bleeding that can be observed intraoperatively, thus allowing effective positioning of the fiber at the trabecular meshwork to open Schlemm's canal.

Once the delivery tip is at a position proximate to the Schlemm's canal, a series of shots of laser energy are delivered to the trabecular meshwork. In an example, a 308-nm xenon-chloride ultraviolet excimer laser is used in various embodiments. The 308-nm xenon-chloride ultraviolet excimer laser causes minimal thermal damage compared with visible or infrared lasers. In some examples, the excimer laser is an encapsulated xenon chloride (XeCl) excimer laser such as the EXTRA LASER manufactured by MLase AG. Unlike argon and selective laser trabeculoplasty, ELT precisely excises tissue without causing thermal injury or scarring the surrounding tissue. Because ELT is a non-thermal procedure, tissue reactions in the trabecular meshwork are not shown or activated post-operatively. The lack of heat generation in ELT allows for a nearly absent activation of postoperative tissue reactions and provides long-term stability of the pressure-reducing effects.

Moreover, to avoid the corneal absorption of laser radiation, an optical fiber is used to deliver the energy. The delivery tip of the fiber probe comprises the optical fiber jacketed in metal, such as stainless steel. In some examples, the delivery tip is beveled (e.g., at 0°, 15°, 30°, and 45° with respect to the tip). The fiber probe comprises an optical fiber suitable for UV light that is embedded into a handheld laser applicator. For example, a FIDO LASER APPLICATOR manufactured by MLase AG may be used as the fiber probe.

To achieve easier drainage of the aqueous humor, which leads to reduced IOP, a total of about 10 ELT sites or perforations, each with about a 200 μm diameter, are lasered into the trabecular meshwork and/or Schlemm's canal. In an example, about 10 shots from excimer laser source are applied to each eye. In some examples, greater than about 10 shots are applied to each eye. In comparison, stents and implants have smaller individual diameters that are between about 80 μm to about 120 μm.

In some embodiments, the patient is administered an anesthetic before surgery. In some examples, the anesthesia is topical. In some examples, the anesthesia comprises anesthetic drops. In some instances, general anesthesia is administered to the patient. The eye is anesthetized first with eye drops and then an injection of anesthetic is administered around the eye. The anesthetic injection itself may cause some mild discomfort; a slight sensation of pressure as the anesthetic is delivered. The injection anesthetizes the eye, preventing not only pain but also excessive eye movement during surgery.

Various embodiments provide treatment of glaucoma using ELT after previously-administered treatments have failed or been rendered ineffective. Previous treatment methods include pharmaceutical treatments, laser treatments, surgical treatments, or combinations thereof. For example, a patient may have previously been prescribed medicated eye drops and may have undergone a selective laser trabeculoplasty (SLT) procedure, but the patient's condition has progressed to a point where those treatments are no longer effective. The various embodiments provide methods of treating the patient by administering ELT treatment to the glaucoma patient who has previously undergone failed treatments.

In various embodiments, the failed treatment is a prescribed medication or pharmaceutical treatment, laser treatment, surgical treatment, or combination thereof. Traditional methods for treating glaucoma include medicated drops, laser treatment, and surgical treatment. Surgery is a traditionally a procedure of last resort after medical and laser therapies, due to relatively high complication rates and unpredictability of procedures such as trabeculectomies.

Typically, a prescribed medication or pharmaceutical treatment is a medicated eye drop, such as alpha agonists, beta blockers, carbonic anhydrase inhibitors, cholinergic agonists, prostaglandin/prostamide analogues, or combinations thereof. Examples of laser treatments include trabeculoplasty, iridotomy, iridectomy, and combinations thereof. Examples of trabeculoplasty include argon laser trabeculoplasty (ALT) and selective laser trabeculoplasty (SLT). Examples of surgical treatment include insertion of a shunt or implant, trabeculectomy, trabeculotomy, goniotomy, deep sclerectomy, viscocanalostomy, or combinations thereof.

Medication is the most common early treatment for glaucoma, and pharmaceutical options include medicated eye drops, pills, or both. All medications available for the treatment of glaucoma must be taken regularly. Examples of the medicated eye drops include alpha agonists, beta blockers, carbonic anhydrase inhibitors, cholinergic agonists, and prostaglandin/prostamide analogues.

Alpha agonists, such as apraclondine and brimonidine, are used to reduce the production of fluid in the eye and to improve the flow of fluid out of the eye. The drops are typically used two or three times a day. Apraclonidine is for short-term use following laser treatment or to delay laser treatment. Brimonidine is licensed for the long-term treatment of glaucoma, but is contra-indicated for children under the age of two years. Side effects include a dry mouth, tiredness, and general weakness. Patients may develop a severe allergic reaction to the drops, causing the eye to become increasingly red, sore, and sticky. Alpha agonists include formulations of brimonidine (ALPHAGAN manufactured by Allergan, Inc.).

Beta blockers include betaxolol, carteolol, levobunolol, and timolol, and are used to reduce the production of fluid in the eye. The drops are used once or twice a day and are not typically prescribed for anyone susceptible to chest or breathing problems. Side-effects include slow pulse, dizziness, asthma, tiredness, depression, loss of libido, and impotence. Beta adrenergic blocking drops include timolol (TIMOPTIC manufactured by Bausch and Lomb and BETIMOL manufactured by Akorn, Inc.), levobunolol (BETAGAN manufactured by Allergan, Inc.), betaxolol (BETOPTIC manufactured by Alcon Laboratories Inc.), carteolol (OCUPRESS manufactured by Bausch and Lomb Pharmaceuticals Inc.), and metipranolol (OPTIPRANOLOL manufactured by Bausch & Lomb Pharmaceuticals, Inc.).

Carbonic anhydrase inhibitors, such as brinzolamide and dorzolamide, reduce production of fluid in the eye. The drops are used two or three times a day on their own, or twice a day if with another drop. Side-effects include redness of the eye, crusty eyelashes, fatigue, and a bitter taste in the mouth. The carbonic anhydrase inhibitors include oral agents acetazolamide (DIAMOX SEQUELS manufactured by Teva Pharmaceuticals USA, Inc.) and methazolamide (NEPTAZANE manufactured by Perrigo Company plc, Dublin Ireland) and the eyedrops brinzolamide (AZOPT manufactured by Alcon Laboratories Inc., a Novartis company, Novartis Pharmaceuticals Corporation, USA) and dorzolamide (TRUSOPT manufactured by Santen Pharmaceutical Co., Ltd.).

Cholinergic agonist drops, such as pilocarpine, are used to improve the flow of fluid out of the eye. When using cholinergic agonist drops, the usual fluid flow route is improved. Drops are used three or four times a day. Miotic drops include pilocarpine hydrochloride solution manufactured by Akorn, Inc.

Prostaglandin/prostamide analogues include bimatoprost, latanoprost, tafluprost, and travoprost. The drops are used to improve the fluid flow out of the eye through a different way from the usual one. The drops are used once a day. Side effects include a pink eye that typically improves over a period of time, an iris that darkens in color, longer and darker eyelashes, and darkened skin around the orbit of the eye. Examples of prostanoid FP-receptor (sensitive to prostaglandin F) agonists include latanoprost (XALATAN manufactured by Pfizer Inc.), bimatoprost (LUMIGAN manufactured by Allergan, Inc.), travoprost (TRAVATAN Z manufactured by Novartis Pharmaceuticals Corporation), unoprostone (RESCULA manufactured by Sucampo Pharma Americas, LLC), and tafluprost (ZIOPTAN manufactured by Akorn, Incorporated).

Several laser treatments are used in the treatment of glaucoma. Different laser treatments are used to treat a number of different types of glaucoma. In open angle glaucoma, laser treatment is used to reduce the intraocular pressure (TOP) by increasing outflow of aqueous fluid from the eye (laser trabeculoplasty) or to decrease the formation of aqueous fluid (cyclophotocoagulation). In narrow angle glaucoma, laser iridotomy is used to make a small hole in the iris to improve fluid outflow or iridoplasty is performed to tighten the iris and open the drainage angle.

Argon laser trabeculoplasty (ALT) is used to treat chronic open angle glaucoma. ALT was first performed with an argon laser, although lasers used today are frequency doubled YAG lasers that perform a similar function. Typically, the trabecular meshwork is targeted, treating half of the eye in a single session. If necessary, the other half is treated later. The treatment requires eye drop anesthesia. Treatment may be used in place of eye drops, but typically is used as an adjunct to continuing treatment with drops. A different type of laser therapy or surgery may be required, as the effect of ALT may wear off after a few years. Several follow-up appointments are required after treatment in order to monitor TOP and inflammation in the patient. Typically, most patients require anti-glaucoma drops in the long-term to control the TOP at the desired level.

Selective laser trabeculopalsty (SLT) is used to treat chronic open angle glaucoma. SLT is similar to ALT, but uses a gentler laser beam of larger size. In SLT, a laser is directed at the trabecular meshwork, but uses a laser with a lower power than ALT treatment. The best SLT results are produced when all 360 degrees of the trabecular meshwork is treated at once. Unlike ALT, SLT can be repeated if the effect wears off. Several follow-up appointments are required after treatment in order to monitor TOP and inflammation in the patient. Typically, most patients require anti-glaucoma drops in the long-term to control the TOP at the desired level.

Trans-scleral photocoagulation, cyclodiode or diode laser cycloablation, is used to treat chronic open angle glaucoma. A laser is used to target the ciliary body that produces the fluid. A general anesthetic or a local anesthetic injection is often required for treatment. Trans-scleral photocoagulation can be repeated if the TOP is not considered low enough or the effect wears off with time. Cyclodiode is also recommended in a number of other forms of glaucoma where very high IOPs occur and traditional surgery is contraindicated or impossible. Patients undergoing cyclodiode often require strong painkillers after the treatment. Several follow-up appointments are required after treatment in order to monitor TOP and inflammation in the patient. Typically, most patients require anti-glaucoma drops in the long-term to control the TOP at the desired level.

Laser iridotomy is used to treat closed and narrow angle glaucoma. In laser iridotomy, a small hole is made with a Yag laser in order to relieve a narrow or closed angle. The fluid passes through the hole, inducing the iris to fall back away from the drainage meshwork, and the fluid drains freely through the meshwork. Numbing eye drops are typically administered as an anesthetic. However, in some eyes the iris does not fall back as desired, thus requiring other treatments. Even with a good iris position, medication or surgery may still be required to control the TOP. Post-laser drops are required, usually in the form of steroids, and anti-glaucoma drops may be necessary temporarily or indefinitely.

Peripheral iridoplasty is used to treat closed and narrow angle glaucoma. Peripheral iridoplasty may be used when the iris has not fallen back in an eye that has undergone a laser iridotomy. An argon or frequency doubled Yag laser is applied to the outer margins of the iris to shrink the iris away from the drainage meshwork and open the drainage angle. Anesthesia other than numbing drops may be required. Post-laser drops are required, usually in the form of steroids, and anti-glaucoma drops may be necessary temporarily or indefinitely.

Several surgical treatments are available to treat glaucoma. However, surgical options are often a last resort and are reserved for late-stage glaucoma patients, after pharmaceutical and laser treatment options have proved ineffective in treating the condition.

Aqueous shunts are used to reduce the intraocular pressure (TOP) in glaucoma by draining the fluid from inside the eye to a small blister or bleb behind the eyelid. Aqueous shunts have various other names such as tube implants, glaucoma tube shunts, glaucoma drainage devices, and glaucoma drainage implants. Two types of shunts commonly used include the Ahmed Glaucoma Valve (manufactured by New World Medical, Rancho Cucamonga, CA, USA) and the Baerveldt Glaucoma Implant (manufactured by Advanced Medical Optics, Inc., Santa Ana, CA, USA). The shunts are made of a small silicone tube (less than 1 mm in diameter) attached to a plate. The tube takes the aqueous humor from inside the eye and drains it to the plate which sits on the white of the eye (sclera). The plate sits under the skin of the eye conjunctiva), behind the eyelid.

Trabeculectomy is a surgical procedure used to treat glaucoma and is sometimes referred to as filtration surgery. During a trabeculectomy, a physician removes a piece of tissue in the drainage angle of the eye to create an opening. The opening is partially covered with a flap of tissue from the sclera, the white part of the eye, and the conjunctiva, the clear thin covering over the sclera. The newly-created opening allows fluid to drain out of the eye, bypassing the clogged drainage channels of the trabecular meshwork. A bleb is formed when fluid flows through the new drainage opening and the tissue over the opening rises to form a little blister or bubble.

Trabeculotomy is a surgical procedure much like trabeculectomy. A physician removes a piece of tissue in the eye's drainage angle to create an opening. The newly-created opening allows fluid to drain out of the eye. Trabeculotomy surgery is for children only.

During a goniotomy, a physician uses a goniolens to see the structures of the front part of the eye, or anterior chamber. The physician makes an opening in the trabecular meshwork, the group of tiny canals located in the drainage angle where fluid leaves the eye. The newly-created opening allows fluid to flow out of the eye. Goniotomy surgery is for children only.

Deep sclerectomy is a non-penetrating surgical procedure used for treatment of open angle glaucoma. The deep sclerectomy procedure involves removing the inner wall of Schlemm's canal and juxta-canalicular trabecular meshwork, the structures responsible for most of the outflow resistance in open angle glaucoma. The aqueous outflow is enhanced, and a trabeculo-Descemet's membrane (TDM) is left intact to control aqueous outflow through the filtration site.

In viscocanalostomy, tissue flaps are cut in the conjunctiva and the sclera to expose a portion of the drainage canal (Schlemm's canal). The procedure involves production of superficial and deep scleral flaps, excision of the deep scleral flap to create a scleral reservoir, and unroofing of Schlemm's canal. A high-viscosity elastic gel is injected in Schlemm's canal to open and enlarge the canal to allow increased fluid flow out of the anterior chamber. For example, the high-viscosity viscoelastic may comprise sodium hyaluronate.

The tissue flaps are then closed. For example, the superficial scleral flap may be sutured water tight, trapping the viscoelastic until healing takes place.

Previously-attempted treatment methods have proved ineffective at treating glaucoma in a patient. Embodiments herein use an excimer laser to permanently perforate the Schlemm's canal and/or trabecular meshwork to create an internal outflow channel. Such ablation with excimer lasers causes almost no thermal damage, thereby minimizing inflammation and formation of scar tissue. In contrast, because of inflammatory and healing responses, other lasers, such as ruby and argon lasers, cannot achieve a permanent perforation of the trabecular meshwork. Therefore, various embodiments use ELT to reestablish outflow of fluid from the eye without inciting a healing response at the target tissue. Due to the lack of inflammation and scar tissue formation, methods of treatment of various embodiments require less recovery time than traditional surgical methods, such as placement of implants.

In embodiments, multiple shots from an excimer laser are administered to the patient in order to create perforations in the trabecular meshwork and/or Schlemm's canal. ELT converts trabecular meshwork tissue into gas by photoablation. By permanently perforating Schlemm's canal and/or the trabecular meshwork, built-up fluid in the eye is immediately allowed to drain. Moreover, because the perforations allow for increased outflow of aqueous humor and fluid drainage, subsequent vision loss from damage to the optic nerve due to any build-up is thereby avoided.

Figure 40:
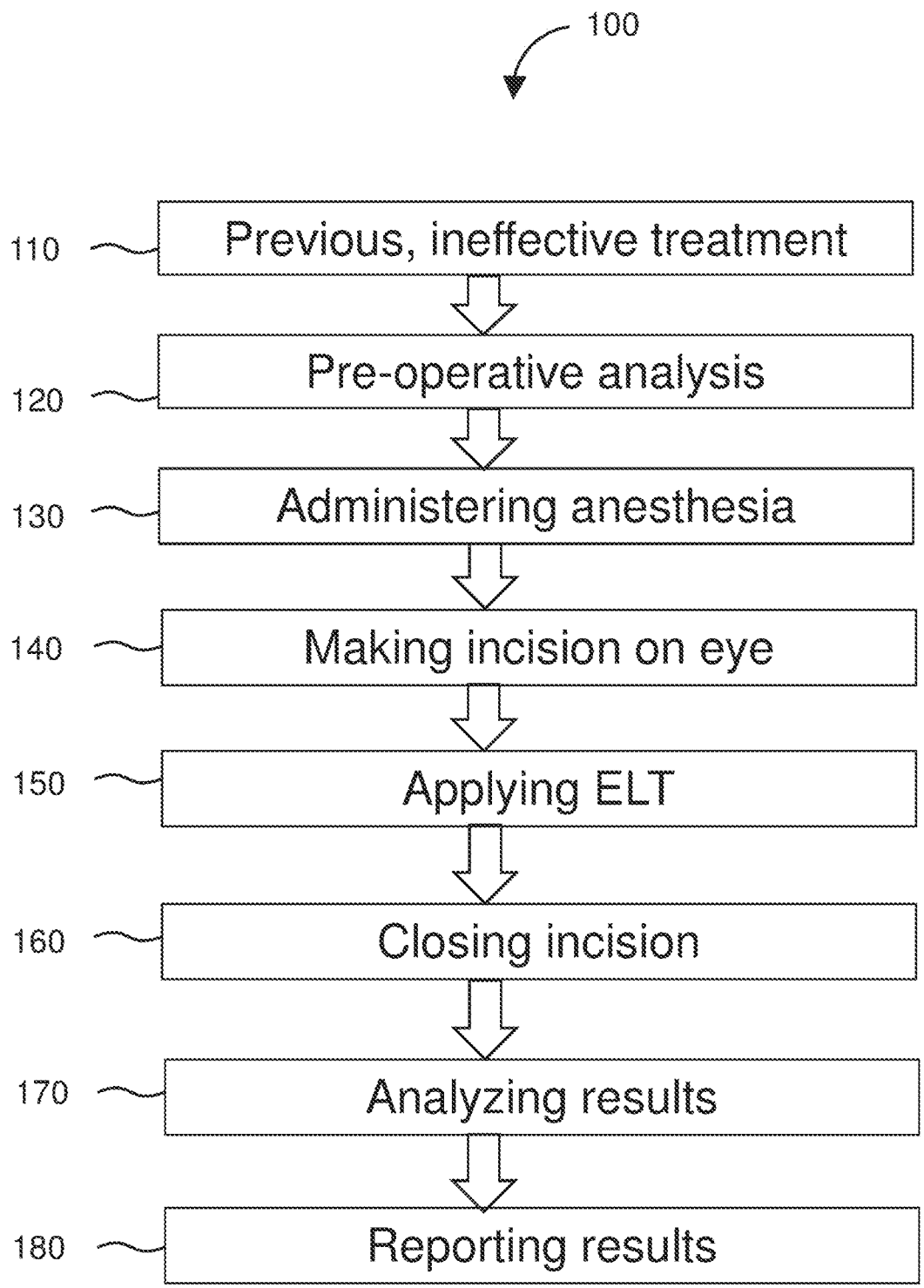
FIG. 40 is a flowchart of an embodiment of methods of applying ELT after a previous, ineffective treatment.

FIG. 40 shows a flowchart of an embodiment 4100. Various embodiments are directed to treating a patient having glaucoma with ELT. In various embodiments, the energy shots delivered from the excimer laser are at a position proximate to the Schlemm's canal. Various embodiments are performed after a patient having glaucoma has been 4110 administered previous, ineffective treatments. Treatments other than ELT include traditional pharmaceutical, laser, and surgical treatments. For instance, pharmaceutical treatment methods involve pills, eyedrops, or both. Typically, a prescribed medication or pharmaceutical treatment is a medicated eye drop, such as alpha agonists, beta blockers, carbonic anhydrase inhibitors, cholinergic agonists, prostaglandin/prostamide analogues, or combinations thereof. Examples of laser treatments include trabeculoplasty, iridotomy, iridectomy, and combinations thereof. Examples of trabeculoplasty include argon laser trabeculoplasty (ALT) and selective laser trabeculoplasty (SLT). Examples of surgical treatment include insertion of a shunt or implant, trabeculectomy, trabeculotomy, goniotomy, deep sclerectomy, viscocanalostomy, or combinations thereof.

In various embodiments, ELT is administered even if other treatments have been previously administered and are ineffective. For example, if a shunt was placed in a subject's eye and has since become dislodged, providing ELT treatment is still possible. The provided ELT treatment will allow drainage of the build-up of fluid in the eye by providing permanent perforation of the Schlemm's canal and/or trabecular meshwork.

Methods of various embodiments include 4120 pre-operative analysis, such as diagnosis of the eye condition, determination of course of action based on previously-failed treatment methods, inspection and/or visualization of the anterior chamber of the eye to aid in placement of the laser probe, and analysis of number of laser shots needed for treatment. In various embodiments, excimer laser trabeculostomy (ELT) is used to treat glaucoma.

The method includes 4130 administering anesthesia to the patient. Topical anesthesia is commonly employed, typically by the instillation of a local anesthetic such as tetracaine or lidocaine. Lidocaine and/or a longer-acting bupivacaine anesthetic may be injected into the area surrounding (peribulbar block) or behind (retrobulbar block) the eye muscle cone to more fully immobilize the extraocular muscles and minimize pain sensation. Optionally, a facial nerve block may be performed using lidocaine and bupivacaine to reduce lid squeezing. In some cases, such as for children, patients with traumatic eye injuries, and nervous or uncooperative patients and animals, general anesthesia is administered with cardiovascular monitoring. To prepare the area for surgery, proper sterile precautions must be taken, including use of antiseptics like povidone-iodine and employment of sterile drapes, gowns, and gloves. In some cases, an eye speculum is inserted to keep the eyelids open.

A physician 4140 makes a small incision on the eye of the patient. Before the ELT procedure is performed, a small incision is made in the cornea of the eye to allow introduction of the laser probe. Typically, the incision is about ⅛ inch or smaller. During the ELT procedure, a physician guides the delivery tip of the fiber probe through a corneal incision in the eye and towards the trabecular meshwork. The delivery tip is guided by the physician to a position proximate to the Schlemm's canal. A Gonio lens, endoscope, and/or illumination source may be used by the physician to aid in positioning the delivery tip. By providing a laser probe at a position proximate to the Schlemm's canal, or crosswise to the Schlemm's canal, the laser is delivered to a greater amount of surface area than if the laser was in a parallel or perpendicular position to the Schlemm's canal, resulting in more perforation from fewer laser shots. Thus, arrangement of the delivery tip at a position proximate to the Schlemm's canal achieves optimal photoablation and perforation formation in the meshwork and/or Schlemm's canal for drainage of fluid. The orientation and positioning of the delivery tip is critical when creating perforations in the tissue, as achieving placement of perforations in the meshwork relative to Schlemm's canal provides optimal drainage.

Once the delivery tip is at a position proximate to the Schlemm's canal, the physician 4150 applies ELT treatment to the patient by delivering a series of shots of laser energy to the trabecular meshwork and/or Schlemm's canal. The physician applies pulsed photoablative energy to create ELT sites, or perforations, in the trabecular meshwork and/or Schlemm's canal. In some examples, a physician creates 10 ELT sites in an eye of the patient. In some examples, the physician creates greater than 10 ELT sites. A small amount of bloody reflux from Schlemm's canal confirms each opening. The fiber probe is removed from the eye. Notably, the TOP decreases immediately after administering the ELT procedure.

After applying ELT treatment, a physician 4160 closes the incision. Typically, a physician uses sutures to close the incision. Some physicians place a suture in the incision and other physicians reserve a suture for when there is persistent leakage.

Methods of the various embodiments include 4170 analyzing post-operative results and 4180 reporting results and/or scheduling a post-operative follow-up appointment with the patient after surgery. For example, the physician's analysis may include observing a small amount of bloody reflux from Schlemm's canal to confirm each opening. By observing the bloody reflux and drainage of aqueous humor, the physician is able to immediately verify the effectiveness of the laser treatment. In turn, the physician may report the results to the patient, prescribe post-operative medication, such as topical antibiotics and steroid drops, and schedule a follow-up post-operative visit with the patient. For example, topical antibiotics and steroid drops are used by the patient for 1 to 2 weeks post-operatively.

Figure 41:
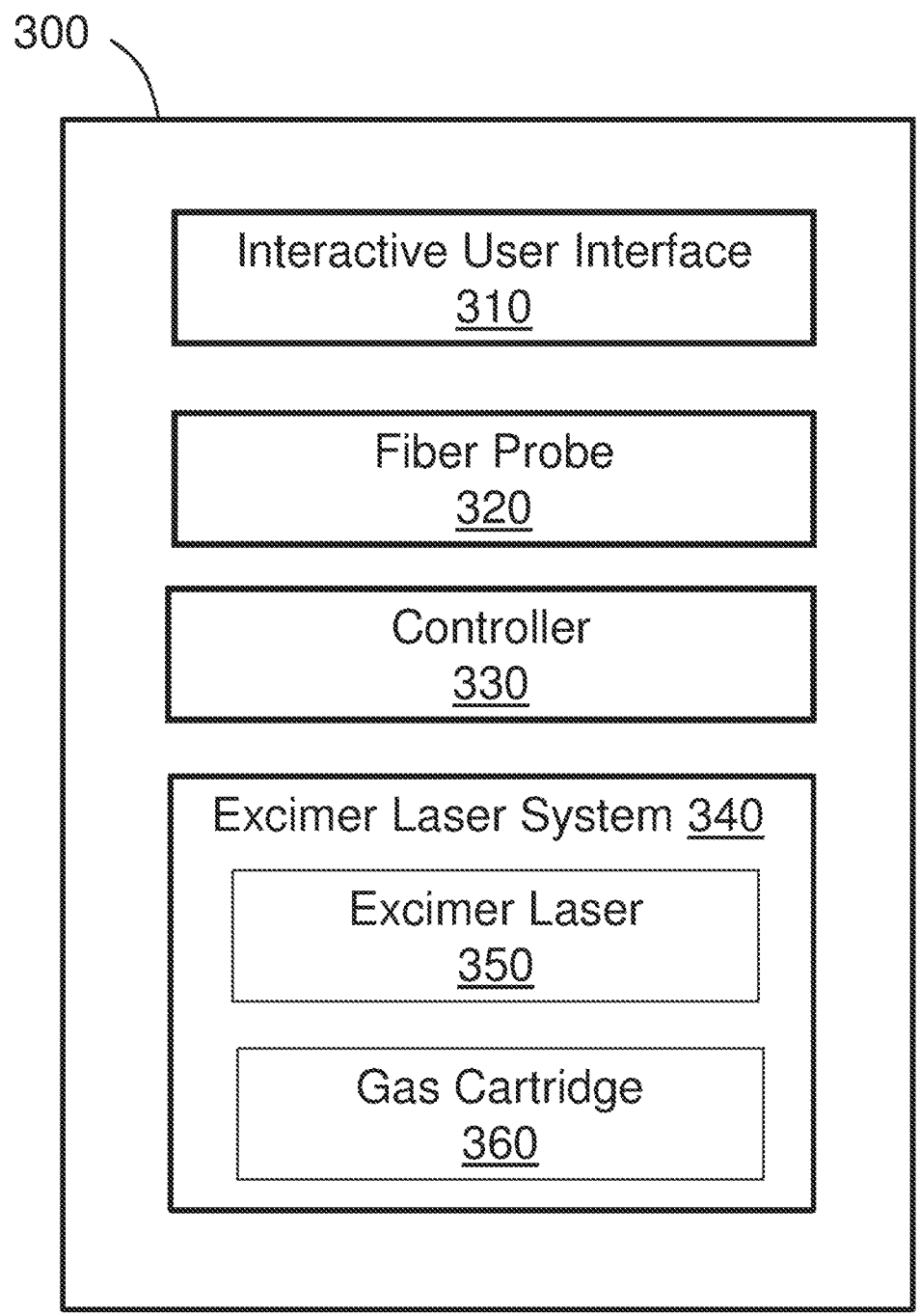
FIG. 41 shows an embodiment of an ELT system with an interactive user interface.

A system such as those shown in FIGS. 3-6, 21-33, and/or 36-39 may be used in various embodiments. Such a system may include the components shown in FIG. 41. FIG. 41 is a diagram of a system 6300 for treating glaucoma according to the various embodiments. The treatment system 6300 comprises an interactive user interface 6310 (example user interface 410), a fiber probe 6320 (examples of fiber probes 102, 104, 500, 4200, 5200), controller 6330, and an excimer laser trabeculostomy (ELT) system 6340. The excimer laser system 6340 comprises an excimer laser 6350 and gas cartridge 6360. The excimer laser system 6340, interactive user interface 6310, and fiber probe 6320 are communicatively coupled to the controller 6330. Moreover, the excimer laser system 6340 may be contained in a housing that includes an interactive user interface, and a fiber probe may connect to the housing for use during ELT treatment.

The controller 6330 has a processor. The processor generally includes a chip, such as a single core or multi-core chip, to provide a central processing unit (CPU), such as a chip from Intel or AMD. The controller 6330 provides an operator (i.e., physician, surgeon, or other medical professional) with control over the treatment system 6300, including programming of the fiber probe, output of laser signals, and control over the transmission of laser energy from the laser source 6350 to the fiber probe 6320 that delivers the laser transmission.

The controller 6330 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 6330 may include a hardware processor coupled to non-transitory, computer-readable memory containing instructions executable by the processor to cause the controller to carry out various functions of the treatment system 6300 as described herein, including controlling the laser delivery and using the interactive user interface 6310 to program the number of laser shots deliverable by the fiber probe 6320.

The laser system 6340 includes an excimer laser 6350 and a gas cartridge 6360 for providing the appropriate gas combination to the laser 6350. The excimer laser 6350 is a form of ultraviolet laser that generally operates in the UV spectral region and generates nanosecond pulses. The excimer gain medium (i.e., the medium contained within the gas cartridge 6360) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 6350 of the present system 6300 is an XeCl excimer laser and emits a wavelength of 308 nm.

Methods of Transverse Placement in Elt

A leading cause of irreversible blindness is glaucoma. Typically, fluid flows freely through the anterior chamber of the eye and exits through a drainage system that includes the trabecular meshwork and Schlemm's canal. When an individual suffers from glaucoma, a blockage in the trabecular meshwork or Schlemm's canal prevents the fluid from draining and results in increased pressure in the eye. If left untreated, the increased pressure in the eye damages the optic nerve, leading to gradual vision loss and eventual blindness.

Traditional methods of treating glaucoma include pharmaceutical treatments, laser treatments, surgical treatments, or combinations thereof to lower pressure in the eye. Pharmaceutical treatments, such as medicated drops, and laser treatments, such as selective laser trabeculoplasty (SLT), often are not effective in treating advanced stages of glaucoma. Invasive surgical treatments, such as placement of implants or drainage stents, are used to treat advanced stages of glaucoma. However, the invasive surgical treatments have drawbacks and require great precision to avoid dislodgement of the implant. For example, if a stent is not placed properly on the first attempt, the stent may be difficult to place at all.

The various embodiments provide treatment of glaucoma using excimer laser trabeculostomy (ELT). During the ELT procedure, a laser probe is positioned proximate to the Schlemm's canal to create perforations in the trabecular meshwork and/or Schlemm's canal that form a line that is transverse to the Schlemm's canal. By permanently perforating Schlemm's canal and/or the trabecular meshwork, built-up fluid in the anterior chamber of the eye is immediately allowed to drain. Arrangement of the laser probe at a position proximate to Schlemm's canal provides optimum results by providing a greater amount of surface area for photoablation by the laser. By applying the laser at a position proximate to Schlemm's canal, each laser shot provides photoablation of a greater amount of surface area, resulting in a greater perforation from fewer laser shots.

In open-angle glaucoma (OAG), the obstruction of fluid outflow at the trabecular meshwork and inner wall of Schlemm's canal is the primary cause of elevated intraocular pressure (TOP). The various embodiments use an excimer laser to perforate the trabecular meshwork and/or Schlemm's canal to create an internal outflow channel, increasing drainage of the fluid known as aqueous humor from the anterior chamber of the eye. The perforations also increase flow of aqueous humor and reduce pressure in the eye.

Methods of the various embodiments use ELT to reestablish outflow of fluid from the anterior chamber of the eye without inciting a healing response at the target tissue. ELT converts trabecular meshwork tissue into gas by photoablation. Ablation with excimer lasers causes almost no thermal damage, thereby minimizing inflammation and formation of scar tissue. Unlike argon and selective laser trabeculoplasty procedures, ELT precisely excises tissue without causing thermal injury or scarring the surrounding tissue. Moreover, other lasers, such as ruby and argon lasers, cannot achieve a permanent perforation of the trabecular meshwork because of inflammatory and healing responses. Due to the lack of inflammation and scar tissue formation, methods of the various embodiments require less recovery time than traditional laser treatments or surgical treatments, such as placement of implants.

During the ELT procedure, a physician guides a delivery tip of a fiber probe through a corneal incision in the eye and towards the trabecular meshwork. In some embodiments, methods of the various embodiments comprise administering anesthesia to the subject before making the incision and inserting the probe. Typically, the incision has a length of about ⅛ inch or smaller. The delivery tip is guided by the physician to a position proximate to the Schlemm's canal. In various embodiments, the physician uses a light source such as a Gonio lens, endoscope, or other illumination source to aid in positioning the delivery tip. Furthermore, the light source aids the physician in verifying the effectiveness of the laser treatment by visualizing drainage of the aqueous humor and bloody reflux emitted during the treatment.

Once the delivery tip is at a position proximate to the Schlemm's canal, the physician delivers a series of shots of laser energy to the trabecular meshwork, and the perforations may form a line, curve, etc. that is transverse to Schlemm's canal (e.g., the perforations may be at different heights of the Schlemm's canal to ensure a portion of the trabecular meshwork that is adjacent to Schlemm's canal is perforated). Thus, arrangement of the delivery tip at successive positions that are transverse to the Schlemm's canal achieves optimal photoablation and perforation formation in the meshwork and/or Schlemm's canal. The creation of a plurality of perforations therefore leads to a higher likelihood of immediate drainage of aqueous humor from the anterior chamber of the eye, and therefore a successful procedure and treatment of glaucoma.

ELT treatment creates long-term openings that connect the anterior chamber of the eye directly to Schlemm's canal using an excimer laser. Various embodiments use a 308-nm xenon-chloride ultraviolet excimer laser, which causes minimal thermal damage compared with visible or infrared lasers. In various embodiments, the excimer laser is an encapsulated xenon chloride (XeCl) excimer laser such as the EX TRA LASER manufactured by MLase AG. Moreover, to avoid the corneal absorption of laser radiation, an optical fiber is used to deliver the energy from the excimer laser. The delivery tip of the fiber probe comprises the optical fiber jacketed in metal, such as stainless steel. In some examples, the delivery tip is beveled (e.g., at 0°, 15°, 30°, and 45° with respect to the tip). The fiber probe comprises an optical fiber suitable for UV light that is embedded into a handheld laser applicator. For example, a FIDO LASER APPLICATOR manufactured by MLase AG may be used as the fiber probe.

To achieve easier drainage of the aqueous humor in order to reduce IOP, a total of about 10 ELT perforations, each having a diameter of about 200 μm, are lasered into the trabecular meshwork and/or Schlemm's canal. In comparison, stents and implants have smaller individual diameters that are between about 80 μm to about 120 μm. In some embodiments, about ten shots from an excimer laser source are applied to each eye. The energy shots may be applied to one quadrant of the eye, the inferonasal, though could be applied to other quadrants. In some embodiments, greater than about ten shots may be applied to each eye and can be applied to the inferonasal quadrant and/or to multiple eye quadrants. Because ELT is a non-thermal procedure, tissue reactions in the trabecular meshwork are not shown or activated post-operatively. The lack of heat generation in ELT allows for a nearly absent activation of postoperative tissue reactions and provides long-term stability of the pressure-reducing effects. Moreover, unlike the traditional glaucoma treatment method of shunt or stent placement, the stability of Schlemm's canal using ELT treatment remains unchanged.

Glaucoma patients suffer from increased intraocular pressure due to a blockage of fluid outflow from the eye. The various embodiments use an excimer laser to shoot perforations in the Schlemm's canal and/or trabecular meshwork of the eye. ELT treats open-angle glaucoma at the site of occurrence by increasing the permeability of the trabecular meshwork. During ELT, the laser creates a direct connection between the front chamber of the eye and the Schlemm's canal by using a fiber probe in physical contact with the trabecular meshwork.

Methods of the various embodiments include inserting a probe into an eye of a subject having glaucoma, adjusting placement of the probe to successive positions to form a succession of perforations that are transverse to Schlemm's canal in the eye by applying a plurality of shots from an excimer laser source while the probe is proximate to the trabecular meshwork and/or Schlemm's canal, thereby treating glaucoma by creating a plurality of perforations in Schlemm's canal and/or the trabecular meshwork. The perforations allow immediate drainage of fluid from the anterior chamber of the eye. The perforations also allow for increased flow of aqueous humor in the eye and reduced intraocular pressure.

Figure 42:
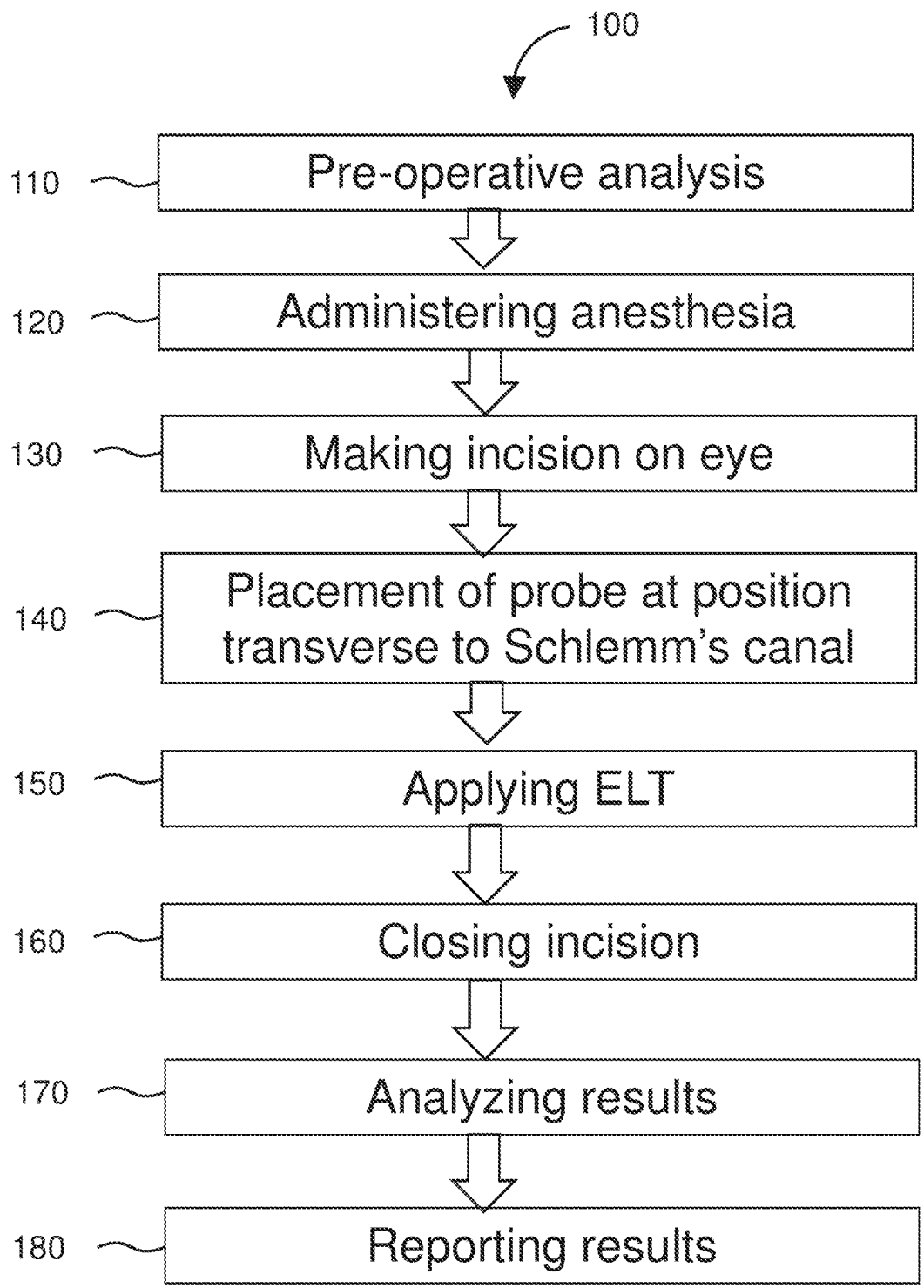
FIG. 42 is a flowchart of an embodiment of methods using placement of a probe to create perforations that form a line transverse to Schlemm's canal.

FIG. 42 shows a flowchart of an embodiment 7100 of methods of the various embodiments. Various embodiments are directed to treating a patient having glaucoma with ELT. In various embodiments, energy shots from the excimer laser are delivered by a fiber probe at a positions forming a transverse line or curve with respect to the Schlemm's canal. In some examples, methods include 7110 pre-operative analysis, such as diagnosis of the eye condition and inspection and/or visualization of the anterior chamber of the eye to aid in placement of the laser probe. In various embodiments, excimer laser trabeculostomy (ELT) is used to treat glaucoma.

In some embodiments, the method includes 7120 administering anesthesia to the patient. Topical anesthesia is commonly employed, typically by the instillation of a local anesthetic such as tetracaine or lidocaine. Lidocaine and/or a longer-acting bupivacaine anesthetic may be injected into the area surrounding (peribulbar block) or behind (retrobulbar block) the eye muscle cone to more fully immobilize the extraocular muscles and minimize pain sensation. Optionally, a facial nerve block may be performed using lidocaine and bupivacaine to reduce lid squeezing. In some cases, such as for children, patients with traumatic eye injuries, and nervous or uncooperative patients and animals, general anesthesia is administered with cardiovascular monitoring. To prepare the area for surgery, proper sterile precautions must be taken, including use of antiseptics like povidone-iodine and employment of sterile drapes, gowns, and gloves. are employed. In some cases, an eye speculum is inserted to keep the eyelids open.

A physician 7130 makes a small incision on the eye of the patient. Before the ELT procedure is performed, a small incision is made in the cornea of the eye to allow introduction of the fiber probe. Typically, the incision is about ⅛ inch or smaller.

During the excimer laser trabeculostomy procedure, a physician guides the delivery tip of the fiber probe through the corneal incision in the eye and towards the trabecular meshwork. The delivery tip is 7140 guided by the physician to successive positions transverse to the Schlemm's canal where shots are delivered (e.g., see FIG. 43 and accompanying description). A Gonio lens, endoscope, and/or illumination source may be used by the physician to aid in positioning the delivery tip. By providing a laser probe at multiple positions for shots transverse to the Schlemm's canal, or crosswise with respect to the Schlemm's canal, the energy from the excimer laser is delivered at multiple heights where the Schlemm's canal is likely to be located, thereby increasing the likelihood of perforations through the trabecular meshwork actually connecting to the Schlemm's canal. Thus, arrangement of the delivery tip at positions transverse to the Schlemm's canal achieves optimal photoablation and formation of perforations in the meshwork and/or Schlemm's canal.

Once the delivery tip is at a given position of the successive transverse positions, the physician 7150 applies ELT treatment to the patient by delivering a series of shots of laser energy to the trabecular meshwork and Schlemm's canal. The physician applies pulsed photoablative energy. In some examples, a physician creates about 10 ELT sites in an eye of the patient. In some examples, the physician creates greater than about 10 ELT sites per eye of the patient. A small amount of bloody reflux from Schlemm's canal confirms each opening. The fiber probe is removed from the eye. The TOP decreases immediately after administering the ELT procedure.

After applying ELT treatment, a physician 7160 closes the incision. Typically, a physician uses sutures to close the incision. Some physicians place a suture in the incision and other physicians reserve a suture for instances involving persistent leakage.

Methods of the various embodiments include 7170 analyzing post-operative results and 7180 reporting results and/or scheduling a post-operative follow-up appointment with the patient after surgery. For example, the physician's analysis may include observing a small amount of bloody reflux from Schlemm's canal to confirm each opening. By observing the bloody reflux and drainage of aqueous humor, the physician is able to immediately verify the effectiveness of the laser treatment. In turn, the physician may report the results to the patient, prescribe post-operative medication, such as topical antibiotics and steroid drops, and schedule any follow-up post-operative visits with the patient. Topical antibiotics and steroid drops are typically prescribed and used by the patient for 1 to 2 weeks post-operatively.

Figure 43:
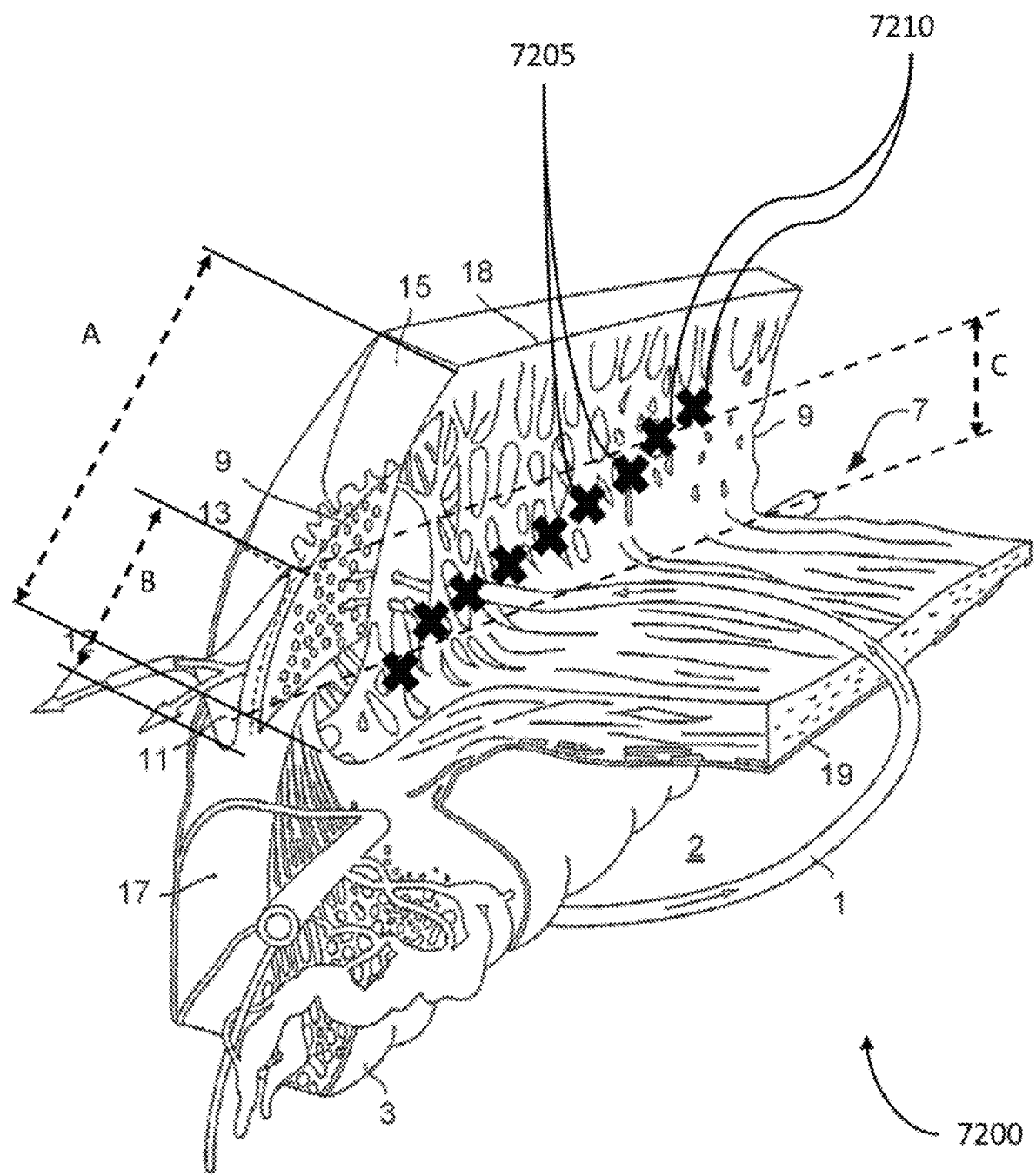
FIG. 43 is a perspective fragmentary view of the anatomy within the anterior chamber of an eye depicting the corneoscleral angle, with shots applied to the trabecular meshwork in a transverse line.

FIG. 43 is a perspective fragmentary view of the anatomy within the anterior chamber of an eye depicting the corneoscleral angle similar to FIG. 2, with locations of shots applied to the trabecular meshwork depicted with x's and shown forming a transverse line. As described herein, an ELT procedure is performed by perforating the trabecular meshwork 9, 13 of an eye. This permits fluid in a flow 1 to pass through the trabecular meshwork 9, 13 and into Schlemm's canal 11, thereby reducing the intraocular pressure in the eye. As shown, the trabecular meshwork 9, 13 may have a height of a distance A, while the Schlemm's canal 11, which is concealed to an ELT operator beneath the trabecular meshwork 9, 13, may have a height of B. Because an operator may not be able to see the Schlemm's canal 11 under the trabecular meshwork 9, 13, an operator may miss the Schlemm's canal with one or more shots and an ELT procedure can fail or be less effective. If an operator applied shots in a straight line, every shot has the potential to miss the Schlemm's canal, therefore potentially causing a failed procedure.

As shown in FIG. 43, shots 7205, 7210 may be applied in a line that is transverse to the Schlemm's canal, to ensure that at least some of the shots are correctly applied and create a perforation through the trabecular meshwork 9, 13 and into the Schlemm's canal 11. In other words, since the shots 7205 and 7210 are applied in a line that transversely crosses the width C where the trabecular meshwork 9, 13 and the Schlemm's canal 11 actually align, some of the shots (e.g., shots 7205) are successful, helping increase the likelihood that a procedure is successful.

In the example of FIG. 43, nine total shots (x's) are shown, and at least six of those shots are successful, with a possible seventh right on the border of being successful. As such, the method of applying successive shots along a transverse line with respect to the Schlemm's canal may increase the number of successful outcomes by ensuring that at least some shots are successful. Such a method may be particularly useful if a patient has a small Schlemm's canal, or the operators visibility of a particular eye is poor. In other words, instead of having to guess where Schlemm's canal is, an operator may take a systematic approach as shown in FIG. 43 to ensure that a procedure is successful. In various embodiments, if a certain number of successful shots or perforations are desired, the total number of shots may be increased. In this way, an operator can account for a certain number of shots that may be unsuccessful. For example, nine shots are applied in FIG. 43 with at least six being successful. If it is desired to have at least ten successful shots, the operator may apply, for example, fifteen shots or some greater number than ten, leaving room for the transverse line to have some outliers that are not successful.

Personalization of Excimer Laser Fibers

Glaucoma is a group of eye conditions which result in damage to the optic nerve and lead to vision loss. While glaucoma can occur at any age, it is more common in older adults and is one of the leading causes of blindness for people over the age of 60. A major risk factor in glaucoma is ocular hypertension, in which intraocular pressure is higher than normal. An elevated intraocular pressure can lead to atrophy of the optic nerve, subsequent visual field disturbances, and eventual blindness if left untreated.

Intraocular pressure is a function of the production of aqueous humor fluid by the ciliary processes of the eye and its drainage through a tissue called the trabecular meshwork. The trabecular meshwork is an area of tissue in the eye located around the base of the cornea and is responsible for draining the aqueous humor into a lymphatic-like vessel in the eye called Schlemm's canal, which subsequently delivers the drained aqueous humor into the bloodstream. Proper flow and drainage of the aqueous humor through the trabecular meshwork keeps the pressure inside the eye normally balanced. In open-angle glaucoma, the most common type of glaucoma, degeneration or obstruction of the trabecular meshwork can result in slowing or completely preventing the drainage of aqueous humor, causing a buildup of fluid, which increases the intraocular pressure. Under the strain of this pressure, the optic nerve fibers become damaged and may eventually die, resulting in permanent vision loss.

If treated early, it is possible to slow or stop the progression of glaucoma. Depending on the type of glaucoma, treatment options may include eye drops, oral medications, surgery, laser treatment, or a combination of any of these. For example, treatment of open-angle glaucoma may include surgical treatments, such as filtering surgery, in which an opening is created in the sclera of the eye and a portion of the trabecular meshwork is removed, and surgical implantation of stents or implants (i.e., drainage tubes), in which a small tube shunt is positioned within the eye to assist in fluid drainage. However, such treatments are highly invasive and may present many complications, including leaks, infections, hypotony (e.g., low eye pressure), and require post-operative, long-term monitoring to avoid late complications.

More recently, minimally invasive laser treatments have been used to treat glaucoma. In such treatments, the surgeon uses a laser to thermally modify and/or to puncture completely through various structures, including the trabecular meshwork and/or Schlemm's canal. For example, a laser trabeculostomy is a procedure in which a surgeon guides a working end of a laser fiber through a corneal incision of the eye and towards the trabecular meshwork and applies laser energy to destroy portions of the meshwork to create channels in the meshwork which allow aqueous humor to flow more freely into the Schlemm's canal. A great degree of precision is required during minimally invasive laser treatments. For example, a surgeon must be able to properly position the laser fiber at a correct position relative to the trabecular meshwork and Schlemm's canal to ensure that the resulting perforations, or channels, created by the laser are optimal. However, current laser fiber options are limited. Most laser fibers are similarly constructed and have similar features. As a result, surgeons have very few options when selecting a laser fiber of their choice. Rather, surgeons are forced to use laser fibers that lack certain qualities that a given surgeon requires when performing certain procedures, such as desired feel, feedback, and overall function of a laser fiber. As a result, the laser treatment may be inadequate, as the desired drainage may not be achieved, and thus patients may require additional post-operative procedures to lower the intraocular pressure. For example, with current laser fiber options, a surgeon may position the laser too close or too far from the trabecular meshwork and Schlemm's canal and/or position the laser at improper angles relative to the trabecular meshwork and Schlemm's canal, resulting in unintended collateral tissue damage or the creation of channels that inadequate and do not provide the desired drainage.

Various embodiments provide personalized laser probes for use in laser systems. The laser probes are single-use, disposable probes configured for use with a laser unit. The laser unit includes a laser source for generating laser energy to be provided to a laser probe coupled thereto. Each laser probe is a handheld device, which includes a handheld body and an optical fiber, including a fiber optic core, extending therethrough. Upon coupling the laser probe to the laser unit, the fiber optic core is adapted to direct laser radiation from the laser source to delivery tip of the probe for transmitting laser energy to a desired treatment area. Each laser probe includes one or more characteristics tailored to a given user (e.g., a surgeon or other medical professional to perform a procedure involving laser treatment).

The specific characteristics of any given probe are based on individual preferences of a given user. The characteristics may generally relate to shape and/or dimensions of portions of the probe as well as physical qualities of portions of the probe. In some embodiments, the handheld body of a given probe may include specific dimensions, including width, length, and diameter, based on individual preferences of a surgeon to improve fit and feel. In some embodiments, the profile of the delivery tip of the fiber optic core may be shaped based on preferences of a surgeon, wherein the tip may be beveled at a desired angle to enable more precise control over the procedure. In some embodiments, the distal end of the laser probe may have a specific degree of flexibility or rigidity based on based on preferences of a surgeon, further providing improved feel and maneuverability over the procedure.

The personalization of laser probes provides surgeons with tailored fit, feel, and function. Surgeons are better equipped to successfully perform a given procedure that may otherwise prove difficult due to the lack of variation among laser fiber options. In particular, the laser probes and laser unit of various embodiments may be used for permanent treatment of glaucoma using laser trabeculostomy. By providing personalized laser probes, a surgeon is more comfortable with the laser probe and able to perform the procedure with the required precision to ensure optimal laser treatment of the target area. In particular, by using a personalized laser probe, the surgeon is able to better position laser emission transverse to the Schlemm's canal, to create perforations, or channels, to improve fluid drainage, increase flow of aqueous humor, and reduce pressure in the eye. Arranging the laser probe at a position transverse to Schlemm's canal provides optimum results by providing a greater amount of surface area for photoablation by the laser, resulting in improved perforation and thus improved fluid drainage.

Various embodiments provide personalized laser probes for use in laser systems. The laser probes are single-use, disposable probes configured for use with a laser unit. The laser unit includes a laser source for generating laser energy to be provided to a laser probe coupled thereto. Each laser probe is a handheld device, which includes a handheld body and an optical fiber, including a fiber optic core, extending therethrough. Upon coupling the laser probe to the laser unit, the fiber optic core is adapted to direct laser radiation from the laser source to delivery tip of the probe for transmitting laser energy to a desired treatment area.

Each laser probe includes one or more characteristics tailored to a given user (e.g., a surgeon or other medical professional to perform a procedure involving laser treatment). The personalization of laser probes provides surgeons with tailored fit, feel, and function. Surgeons are better equipped to successfully perform a given procedure that may otherwise prove difficult due to the lack of variation among laser fiber options. In particular, the laser probes and laser unit of various embodiments may be used for permanent treatment of glaucoma using laser trabeculostomy. By providing personalized laser probes, a surgeon is more comfortable with the laser probe and able to perform the procedure with the required precision to ensure optimal laser treatment of the target area. In particular, by using a personalized laser probe, the surgeon is able to better position laser emission transverse to the Schlemm's canal, to create perforations, or channels, to improve fluid drainage, increase flow of aqueous humor and reduce pressure in the eye. Arranging the laser probe at a position transverse to Schlemm's canal provides optimum results by providing a greater amount of surface area for photoablation by the laser, resulting in improved perforation and thus improved fluid drainage.

The system of the various embodiments may be well suited for intraocular procedures in which laser treatment of target tissues is desired. In particular, the laser source and laser probes of the various embodiments may be used for treating glaucoma and useful in performing a laser trabeculostomy. However, it should be noted that the system consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

Figure 44:
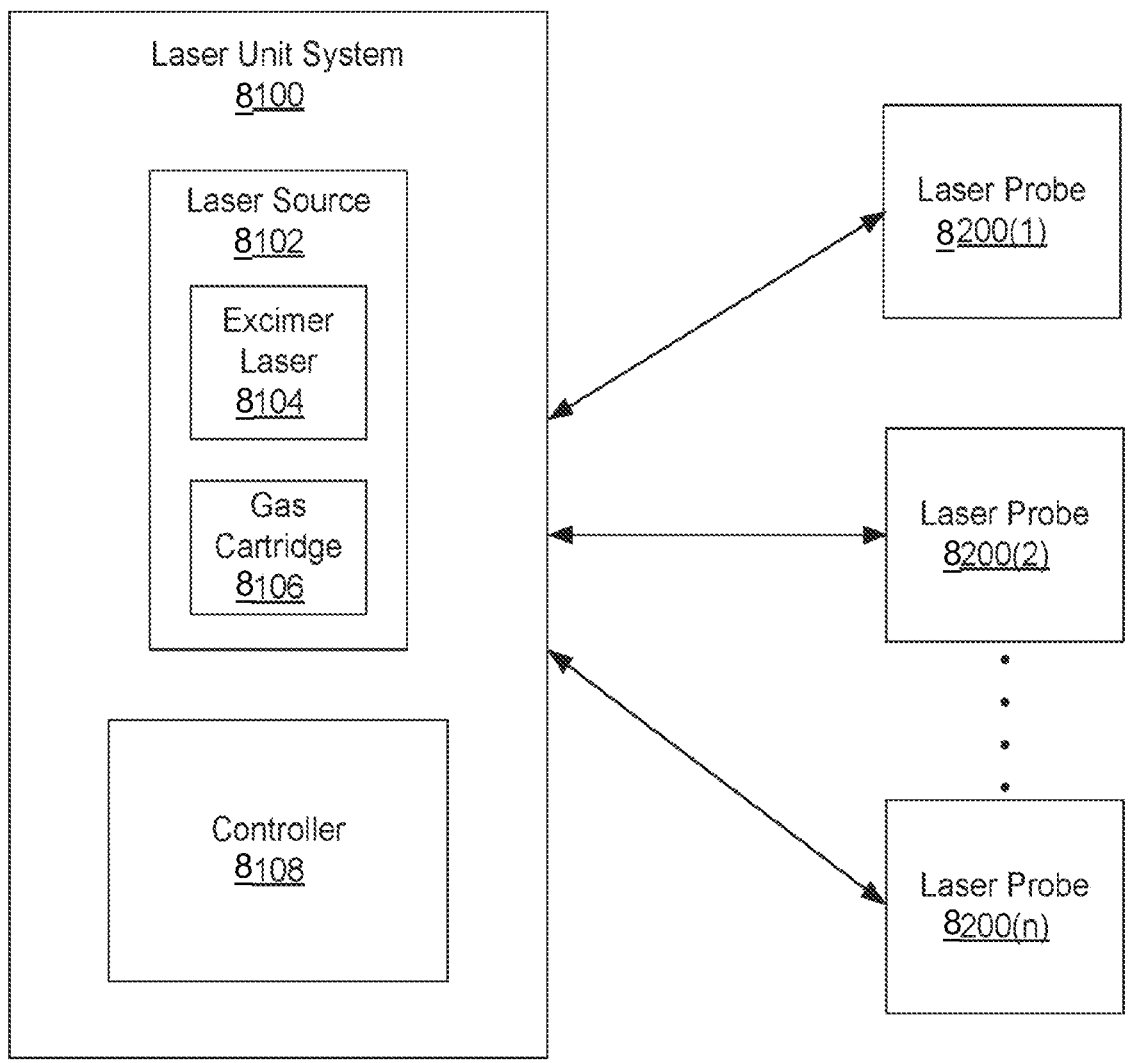
FIG. 44 diagrams an excimer laser system of the present disclosure.
Figure 45:
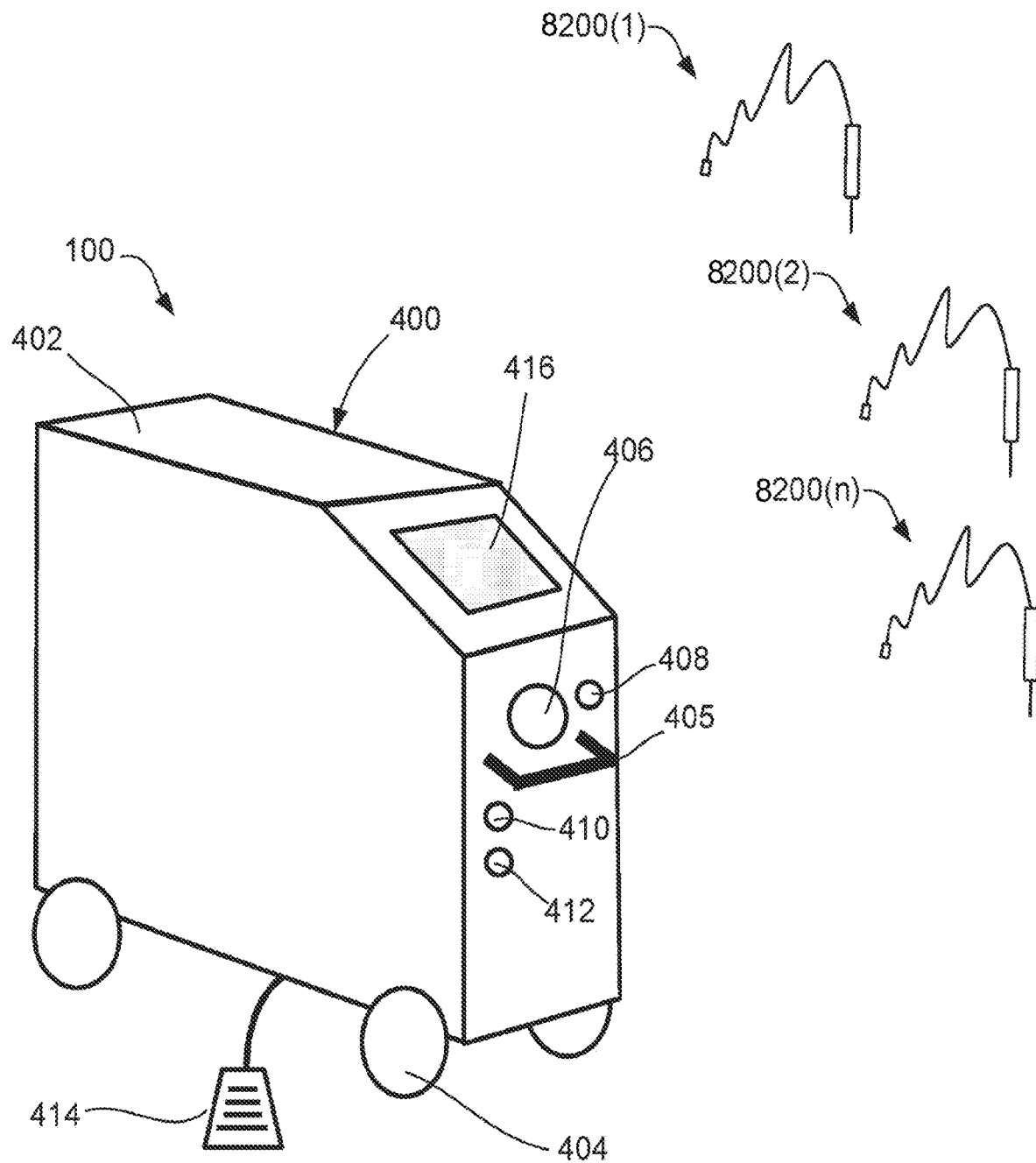
FIG. 45 shows an embodiment an excimer laser unit.

FIG. 44 diagrams an excimer laser system, including a laser unit system 8100 and a plurality of laser probes 8200(1), 8200(2), 8200(n) couplable to the laser unit system 8100. The system 8100 includes a laser source 8102 for generating laser energy and a controller 8108 for controlling output of the laser energy. The laser source 8102 includes an excimer laser 8104 and a gas cartridge 8106 for providing the appropriate gas combination to the laser 8104. The excimer laser 8104 is a form of ultraviolet laser that generally operates in the UV spectral region and generates nanosecond pulses. The excimer gain medium (i.e., the medium contained within the gas cartridge 8106) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 8104 of the present system 8100 is an XeCl excimer laser and emits a wavelength of 308 nm.

As described in greater detail herein, many of the components of the laser unit system 8100 may be contained in a housing, such as a moveable platform, to be provided in a setting in which the procedure is to be performed (e.g., operating room, procedure room, outpatient office setting, etc.) and the probes 8200(1)-8200(n) may connect to the housing for use during treatment. Upon coupling a probe 8200 to the housing, a fiber optic core of the probe 8200 is coupled to the laser source 8102 and adapted to direct laser radiation from the laser source 8102, through the fiber, and to the treatment area.

The controller 8108 provides an operator (i.e., surgeon or other medical professional) with control over the output of laser signals (from the excimer laser 8104 to a fiber optic core of the probe 8200) and, in turn, control over the transmission of laser energy from probe 8200. The controller 8108 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hard-wired circuitry, programmable circuitry such as computer processors comprising one or more individual instruction processing cores, state machine circuitry, and/or firmware that stores instructions executed by programmable circuitry. For example, the controller 8108 may include a hardware processor coupled to non-transitory, computer-readable memory containing instructions executable by the processor to cause the controller to carry out various functions of the laser system 8100 as described herein.

FIG. 4 shows an embodiment of an excimer laser unit 100 (e.g., laser system 8100) provided in an instrument 400. As previously described, one or more components of the system 100 can be contained within the instrument 400. In the present embodiment, the laser source 8102 (including the excimer laser 8104 and gas cartridge 1806) and controller 8108 are contained within a housing 402. The housing 402 has wheels 404 and is portable. The instrument 400 further includes a push-pull handle 405 which assists with portability of the instrument 400. The instrument 400 further includes a connection port 406 for receiving a connecting end of the laser probe 8200 to establish a connection between a fiber optic core of the probe 8200 and the laser source 8102. The instrument 400 further includes various inputs for the operator, such as an emergency stop button 410, and a power switch 412. The instrument 400 further includes a foot pedal 414 extending from the housing 402 and is operable to provide control over the delivery of shots from the excimer laser 8104 to the fiber optic core of the probe 8200. The instrument 400 further includes a display 416, which may be in the form of an interactive user interface. In some examples, the interactive user interface displays patient information, machine settings, and procedure information. As previously described, an operator may manually input the laser probe data via the interactive user interface to thereby provide such data to the controller 8108. However, in some embodiments, the data may be automatically read from a readable device or label on the probe 8200 via an associated reader of the system 8100.

As shown, the various embodiments provide for a plurality of personalized laser probes 8200(1)-8200(n) for use with the excimer laser unit 8100. The laser probes 8200(1)-8200(n) are single-use, disposable probes configured for use with a laser unit, one at a time. Upon coupling a laser probe 8200 to the laser unit (via the connection portion 406, the fiber optic core of the probe 8200 is adapted to direct laser radiation from the excimer laser 8104 to a delivery tip of the probe for transmitting laser energy to a desired treatment area. As will be described in greater detail herein, each laser probe 8200(1)-8200(n) may include one or more characteristics tailored to a given user (e.g., a surgeon or other medical professional to perform a procedure involving laser treatment). As such, only single excimer laser unit 8100 is required and a plurality of differently configured probes 8200(1)-8200(n) can be used with the unit 8100.

FIGS. 5 and 6 show an embodiment of a probe 500 that may be used with the excimer laser system 8100 (e.g., one of the probes 8200(1)-8200(n)). FIGS. 46 and 47 show cross-sectional views of the probe 500 taken along line A-A and line B-B of FIG. 6, respectively. As shown, a fiber optic core 518 runs through the probe 500 and forms part of the connector 502. A protective sheath 516 surrounds the fiber optic core 518. In some examples, the protective sheath 516 is a protective plastic or rubber sheath. The fiber optic core 518 further form part of the delivery tip 506 of the probe 500. A metal jacket 520 surrounds the fiber optic core 518 and optical fiber 520. In some instances, a stainless steel jacket 520 surrounds and protects the fiber optic core 518.

Each laser probe includes one or more characteristics tailored to a given user (e.g., a surgeon or other medical professional to perform a procedure involving laser treatment). The specific characteristics of any given probe are based on individual preferences of a given user. The characteristics may generally relate to shape and/or dimensions of portions of the probe as well as physical qualities of portions of the probe. In some embodiments, the handheld body 508 of a given probe may include specific dimensions, including width, length, and diameter, based on individual preferences of a surgeon to improve fit and feel.

Figure 50:
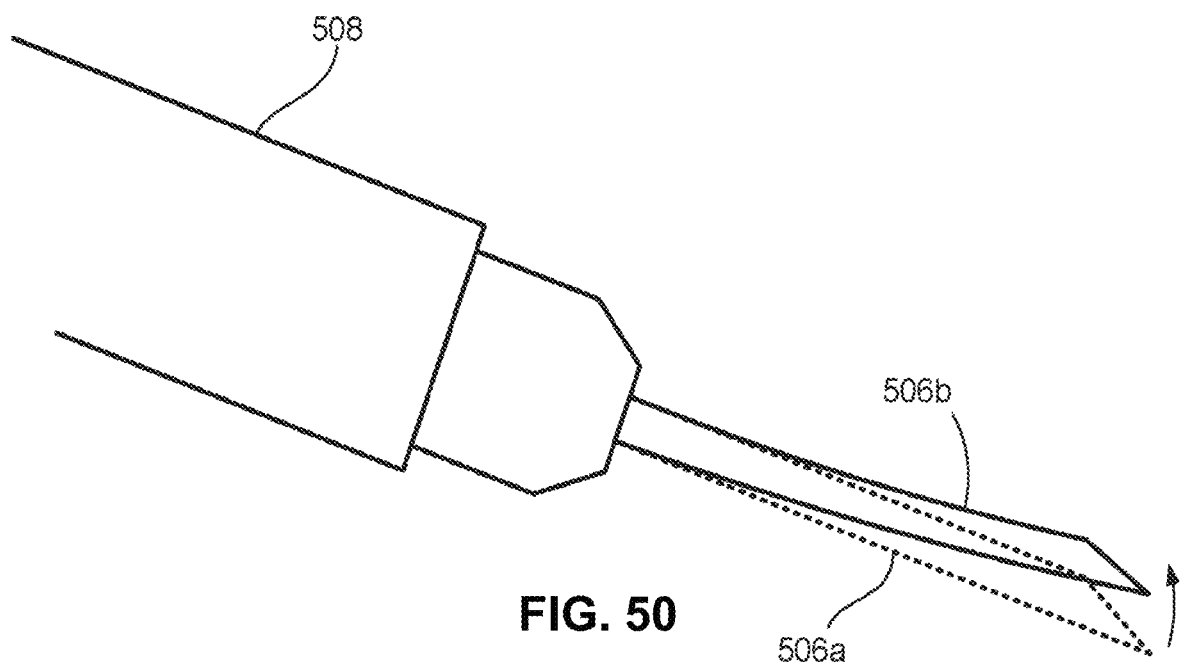
FIGS. 50 and 51 show enlarged views of a distal portion of a probe flexing in different directions.
Figure 51:
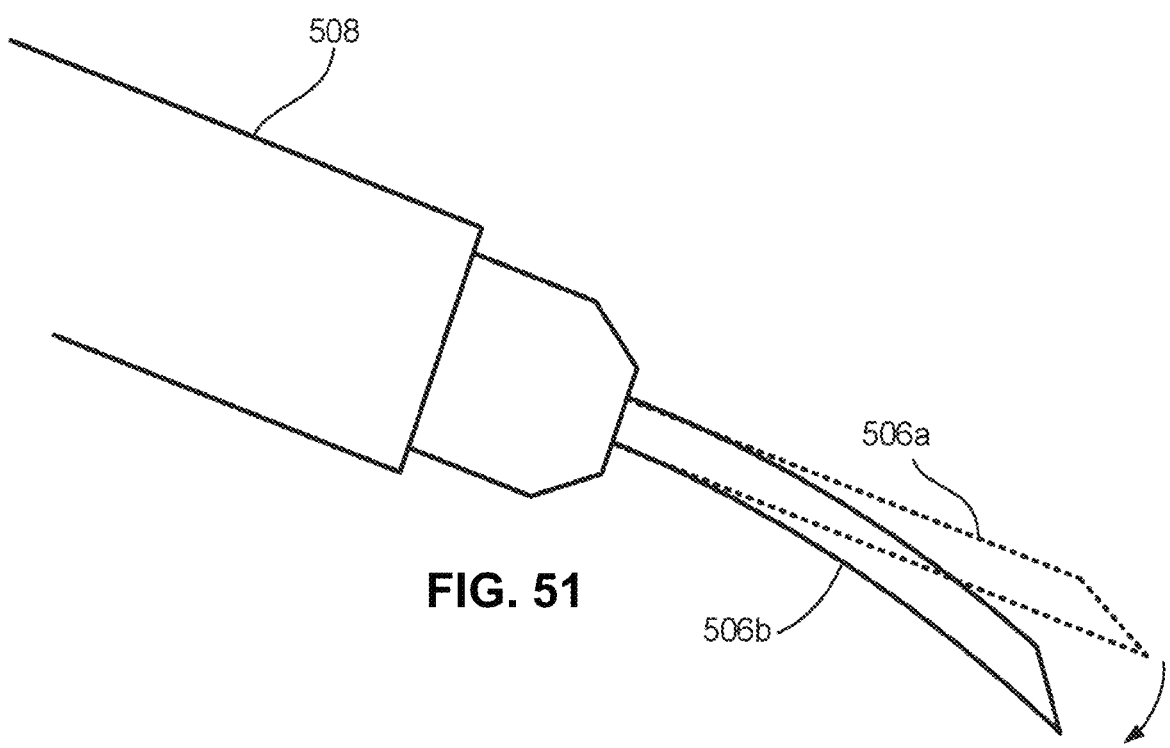

In some embodiments, the profile of the delivery tip 506 of the fiber optic core may be shaped based on preferences of a surgeon, wherein the tip may be beveled at a desired angle to enable more precise control over the procedure. FIG. 48 shows an enlarged view of a distal portion of a probe. FIGS. 49A and 49B show enlarged views of delivery tips 506 of a probe having different bevel angles 507. For example, as shown in FIG. 49A, the bevel angle $\theta_1$ may be greater than the bevel angle $\theta_1$, as determined by a user's individual preferences. Additionally, or alternatively, the distal end of the laser probe may have a specific degree of flexibility or rigidity based on based on preferences of a surgeon, further providing improved feel and maneuverability over the procedure. For example, FIGS. 50 and 51 show enlarged views of a distal portion 506a of a probe flexing in different directions (flexed distal portion 506b). As such, the outer jacket 520 surrounding said fiber optic core 518 may include certain materials having properties allowing for desired flex or rigidity.

The personalization of laser probes provides surgeons with tailored fit, feel, and function. Surgeons are better equipped to successfully perform a given procedure that may otherwise prove difficult due to the lack of variation among laser fiber options. In particular, the laser probes and laser unit of various embodiments may be used for permanent treatment of glaucoma using laser trabeculostomy. For example, during a laser trabeculostomy procedure using the laser system and probes, a physician guides the delivery tip of the probe through a corneal incision in the eye and towards the trabecular meshwork. A Gonio lens and/or illumination source may be used by the physician to aid in positioning the delivery tip. In some examples, the physician uses a light source, such as Gonio lens, endoscope, or other illumination source, to aid in adjusting placement of the probe.

By providing personalized laser probes, a surgeon is more comfortable with the laser probe and able to perform the procedure with the required precision to ensure optimal laser treatment of the target area. For example, the surgeon is able to better position laser emission transverse to the Schlemm's canal. Once the delivery tip is at a position transverse to the Schlemm's canal, the physician delivers a series of shots of laser energy to the trabecular meshwork. By providing a laser probe at a position transverse to the Schlemm's canal, or crosswise to the Schlemm's canal, the laser is delivered to a greater amount of surface area than if the laser was in a parallel or perpendicular position to the Schlemm's canal. Thus, arrangement of the delivery tip at a position transverse to the Schlemm's canal achieves optimal photoablation and channel formation in the meshwork and/or Schlemm's canal. The orientation and positioning of the delivery tip is critical when creating channel formation in the tissue, as achieving transverse placement of channels in the meshwork relative to Schlemm's canal provides optimal drainage. Arranging the laser probe at a position transverse to Schlemm's canal provides optimum results by providing a greater amount of surface area for photoablation by the laser, resulting in improved perforation and thus improved fluid drainage.

Enhanced Fiber Probes for Elt

Patients suffering from glaucoma experience vision loss from a build-up of fluid in the anterior chamber of the eye. The fluid build-up increases the pressure in the eye and causes damage to the optic nerve. If left untreated, the damage to the optic nerve will lead to blindness.

Traditional pharmaceuticals prescribed to treat glaucoma do not provide a permanent solution and instead manage the condition by lowering pressure in the eye. For example, some medications decrease production of the fluid, while other medications increase drainage of the fluid. Traditional surgical treatments are also used to lower pressure, for example, by inserting an implant into the eye to increase drainage. However, these procedures have risks associated with them, such as dislodgement of the implant.

The various embodiments provide systems and methods of treating glaucoma using fiber probes that have a programmable number of laser shots for use during an excimer laser trabeculostomy (ELT) procedure. ELT is a minimally invasive method of treating glaucoma that does not involve implants. Instead, an excimer laser is used to permanently perforate the drainage system in the eye to increase drainage of fluid. ELT instruments require fiber probes to deliver the laser pulse to the eye. In the various embodiments, a fiber probe connected to the ELT instrument is programmable to deliver a variable number of laser shots and monitor the number of shots delivered by the probe, thereby allowing for personalized treatment of glaucoma.

Existing fiber probes are operable for a fixed number of laser shots. Typically, a maximum number of laser shots is delivered by each existing fixed-use fiber probe. If a physician requires greater than 10 laser shots for treatment, the ELT procedure is interrupted in order to change out one fixed-use fiber probe for another fixed-use fiber probe.

Because ELT procedures often require more than a standard number of laser shots for treatment of glaucoma, the various embodiments provide fiber probes programmable to increase the maximum number of laser shots for each probe. By programming the fiber probes, interruptions in the ELT procedure are avoided, such as delays caused by replacing an expended fixed-use fiber probe with a fresh fixed-use fiber probe in order to continue treatment of an eye. The various embodiments therefore avoid interruptions to the surgical process in order to allow a change of equipment.

Methods and systems of the various embodiments allow programming of a fiber probe to deliver a variable number of laser shots and monitor the number of shots delivered by the probe. In various embodiments, once the fiber probe is connected to the ELT instrument, the fiber probe may be programmed. The ELT instrument comprises an interactive user interface, or display panel, that is communicatively coupled with a controller and a processor. Settings input by the user into the interactive user interface are processed and implemented.

In an example, a physician uses the interactive user interface to enter a numerical value for the variable number of laser shots deliverable by the probe. The numerical value for the variable number of laser shots is programmable within a range and is adjustable from a minimum amount to a maximum amount. For safety purposes, the manufacturer may set a predefined limit on the maximum number of shots.

The physician may program the variable number of deliverable laser shots up to the manufacturer-set maximum number. The ELT instrument programs the variable number of laser shots deliverable by the fiber probe and subsequently monitors the number of laser shots delivered by the fiber probe. The various embodiments therefore provide personalized glaucoma treatment, which has the benefit of preventing reuse of medical equipment and avoids the detriment of not treating a patient in an optimal manner.

In some examples, the variable number of deliverable laser shots is determined based on pre-operative analysis conducted by the physician. For example, a physician may review the condition of glaucoma in the subject and decide to administer 15 laser shots per eye using ELT treatment. The physician is then able to program the fiber probe accordingly and perform the ELT procedure to deliver as many laser shots as programmed without interrupting the treatment to change out fiber probes. Thus, various embodiments described herein provide personalized laser surgical intervention that increases efficiency of ELT procedures and avoids delays from changing out fiber probes.

During the ELT procedure, after programming the fiber probe, the physician guides the delivery tip of the fiber probe through a corneal incision in the eye and towards the trabecular meshwork. In some examples, various embodiments further comprise administering anesthesia to the subject before making the incision and inserting the probe. Typically, the incision has a length of about ⅛ inch or smaller. In some examples, one or more sutures are used to close the incision after ELT treatment. The delivery tip is guided by the physician to a position transverse to the Schlemm's canal to create permanent perforations in the trabecular meshwork and/or Schlemm's canal. Fluid drainage from the anterior chamber of the eye is immediately improved once perforations are created in the meshwork and/or Schlemm's canal by the laser. The perforations also increase blood flow and reduce pressure in the eye. In some cases, the physician uses a Gonio lens, endoscope, or other illumination source to aid in positioning the delivery tip of the fiber probe.

Once the delivery tip is at a position transverse to the Schlemm's canal, a series of shots of laser energy are delivered to the trabecular meshwork. By providing a laser probe at a position transverse to Schlemm's canal, or crosswise to Schlemm's canal, energy from the laser is delivered to a greater amount of surface area than if the fiber probe was in a position parallel to or perpendicular to Schlemm's canal. Arrangement of the delivery tip at a position transverse to Schlemm's canal achieves optimal photoablation and formation of perforations for drainage.

To improve drainage of the aqueous humor from the anterior chamber of the eye, a plurality of permanent perforations is lasered into the trabecular meshwork and/or Schlemm's canal by the ELT procedure. Each ELT perforation has a diameter of about 200 μm, which is determined by the dimensions of the delivery tip. These dimensions could be modified to increase or decrease the ELT perforation diameter. In existing fiber probes for use in ELT procedures, the fiber probes are set to deliver a maximum, fixed number of laser shots. For example, the maximum, fixed number may be 10 laser shots. Various embodiments allow the physician to program the number of laser shots deliverable by the fiber probes, thereby providing fiber probes with a variable number of deliverable laser shots. The number of laser shots is programmable within a range and is adjustable from a minimum amount to a maximum amount. According to various embodiments, a physician can attach a fiber probe to the ELT instrument and enter a range for number of shots deliverable by the attached fiber probe using the interactive user interface on the instrument. In some examples, the number of deliverable laser shots is a variable number. In some examples, the variable number of deliverable shots is greater than about 10 shots.

In an example, after examining a subject having glaucoma, a physician determines that 15 shots per eye are needed for treatment. Using the various embodiments, the physician programs a fiber probe to deliver 15 laser shots as a maximum number in the range of laser shots deliverable by the probe. In such a scenario, the physician uses a fiber probe that is programmed to deliver 15 laser shots to treat glaucoma in a first eye of the subject. For sterilization purposes, a second fiber is programmed and used to deliver 15 laser shots in a second eye of the subject. The physician uses two fiber probes during the ELT procedure, one probe for each eye. In contrast, twice as many fiber probes would be used for the same ELT treatment plan if the physician was using traditional, fixed number fiber probes with 10 shots set as the maximum fixed number of shots. A first fixed number probe would be used to apply a maximum 10 shots to a first eye, the first fixed number probe would be replaced with a second fixed number probe, and the remaining 5 shots in the treatment plan would be applied to the first eye. The process would be repeated for treatment of a second eye of the subject, with a third fixed number probe used to apply a maximum 10 shots to the second eye and a fourth fixed number probe used to apply the remaining 5 shots in the treatment plan to the second eye.

In an embodiment, the input options on the interactive user interface are directed to setting the pulse, width, and amplitude of the laser. Due to safety concerns, a maximum setting for each of the pulse, width, and amplitude are typically pre-defined by the manufacturer. The user may select values within the predefined ranges set by the manufacturer.

Various embodiments use a 308-nm xenon-chloride ultraviolet excimer laser. The 308-nm xenon-chloride ultraviolet excimer laser causes minimal thermal damage compared with visible or infrared lasers. In some examples, the excimer laser is an encapsulated xenon chloride (XeCl) excimer laser such as the EX TRA LASER manufactured by MLase AG. Because ELT is a non-thermal procedure, tissue reactions in the trabecular meshwork are not shown or activated post-operatively. The lack of heat generation in ELT allows for a nearly absent activation of postoperative tissue reactions and provides long-term stability of the pressure-reducing effects.

Moreover, to avoid the corneal absorption of laser radiation, an optical fiber is used to deliver the energy. A delivery tip of the fiber probe comprises the optical fiber jacketed in metal, such as stainless steel. In some examples, the delivery tip is beveled (e.g., at 0°, 15°, and 45° with respect to the tip). The fiber probe comprises an optical fiber suitable for UV light that is embedded into a handheld laser applicator. In some examples, a FIDO LASER APPLICATOR manufactured by MLase AG is used as the fiber probe.

Systems and methods of the various embodiments herein treat glaucoma using excimer laser trabeculostomy (ELT). Multiple shots from the excimer laser are administered to the patient in order to shoot holes, or perforations, in the trabecular meshwork and/or Schlemm's canal. ELT converts trabecular meshwork tissue into gas by photoablation. By permanently perforating Schlemm's canal and/or the trabecular meshwork, built-up fluid in the eye is immediately allowed to drain. Moreover, because the perforations allow for increased blood flow and fluid drainage, subsequent vision loss from damage to the optic nerve due to any build-up is thereby avoided.

In existing fiber probes for use ELT procedures, the fiber probes are set to deliver a maximum fixed number of laser shots. Various embodiments allow the physician to program the number of laser shots deliverable by the fiber probes, thereby providing fiber probes that deliverable a variable number of laser shots. Once the delivery tip is at a position transverse to the Schlemm's canal, the physician applies pulsed photoablative energy to create ELT sites or perforations in the trabecular meshwork and/or Schlemm's canal. In some examples, a physician creates greater than about 10 ELT sites per eye.

Figure 52:
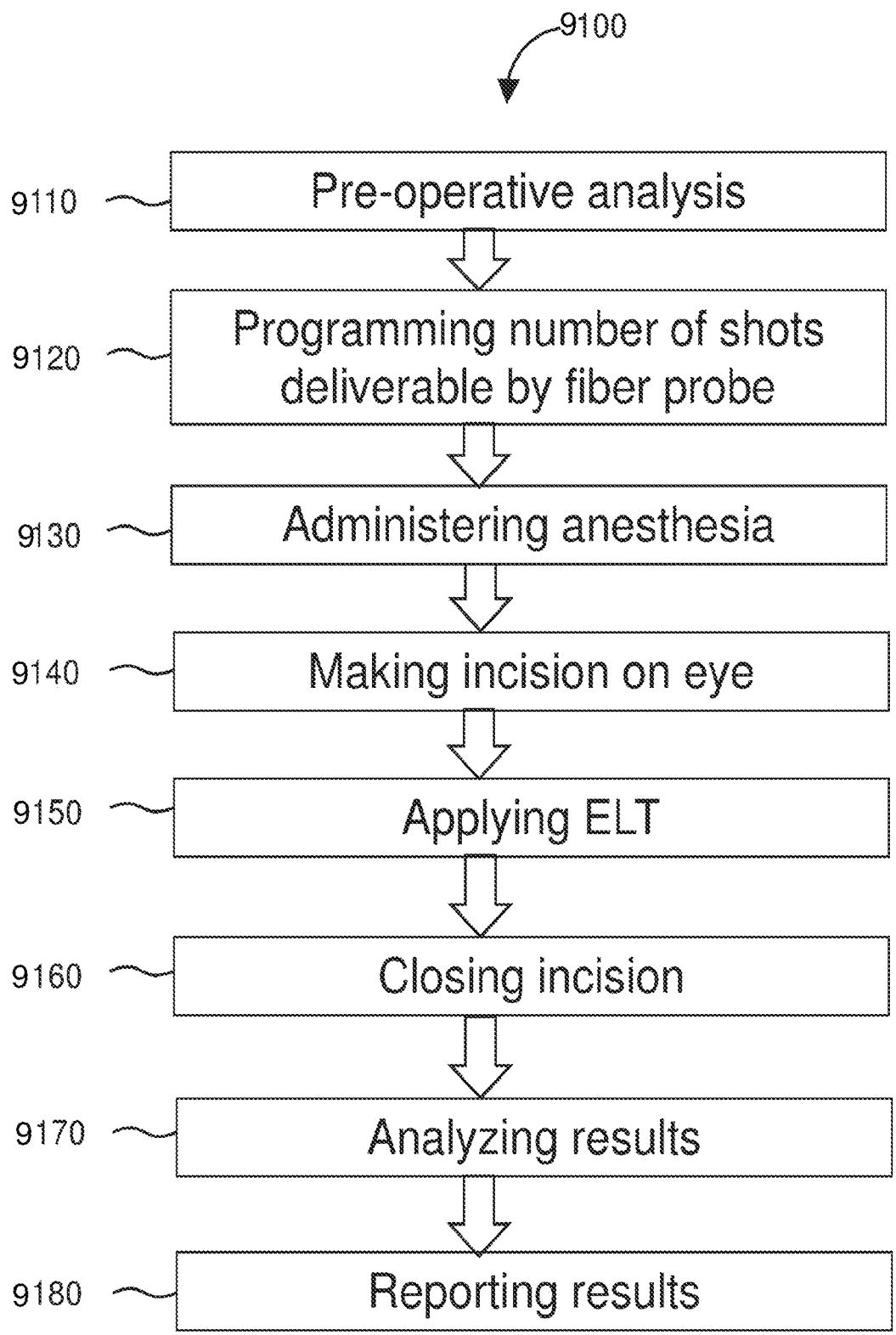
FIG. 52 is a flowchart of an embodiment of methods of applying ELT with programmable customizations.

FIG. 52 shows a flowchart of an embodiment 9100. Various embodiments are directed to treating a patient having glaucoma with ELT. In various embodiments, the energy shots delivered from the excimer laser are at a position transverse to the Schlemm's canal. In some examples, methods include 9110 pre-operative analysis, such as diagnosis of the eye condition, inspection and/or visualization of the anterior chamber of the eye to aid in placement of the laser probe, and analysis of number of laser shots needed for treatment. In various embodiments, excimer laser trabeculostomy (ELT) is used to treat glaucoma.

Methods of the various embodiments include 9120 programming the number of shots deliverable by the fiber probe. In existing fiber probes for use ELT procedures, the fiber probes are set to deliver a maximum, fixed number of laser shots. Methods and systems of the various embodiments allow the physician to program the number of laser shots deliverable by the fiber probes. The number of laser shots is programmable within a range and is adjustable from a minimum amount to a maximum amount. A physician can attach a fiber probe to the ELT instrument and use the interactive user interface on the instrument, and subsequently the controller and processor of the ELT system, to program the fiber probe to deliver a range of laser shots.

Some embodiments of the method include 9130 administering anesthesia to the patient. Topical anesthesia is commonly employed, typically by the instillation of a local anesthetic such as tetracaine or lidocaine. Lidocaine and/or a longer-acting bupivacaine anesthetic may be injected into the area surrounding (peribulbar block) or behind (retrobulbar block) the eye muscle cone to more fully immobilize the extraocular muscles and minimize pain sensation. Optionally, a facial nerve block may be performed using lidocaine and bupivacaine to reduce lid squeezing. In some cases, such as for children, patients with traumatic eye injuries, and nervous or uncooperative patients and animals, general anesthesia is administered with cardiovascular monitoring. To prepare the area for surgery, proper sterile precautions must be taken, including use of antiseptics like povidone-iodine and employment of sterile drapes, gowns, and gloves. In some cases, an eye speculum is inserted to keep the eyelids open.

Methods of the various embodiments further include a physician 9140 making a small incision on the eye of the patient. Before the ELT procedure is performed, a small incision is made in the cornea of the eye to allow introduction of the laser probe. Typically, the incision is about ⅛ inch or smaller. During the ELT procedure, a physician guides a delivery tip of a fiber probe through the corneal incision in the eye and towards the trabecular meshwork. The delivery tip is guided by the physician to a position transverse to the Schlemm's canal. A Gonio lens, endoscope, and/or illumination source may be used by the physician to aid in positioning the delivery tip. By providing a laser probe at a position transverse to the Schlemm's canal, or crosswise to the Schlemm's canal, the laser is delivered to a greater amount of surface area than if the laser was in a parallel or perpendicular position to the Schlemm's canal. Thus, arrangement of the delivery tip at a position transverse to the Schlemm's canal achieves optimal photoablation and formation of perforations in the meshwork and/or Schlemm's canal. The orientation and positioning of the delivery tip is critical when creating perforations in the tissue, as achieving transverse placement of perforations in the meshwork relative to Schlemm's canal provides optimal drainage.

Once the delivery tip is at a position transverse to the Schlemm's canal, the physician 9150 applies ELT treatment to the patient by delivering a series of shots of laser energy to the trabecular meshwork and Schlemm's canal. The physician applies pulsed photoablative energy to create ELT sites or perforations in the trabecular meshwork and/or Schlemm's canal. Unlike traditional fiber probes that have a maximum, fixed number of deliverable laser shots, methods of the various embodiments allow the physician to program the number of shots deliverable by the fiber probe. The number of laser shots deliverable by fiber probes according to methods and systems of the various embodiments is programmable within a range and is adjustable from a minimum amount to a maximum amount.

In some examples, a physician uses a programmed fiber probe to create greater than about 10 ELT sites in an eye of the patient. A small amount of bloody reflux from Schlemm's canal confirms each opening. The fiber probe is removed from the eye. Notably, the TOP decreases immediately after administering the ELT procedure.

After applying ELT treatment, a physician 9160 closes the incision. Typically, a physician uses sutures to close the incision. Some physicians place a suture in the incision and other physicians reserve a suture for when there is persistent leakage.

Methods of the various embodiments include 9170 analyzing post-operative results and 9180 reporting results and/or scheduling a post-operative follow-up appointment with the patient after surgery. For example, the physician's analysis may include observing a small amount of bloody reflux from Schlemm's canal to confirm each opening. By observing the bloody reflux and drainage of aqueous humor, the physician is able to immediately verify the effectiveness of the laser treatment. In turn, the physician may report the results to the patient, prescribe post-operative medication, such as topical antibiotics and steroid drops, and schedule a follow-up post-operative visit with the patient. For example, topical antibiotics and steroid drops are used by the patient for 1 to 2 weeks post-operatively.

Figure 53:
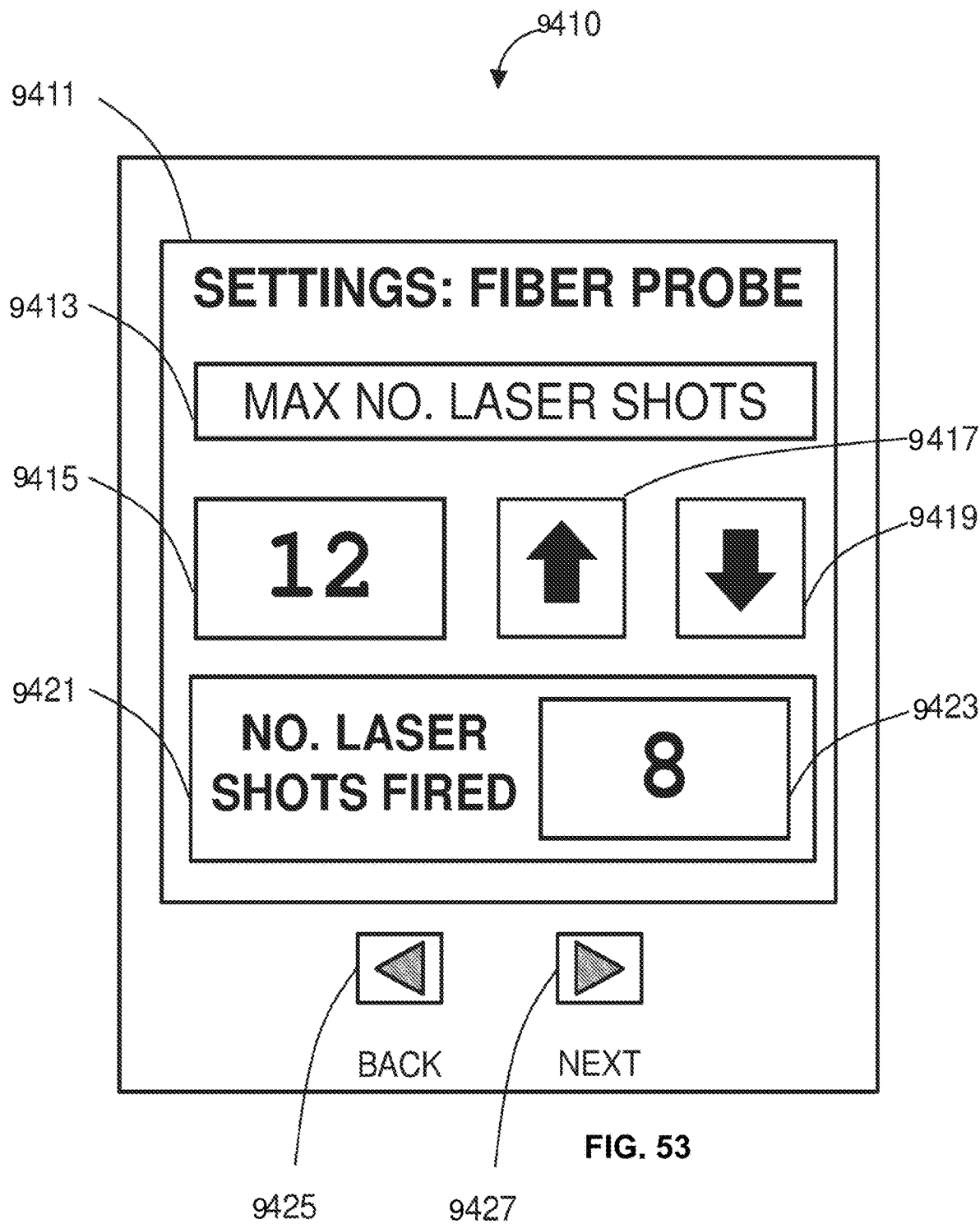
FIG. 53 shows a stylized embodiment of an interactive user interface.

FIG. 53 shows a stylized embodiment of an interactive user interface 9410 (e.g., 416 of FIGS. 4, 21, 32, 45; 6310 of FIG. 41; etc.) according to various embodiments. The interactive user interface 9410 is an interactive display screen on the ELT instrument. The interactive user interface 9410 is communicatively coupled with the controller, which allows the user (e.g., physician) to view and change settings using the interactive user interface 9410, such as via haptic feedback and/or touchscreen technologies. The interactive user interface displays a variety of information and settings, such as patient information, instrument information, and instrument settings.

Different information is displayed on a plurality of interchangeable display screens. For example, one screen may display setting information for the fiber probe, such as shown in FIG. 53, while another screen displays patient information. The user can view different screens by using button 9425 to return to a previous screen or using button 9427 to move forward to a next screen. In the embodiment shown in FIG. 53, a settings screen 9411 is shown for the fiber probe. Display box 9413 designates the setting, which is the maximum number of laser shots for the fiber probe. Display box 9415 shows the maximum number of laser shots that the user has input. To change the set maximum number of laser shots, the user can select button 9417 to increase the number in box 9415 and button 9419 to decrease the number in box 9415. Display box 9421 indicates the number of laser shots that have been fired from the probe, with the changing number shown in box 9423. The embodiment shown in FIG. 53 indicates that the fiber probe has been programmed to deliver 12 shots as the maximum number of laser shots, and so far, the fiber probe has delivered 8 laser shots.

In an embodiment, the input options on the display screen are directed to setting the pulse, width, and amplitude of the laser. Due to safety concerns, a maximum setting for each of the pulse, width, and amplitude may be pre-defined by the manufacturer. The user may select values within the pre-defined ranges set by the manufacturer.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the various embodiments described herein and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of the various embodiments and equivalents thereof.

What is claimed is:

1. A method of treating a patient having an eye condition, the method comprising:
   determining that the patient has a closed-angle or narrow-angle glaucoma, wherein the closed-angle or narrow-angle glaucoma causes at least partial blockage of fluid flow from an anterior chamber of an eye of the patient located between a cornea of the eye and a lens of the eye through a trabecular meshwork of the eye due to bulging of an iris of the eye; and
   based on the determining that the patient has the closed-angle or narrow-angle glaucoma, performing a single surgical procedure on the patient, wherein the single surgical procedure comprises:
      treating the closed-angle or narrow-angle glaucoma with a first treatment; and
      treating the patient with a second treatment different from the first treatment, wherein the treating of the patient with the second treatment comprises treating the patient with an excimer laser to create a plurality of perforations in the trabecular meshwork by applying a plurality of shots to the trabecular meshwork from the excimer laser, wherein the second treatment is configured to treat or prevent open-angle glaucoma in the eye of the patient.

2. The method of claim 1, wherein the treating the closed-angle or narrow-angle glaucoma comprises applying phacoemulsification ultrasound to the patient.

3. The method of claim 2, wherein the phacoemulsification ultrasound comprises breaking up the lens of the eye.

4. The method of claim 3, further comprising, after breaking up the lens, removing the lens from the eye of the patient.

5. The method of claim 4, further comprising, after removing the lens, replacing the lens of the eye with an artificial lens.

6. The method of claim 5, wherein the artificial lens is thinner than the lens of the eye that is removed from the eye.

7. The method of claim 6, wherein the artificial lens provides a path for fluid drainage between the artificial lens and the iris of the eye.

8. The method of claim 2, wherein the determining that the patient has the closed-angle or narrow-angle glaucoma comprises determining that the patient has closed-angle glaucoma.

9. The method of claim 1, wherein the treating of the closed-angle or narrow-angle glaucoma causes the bulging of the iris to decrease.

10. The method of claim 9, wherein the treating of the patient with the excimer laser occurs after the bulging of the iris decreases.

11. The method of claim 1, wherein the treating of the patient with the excimer laser comprises inserting an excimer laser probe into an incision of the eye of the patient.

12. The method of claim 11, the treating the closed-angle or narrow-angle glaucoma comprises inserting a phacoemulsification ultrasound probe into the incision of the eye of the patient.

13. The method of claim 12, wherein the incision has a length of about one eighth of an inch or smaller.

14. The method of claim 1, wherein the plurality of shots comprises at least ten shots.

15. The method of claim 1, further comprising administering anesthesia to the patient before the treating of the closed-angle or narrow-angle glaucoma and before the treating of the patient with the excimer laser.

16. The method of claim 1, wherein the excimer laser comprises a xenon chloride laser source.

17. A method of treating a patient having an eye condition, the method comprising:
   determining that the patient has a closed-angle or narrow-angle glaucoma, wherein the closed-angle or narrow-angle glaucoma causes at least partial blockage of fluid flow from an anterior chamber of an eye of the patient located between a cornea of the eye and a lens of the eye through a trabecular meshwork of the eye due to bulging of an iris of the eye; and
   based on the determining that the patient has the closed-angle or narrow-angle glaucoma, performing a single surgical procedure on the patient, wherein the single surgical procedure comprises:
      applying a phacoemulsification ultrasound to the patient to treat the closed-angle or narrow-angle glaucoma, wherein the phacoemulsification ultrasound is applied via a phacoemulsification probe inserted through an incision in the eye of the patient; and
      treating the patient with an excimer laser to create a plurality of perforations in the trabecular meshwork by applying a plurality of shots to the trabecular meshwork from the excimer laser, wherein the plurality of shots is applied via an excimer laser probe inserted through the incision, and wherein the treating of the patient with the excimer laser is configured to treat or prevent open-angle glaucoma in the eye of the patient.

18. The method of claim 17, the phacoemulsification ultrasound comprises breaking up the lens of the eye.

19. The method of claim 17, wherein the treating the patient with the excimer laser occurs after applying the phacoemulsification ultrasound.

\* \* \* \* \*